(12) United States Patent
Akbari et al.

(10) Patent No.: US 12,138,140 B2
(45) Date of Patent: Nov. 12, 2024

(54) WOUND COVERING FOR WOUND MONITORING AND THERAPEUTIC AGENT DELIVERY

(71) Applicant: UVic Industry Partnerships Inc., Victoria (CA)

(72) Inventors: Mohsen Akbari, Victoria (CA); Bahram Mirani, Victoria (CA); Aziz Ghahary, Vancouver (CA); Mohammad A. Siddiqui, Victoria (CA)

(73) Assignee: UVIC INDUSTRY PARTNERSHIPS INC, Victoria (CA)

( * ) Notice: Subject to any disclaimer, the term of this patent is extended or adjusted under 35 U.S.C. 154(b) by 1398 days.

(21) Appl. No.: 16/614,328

(22) PCT Filed: May 17, 2018

(86) PCT No.: PCT/IB2018/053491
§ 371 (c)(1),
(2) Date: Nov. 15, 2019

(87) PCT Pub. No.: WO2018/211458
PCT Pub. Date: Nov. 22, 2018

(65) Prior Publication Data
US 2020/0188180 A1 Jun. 18, 2020

Related U.S. Application Data

(60) Provisional application No. 62/507,699, filed on May 17, 2017.

(51) Int. Cl.
*A61F 13/00* (2024.01)
*A61B 5/00* (2006.01)
(Continued)

(52) U.S. Cl.
CPC .... *A61F 13/00063* (2013.01); *A61B 5/14507* (2013.01); *A61B 5/14532* (2013.01);
(Continued)

(58) Field of Classification Search
CPC ............. A61B 5/0077; A61B 5/14507; A61B 5/14532; A61B 5/14539; A61B 5/14546;
(Continued)

(56) References Cited

U.S. PATENT DOCUMENTS

| 4,813,942 A | 3/1989 | Alvarez |
| 5,407,685 A * | 4/1995 | Malchesky ............... A61L 2/26 424/404 |

(Continued)

FOREIGN PATENT DOCUMENTS

| CA | 2895625 | 4/2015 |
| CA | 2937579 | 7/2015 |

(Continued)

OTHER PUBLICATIONS

European Search Report dated Feb. 5, 2021 issued in respect of corresponding European patent application No. 18802056.4.
(Continued)

*Primary Examiner* — Shefali D Patel
(74) *Attorney, Agent, or Firm* — Shin Hung; VanTek IP LLP

(57) ABSTRACT

A wound covering includes a flexible main body, and a sensor element incorporated into the main body. The sensor element includes a mesh formed from a plurality of fibers, and the sensor element is configured to undergo a change in appearance in response to a change in a parameter associated with wound exudate. The wound covering further includes a supply of therapeutic agent configured to diffuse the therapeutic agent from the wound covering into a wound when the wound covering is placed on the wound.

17 Claims, 32 Drawing Sheets

(51) Int. Cl.
| | |
|---|---|
| *A61B 5/145* | (2006.01) |
| *A61F 13/01* | (2024.01) |
| *A61F 13/0203* | (2024.01) |
| *A61F 13/0206* | (2024.01) |
| *A61M 35/00* | (2006.01) |
| *B29C 70/84* | (2006.01) |
| *B29K 105/00* | (2006.01) |
| *B29L 31/00* | (2006.01) |
| *B33Y 10/00* | (2015.01) |
| *B33Y 80/00* | (2015.01) |

(52) U.S. Cl.
CPC ...... *A61B 5/14539* (2013.01); *A61B 5/14546* (2013.01); *A61B 5/6802* (2013.01); *A61F 13/00055* (2013.01); *A61F 13/01017* (2024.01); *A61F 13/01029* (2024.01); *A61F 13/01038* (2024.01); *A61F 13/0206* (2013.01); *A61F 13/0213* (2013.01); *A61M 35/30* (2019.05); *A61B 5/0022* (2013.01); *A61B 5/0077* (2013.01); *A61F 2013/00089* (2013.01); *A61F 2013/00195* (2013.01); *A61F 2013/00285* (2013.01); *A61F 13/00995* (2013.01); *A61M 2202/0208* (2013.01); *A61M 2205/0227* (2013.01); *A61M 2205/33* (2013.01); *A61M 2205/3327* (2013.01); *B29C 70/84* (2013.01); *B29K 2005/00* (2013.01); *B29K 2105/0061* (2013.01); *B29L 2031/753* (2013.01); *B33Y 10/00* (2014.12); *B33Y 80/00* (2014.12)

(58) Field of Classification Search
CPC ............. A61B 5/6802; A61F 13/00055; A61F 13/00063; A61F 13/00995; A61F 13/01017; A61F 13/01029; A61F 13/01038; A61F 13/0206; A61F 13/0213; A61F 2013/00089; A61F 2013/00187; A61F 2013/00195; A61F 2013/00238; A61F 2013/00285; A61K 9/70; A61K 9/7007; A61L 15/44; A61L 15/56; A61L 15/60; A61L 26/0066; A61L 26/008; A61M 2202/0208; A61M 2205/0205; A61M 2205/0227; A61M 2205/33; A61M 2205/3324; A61M 2205/3327; A61M 2205/3368; A61M 2205/36; A61M 35/00; A61M 35/30; B29C 70/84; B29K 2105/0061; B29L 2031/753
See application file for complete search history.

(56) References Cited

U.S. PATENT DOCUMENTS

| | | | |
|---|---|---|---|
| 9,499,852 B2 | 11/2016 | Jenkins et al. | |
| 9,810,587 B2 | 11/2017 | Cranston et al. | |
| 2015/0111243 A1 | 4/2015 | Jenkins et al. | |

FOREIGN PATENT DOCUMENTS

| | | | | |
|---|---|---|---|---|
| EP | 2533740 B1 | 12/2012 | | |
| GB | 2408330 | 5/2005 | | |
| WO | WO-9306802 A1 * | 4/1993 | ....... | A61F 13/00008 |
| WO | WO 2011/098575 | 8/2011 | | |
| WO | 2012/074509 | 6/2012 | | |
| WO | 2014/188200 | 11/2014 | | |
| WO | 2016/128762 | 8/2016 | | |
| WO | WO 2017/195038 | 11/2017 | | |

OTHER PUBLICATIONS

Bagherifard et al., "Dermal Patch with Integrated Flexible Heater for on Demand Drug Delivery," *Advanced Healthcare Materials*, 2016, pp. 175-184.
Church et al., "Burn Wound Infections," *Clinical Microbiology Reviews*, Apr. 2006, pp. 403-434.
Dawes and Ribbons, "The Endogenous Metabolism of Microorganisms," *Annual Reviews Microbiology*, vol. 16, 1992, pp. 241-264.
Fuchs et al., "Anaerobic Gene Expression in *Staphylococcus aureus*," *Journal of Bacteriology*, vol. 189, No. 11, Jun. 2007, pp. 4275-4289.
Gethin, "The significance of surface pH in chronic wounds," *Wounds UK*, 2007, pp. 52-56.
Ghorbanian et al., "Microfluidic direct writer with integrated declogging mechanism for fabricating cell-laden hydrogel constructs," *Biomed. Microdevices*, 2014, pp. 387-395.
Kim et al., "Epidermal Electronics," *Science*, vol. 333, Aug. 2011, 8pps.
Koh et al., "A soft, wearable microfluidic device for the capture, storage, and colorimetric sensing of sweat," *Science Translational Medicine*, 2016, 14pps.
Liu et al., "Epidermal mechano-acoustic sensing electronics for cardiovascular diagnostics and human-machine interfaces," *Science Advances*, vol. 2, 2016, pp. 1-12.
Mavros et al., "Gentamicin collagen sponges for the prevention of sternal wound infection: A meta-analysis of randomized controlled trials," *The Journal of Thoracic and Cardiovascular Surgery*, vol. 144, No. 5, 2012, pp. 1235-1240.
Miller et al., "Rapid casting of patterned vascular networks for perfusable engineered 3D tissues," *Nat Mater.*, vol. 11, No. 9, Sep. 2012, pp. 768-774.
Mohammadi et al., "Skin Diseases Modeling using Combined Tissue Engineering and Microfluidic Technologies," *Advanced Healthcare Materials*, 2016, 23pps.
Mostafalu et al., "A toolkit of thread-based microfluidics, sensors, and electronics for 3D tissue embedding for medical diagnostics," *Microsystems & Nanoengineering*, 2016, 10pps.
Najafabadi et al., "Biodegradable nanofibrous polymeric substrates for generating elastic and flexible electronics," *Adv. Mater.*, vol. 26, No. 33, Sep. 2014, pp. 5823-5830.
Paul and Sharma, "Chitosan and Alginate Wound Dressings: A Short Review," *Trends Biomater. Artif. Organs*, vol. 18, No. 1, 2004, pp. 18-23.
Schneider et al., "Influence of pH on wound-healing: a new perspective for wound-therapy?" *Archives for Dematological Research*, 2007, pp. 413-420.
Seliktar, "Designing Cell-Compatible Hydrogels for Biomedical Applications," *Science*, 2012, pp. 1124-1128.
Sun and Tan, "Alginate-Based Biomaterials for Regenerative Medicine Applications," *Materials*, vol. 6, 2013, pp. 1285-1309.
Yetim et al., "Effect of Local Gentamicin Application on Healing and Wound Infection in Patients with Modified Radical Mastectomy: a Prospective Randomized Study," *The Journal of International Medical Research*, vol. 38, 2010, pp. 1442-1447.
Akbari et al., "Composite living fibers for creating tissue constructs using textile techniques," *Adv. Funct. Mater.*, 2014, pp. 4060-4067.
Bishop et al., "Importance of moisture balance at the wound-dressing interface," *J. Wound Care*, 2003, pp. 125-128.
Bloemsma et al., "Mortality and causes of death in a burn centre," *Burns*, 2008, pp. 1103-1107.
Chang et al., "Gentamicin-collagen implants to reduce surgical site infection: systematic review and meta-analysis of randomized trials," *Annals of Surg.*, 2013.
Chen et al., "Paper based platform for colorimetric sensing of dissolved NH 3 and CO2," *Biosens. Bioelectron.* 2015, pp. 477-484.
Corkhill et al., "Synthetic hydrogels VI. Hydrogel composites as wound dressings and implant materials," *Biomaterials*, 1989, pp. 3-10.
Dargaville, "Sensors and imaging for wound healing: A review," *Biosens. Bioelectron.*, 2013, pp. 30-42.
Davidson, "Current concepts in wound management and wound healing products," *Vet. Clin. North Am. Small Anim. Pract.*, 2015, pp. 537-564.

(56) References Cited

OTHER PUBLICATIONS

Huang et al., "Stretchable, wireless sensors and functional substrates for epidermal characterization of sweat," *Small*, 2014, pp. 3083-3090.

Jain et al., "Alginate drug delivery systems: application in context of pharmaceutical and biomedical research," *Drug Dev. Ind. Pharm.*, 2014, pp. 1576-1584.

Junker et al., "Topical delivery of ultrahigh concentrations of gentamicin is highly effective in reducing bacterial levels in infected porcine full-thickness wounds," *Plast. Reconstr. Surg.*, 2015, pp. 151-159.

Lavorgna et al., "Study of the combined effect of both clay and glycerol plasticizer on the properties of chitosan films," *Carbohydr. Polym.*, 2010, pp. 291-298.

Lee et al., "Alginate: properties and biomedical applications," *Prog. Polym. Sci.*, 2012, pp. 106-126.

Maral et al., "Effectiveness of human amnion preserved long-term in glycerol as a temporary biological dressing," *Burns*, 1999, pp. 625-635.

Murakami et al., "Hydrogel blends of chitin/chitosan, fucoidan and alginate as healing-impaired wound dressings," *Biomaterials*, 2010, pp. 83-90.

Okan et al., "The role of moisture balance in wound healing," *Adv. Skin Wound Care*, 2007, pp. 39-53.

Pedde et al., "Emerging Biofabrication Strategies for Engineering Complex Tissue Constructs," *Adv. Mater.*, 2017.

Queen et al., "The preclinical evaluation of the water vapour transmission rate through burn wound dressings," *Biomaterials*, 1987, pp. 367-371.

Tredget et al., "Pseudomonas infections in the thermally injured patient," *Burns*, 2004, pp. 3-26.

Yang et al., Cytotoxicity and wound healing properties of PVA/ws-chitosan/glycerol hydrogels made by irradiation followed by freeze-thawing, *Radiat. Phys. Chem.*, 2010, pp. 606-611.

Bagherifard et al., "Hydrogel Based Dermal Patch With Integrated Flexible Electronics for On-Demand Drug Delivery," *18th International Conference on Miniaturized Systems for Chemistry and Life Sciences*, Oct. 26-30, 2014 (2 pps).

International Search Report and Written Opinion issued in corresponding PCT Patent Application No. PCT/IB2018/053491, mailed Aug. 14, 2018 (10 pps.).

* cited by examiner

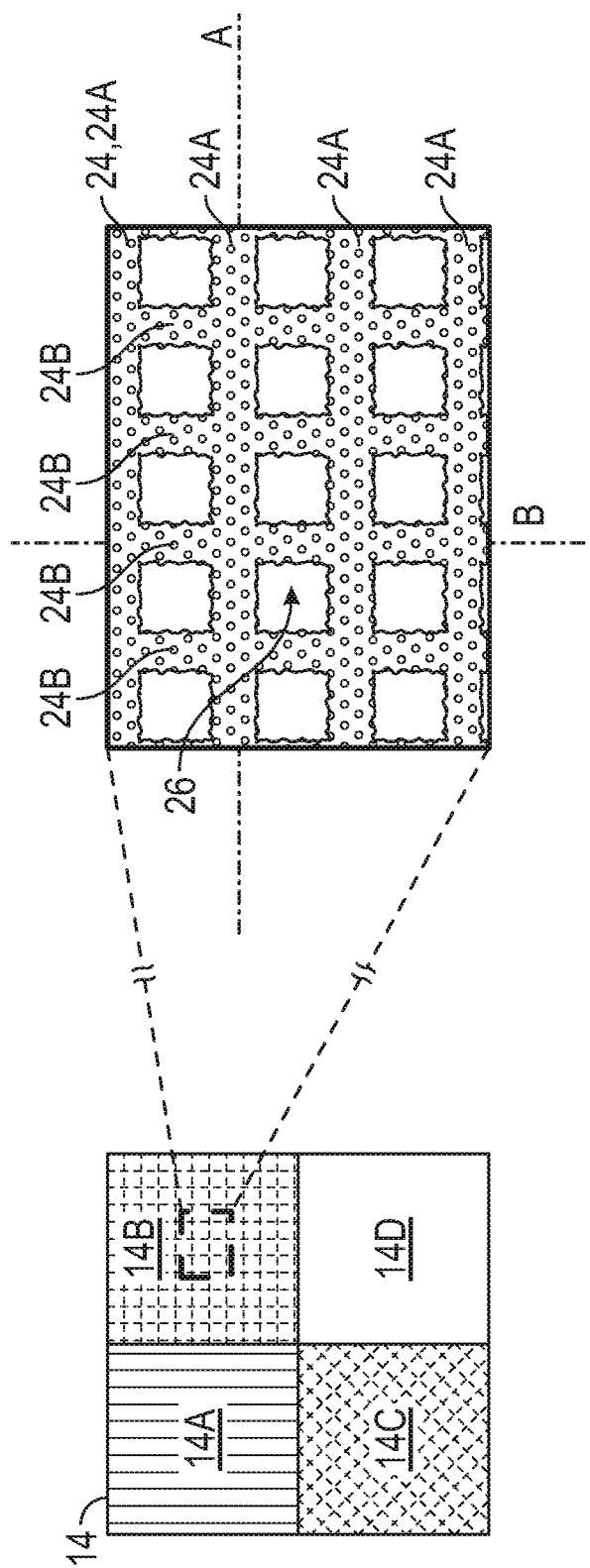

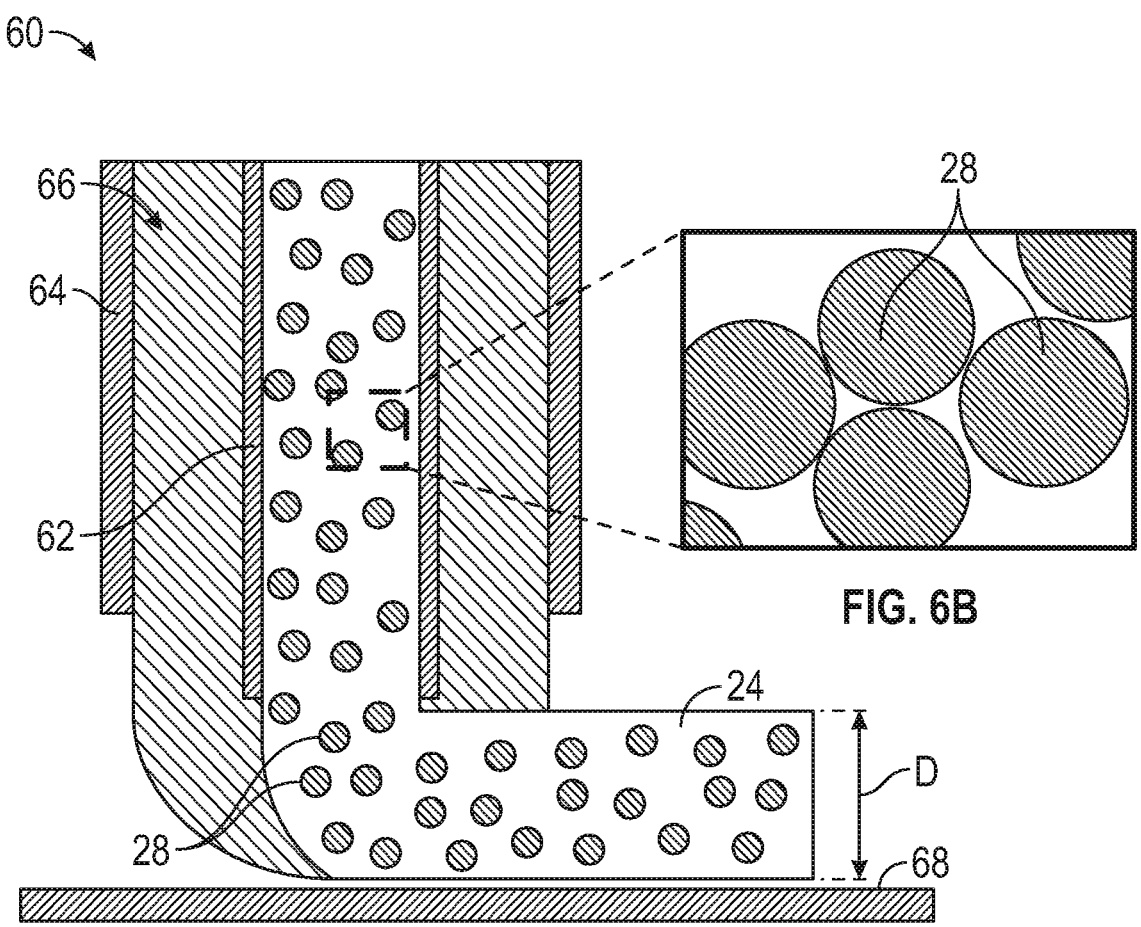
FIG. 6B
FIG. 6A
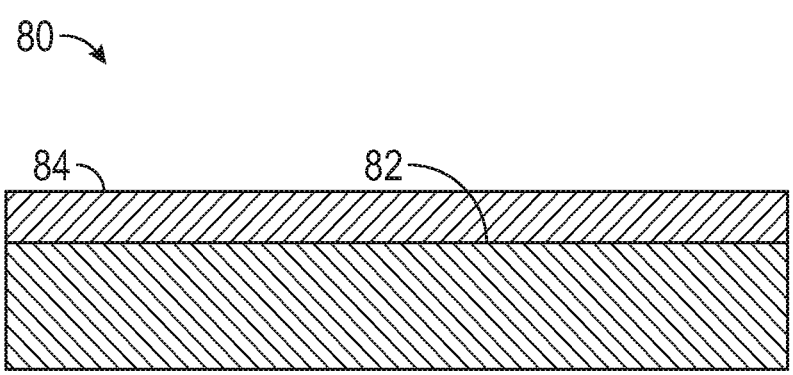
FIG. 7

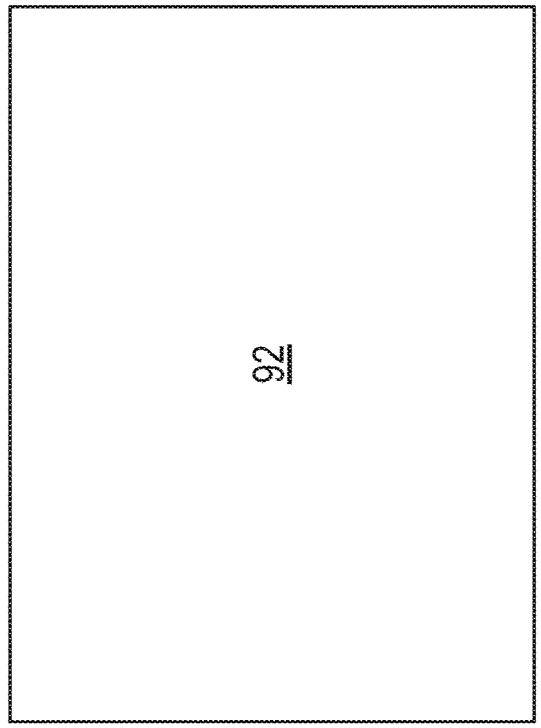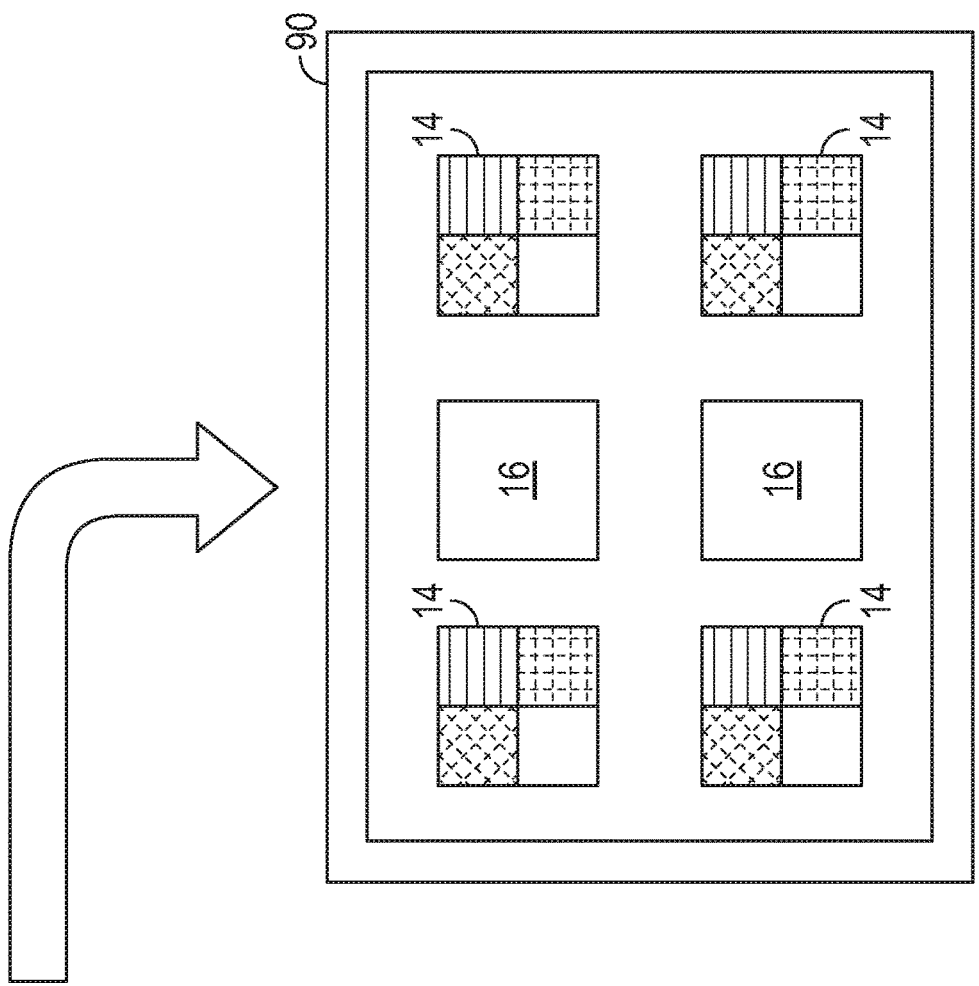
FIG. 15

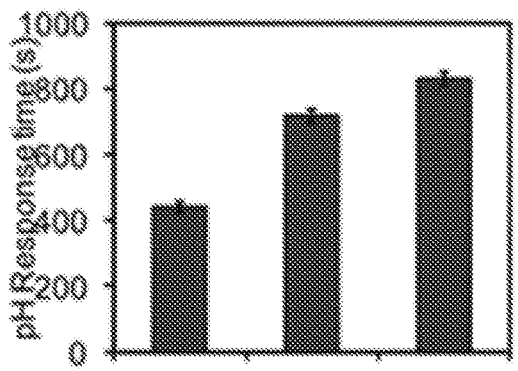
FIG. 18K
FIG. 19A
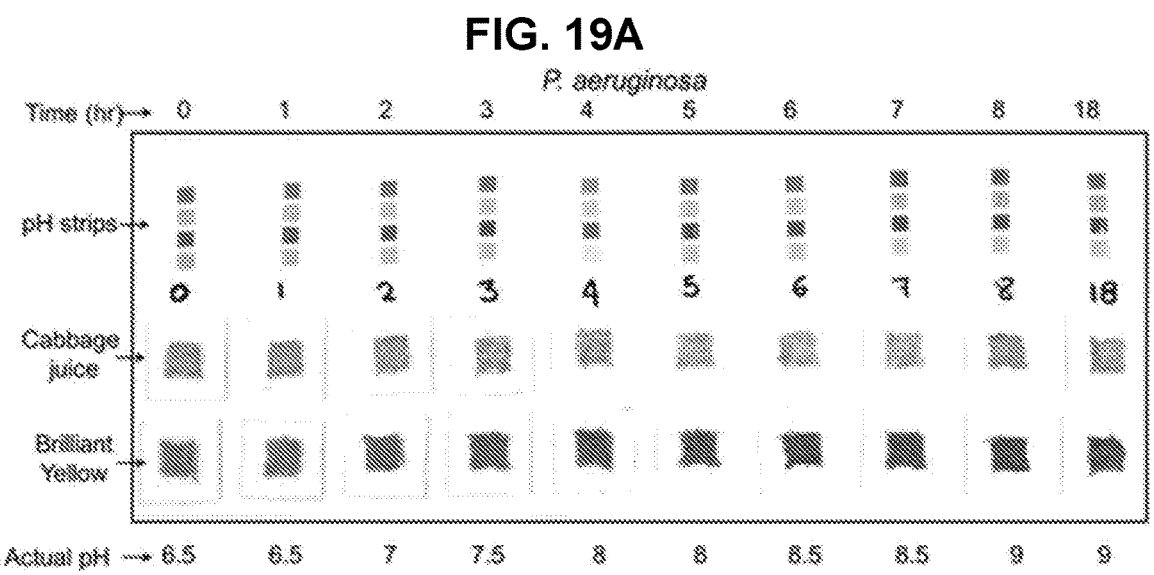
FIG. 19B
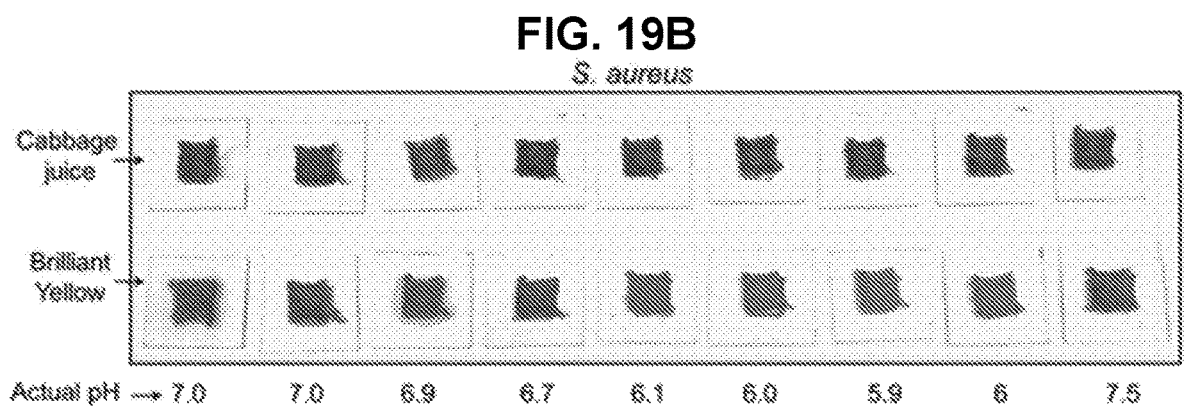

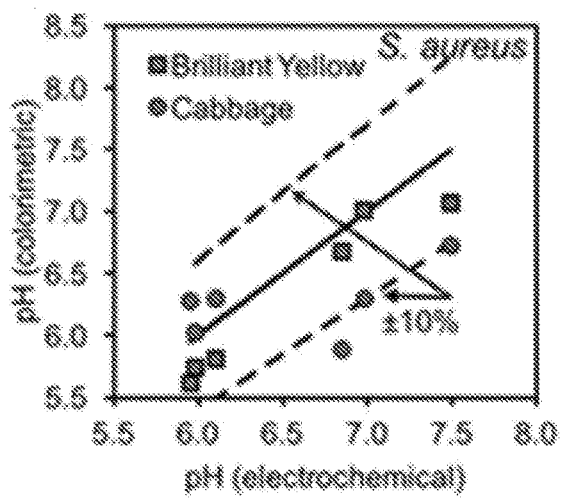
FIG. 19G
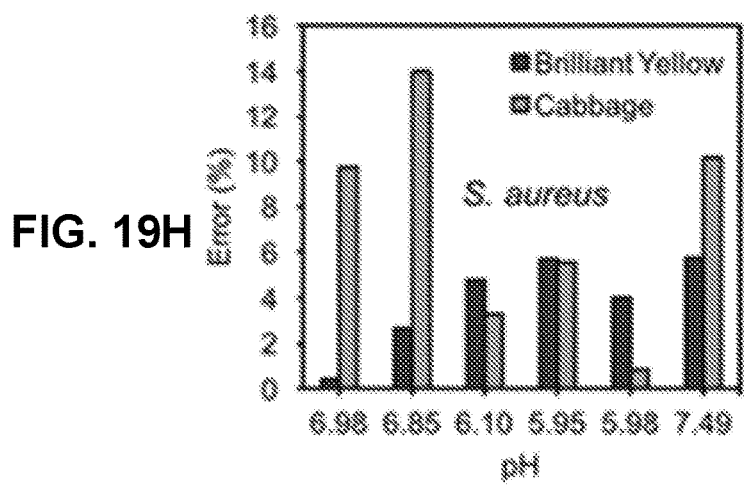
FIG. 19H
FIG. 20A
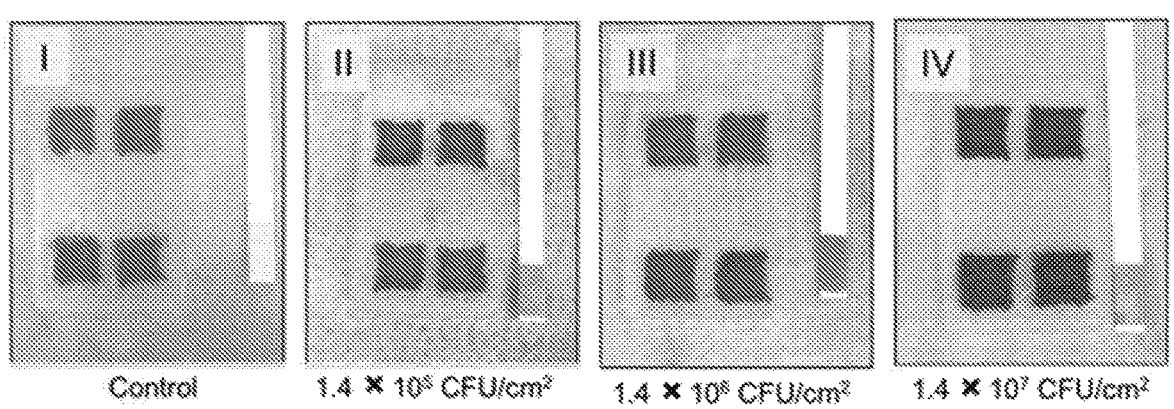

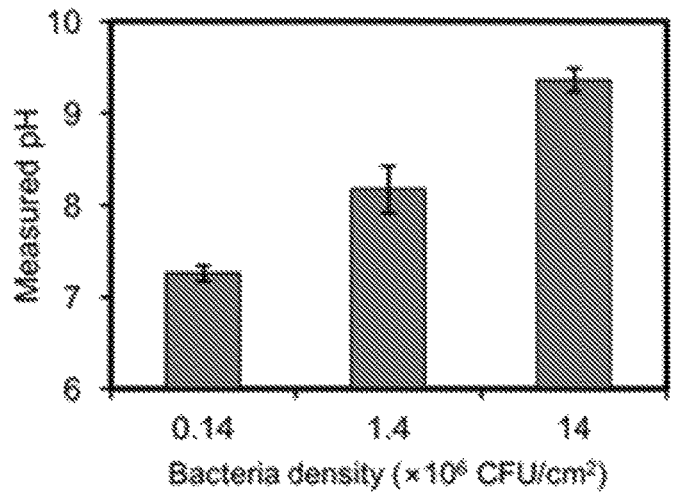
FIG. 20B
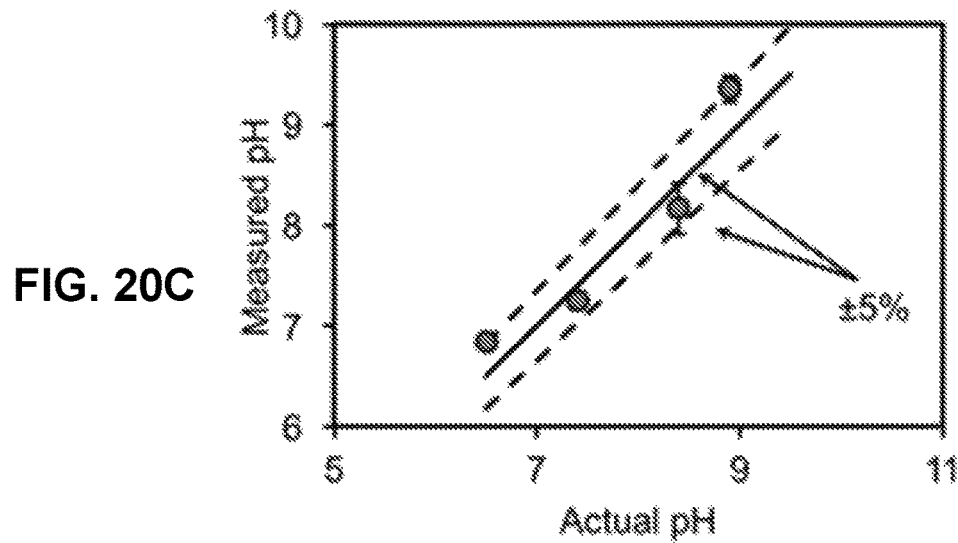
FIG. 20C
FIG. 20D    FIG. 20E    FIG. 20F
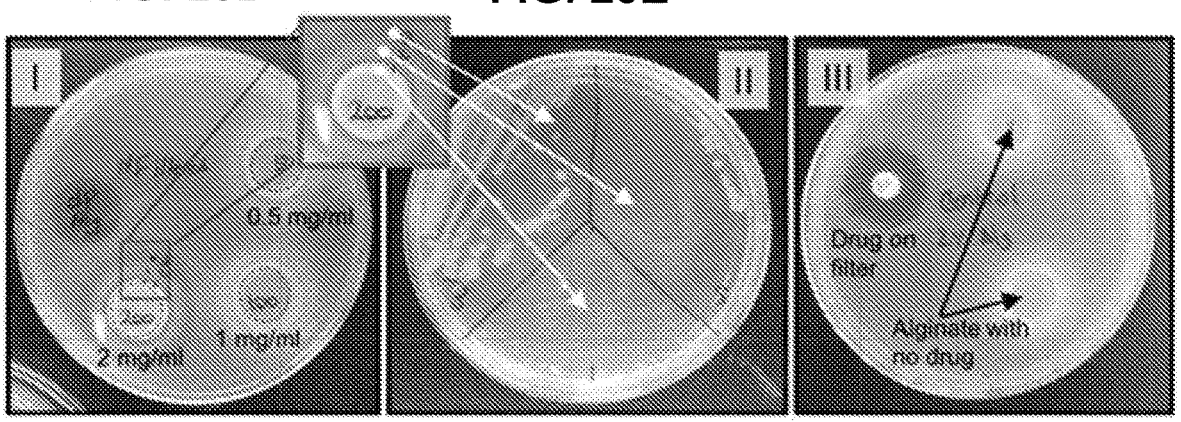

Reference color markers

FIG. 21E
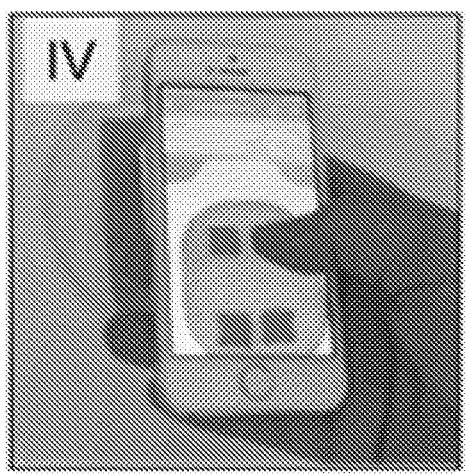
FIG. 21F
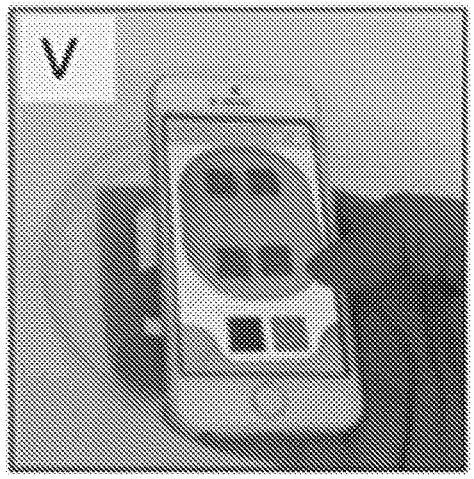
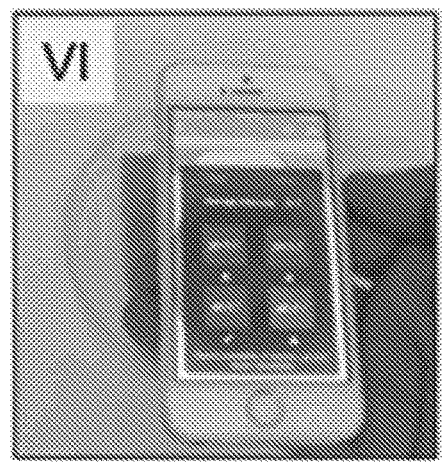
FIG. 21G
FIG. 21H
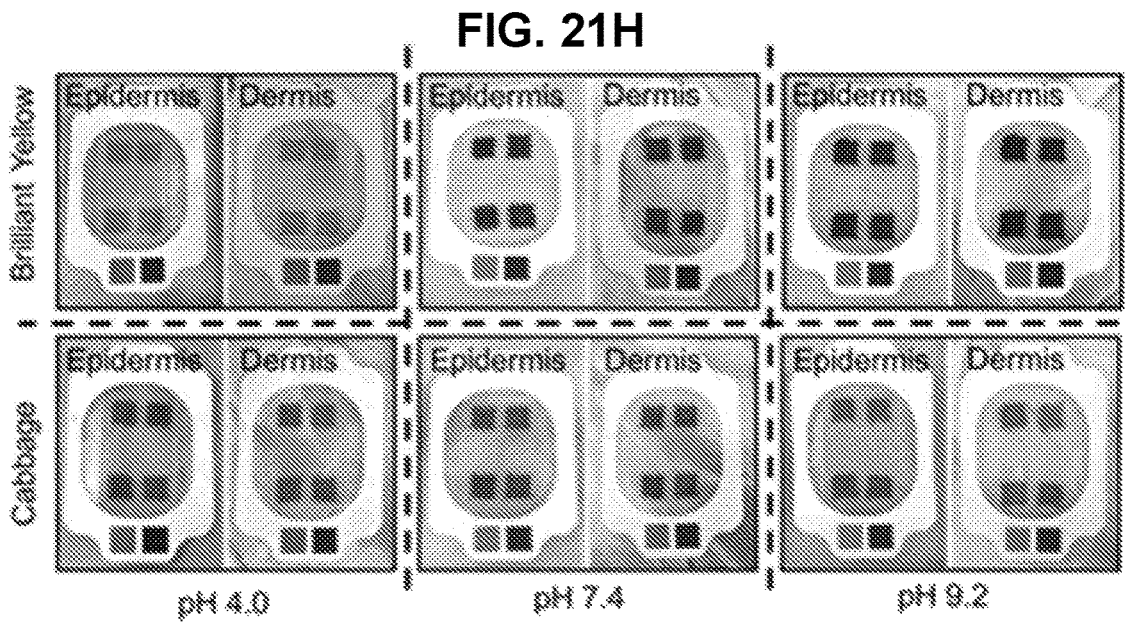

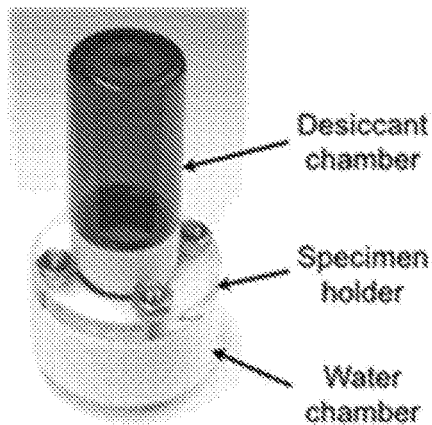
FIG. 26C
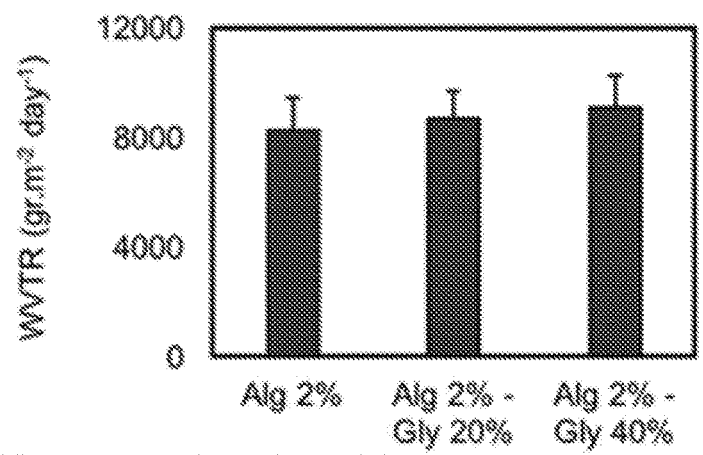
FIG. 26D
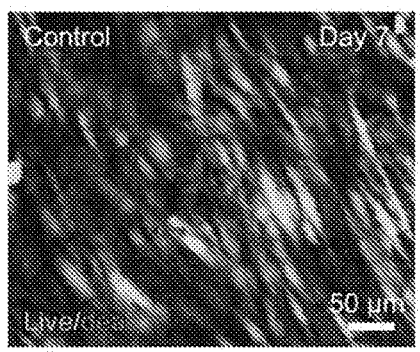 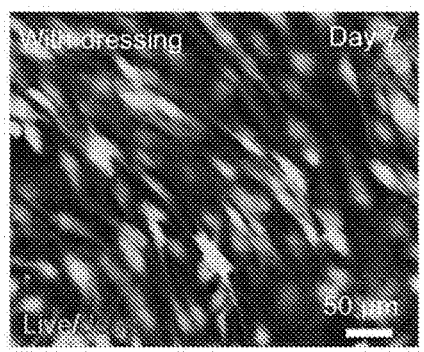
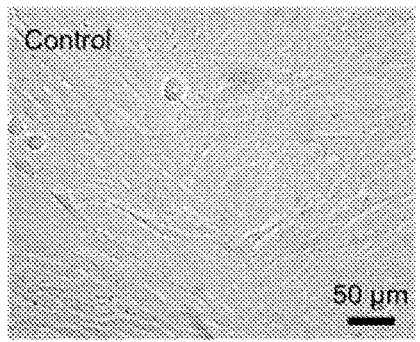 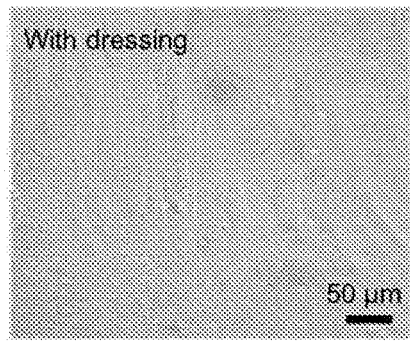
FIG. 27

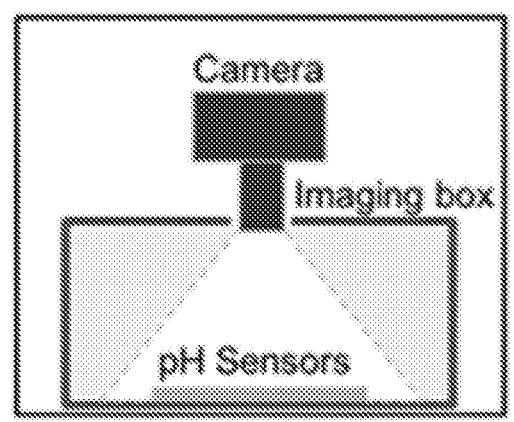
FIG. 28A
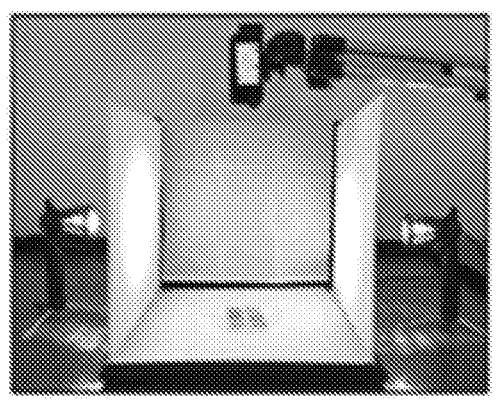
FIG. 28B
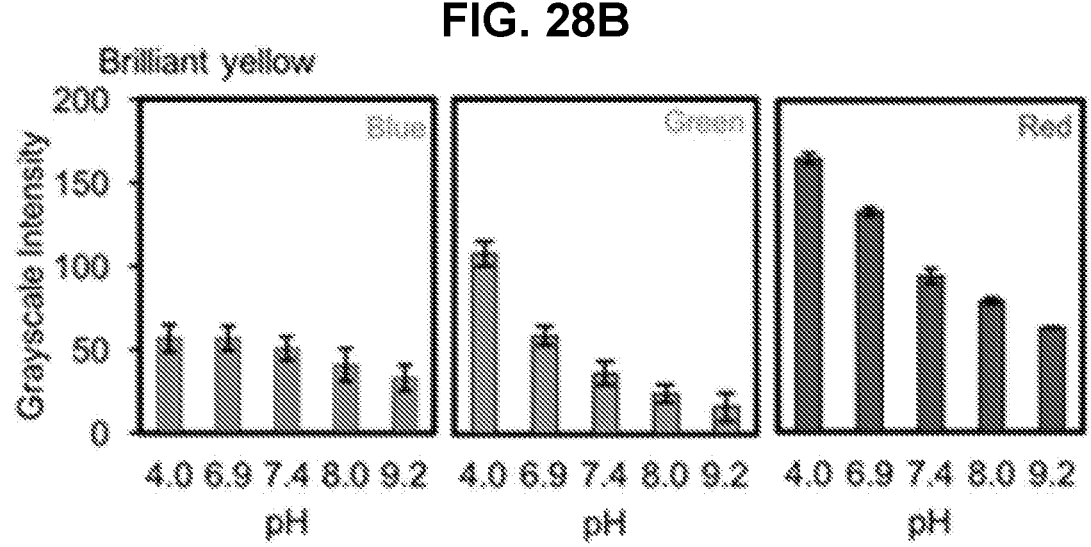

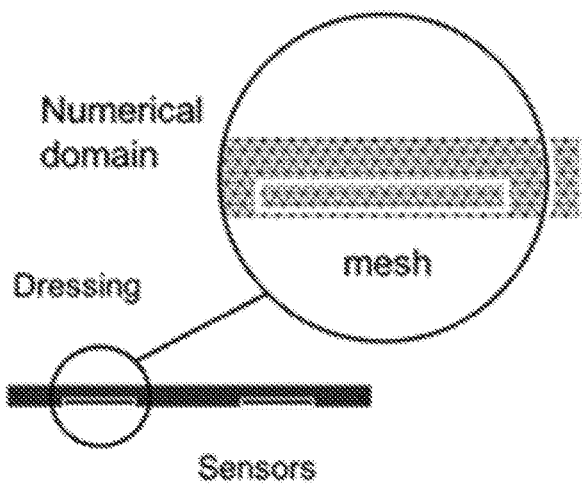
FIG. 30A
FIG. 30B
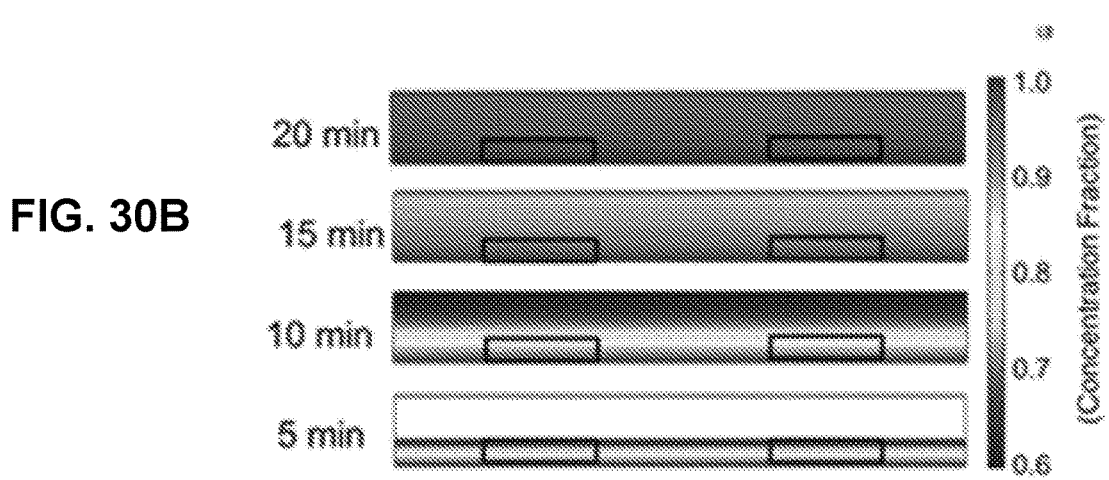
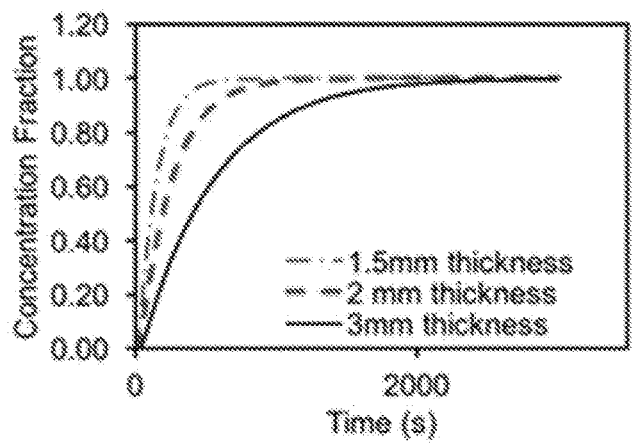
FIG. 30C

WOUND COVERING FOR WOUND MONITORING AND THERAPEUTIC AGENT DELIVERY

CROSS REFERENCE TO RELATED APPLICATIONS

This is the U.S. National Stage of International Application No. PCT/IB2018/053491, filed May 17, 2018, which was published in English under PCT Article 21 (2), which in turn claims the benefit of U.S. Provisional Application No. 62/507,699, filed May 17, 2017. The disclosures of International Application No. PCT/IB2018/053491 and U.S. Provisional Application No. 62/507,699 are incorporated herein by reference in their entirety.

FIELD

The present disclosure relates to wound coverings including sensing elements and therapeutic agent delivery elements for determining the presence of and treating infection.

BACKGROUND

Skin is the largest organ in the body and it regulates body temperature, protects internal organs against external physical and chemical substances, and provides a physical barrier against pathogens and microorganisms. Skin injuries caused by trauma, surgery, or diabetes have a high prevalence, and they represent a significant burden to patients and the healthcare system. Skin damage is painful and can catastrophically compromise the integrity and protective functions of the skin and establish an active portal for infections. The latter is a major clinical challenge as wound infections result in significantly longer hospitalization, delayed wound healing, and increased cost and mortality. Furthermore, an infection can lead to the development of a pronounced immune response, accompanied by sepsis or septic shock, which results in hypotension and multiorgan failure. Therefore, the prevention and management of infections, accompanied by continuous monitoring of the wound, are primary concerns of patients dealing with non-healing or traumatic injuries.

Current treatment strategies aim to alleviate pain following trauma, protect the wound from pathogenic infections, maintain the moisture of the wound, manage exudates, and provide an environment that promotes the healing process. Depending on the extent of the injury, traditional dressings such as gauzes, cotton wools, dressings that deliver bioactive constitutes, and antimicrobial and regenerative agents are being used in clinical practice. Commercially available dressings with regenerative capabilities include acellular grafts such as Alloderm Select™ (LifeCell Corporation), GraftJacket® (Wright Medical Technology, Inc.), Integra® (Integra Lifesciences Corp.), and Biobrane® (Bertek Pharmaceuticals Inc.) as well as cellular grafts such as Dermagraft® (Organogenesis, Inc.), Epicel® (Vericel Corporation), and Recell® (Avita Medical Ltd.). Silver-impregnated dressings are extensively used to prevent infections in the wound; some commercial examples are Acticoat™ (Smith & Nephew plc), Fibracol™ (Johnson & Johnson Corporation), and Silvasorb (Medline Industries, Inc.). However, there are several major challenges associated with implementing current dressings for wound management. First, it is almost impossible to detect pathogenic infections before clinical signs and symptoms arise. Second, the uncontrolled release of antimicrobial agents can lead to antibiotic resistance or delayed healing. Additionally, changing the dressing daily for visual inspections of the wound can be cumbersome and painful. Therefore, there is a pressing need to develop multifunctional dressings that are capable of monitoring wound conditions and providing proper treatment when necessary.

With the advent of flexible electronics and development of novel biomaterials, several advanced dressings have emerged that can measure the physicochemical properties of the acute and chronic wounds. Kim et al. developed flexible electronic systems that possessed elasticity and bending stiffness that was similar to the epidermis (5). These electronic devices were able to conform to the irregular structure of the skin and measure temperature and strain on the skin. In another study, Huang et al. fabricated stretchable sensors that could be mounted on various elastomeric substrates including cellulose paper, polyurethane, and silicon for epidermal analysis of biofluids (6). This device could quantify skin pH from sweat, then transfer data wirelessly to an external device. Najafabadi et al. fabricated electrical circuits on biodegradable nanofibrous polymeric substrates composed of a blend of poly(caprolactone) and poly(glycerol sebacate) (7). Temperature and strain sensors, as well as heating coils, were fabricated and characterized on this substrate. They demonstrated the ability to transfer the sensor readings and to control the heater wirelessly. Liu and coworkers developed flexible mechano-acoustic sensing electronics for epidermal measurement of cardiovascular diagnostics markers (8). In a recent study, Mustafalu et al. developed a thread-based electronic system with the ability to measure physicochemical properties of tissues (9). They used this technology to measure strain, temperature, pH, and glucose in biological samples. Despite being successfully implemented for epidermal applications, these electronics-based technologies face challenges that compromise their sensitivity because of the proteins, chemokines, and electrolytes that exist in wound exudates and sweat (10). Moreover, electrical/electrochemical systems require the integration of electronic circuitry and a power source for analysis of their readout, complicating the device design and fabrication. These technologies have also not been combined with drug-releasing capabilities to deliver antimicrobial agents directly to the site of injury. Accordingly, a need exists for improved wound coverings.

SUMMARY

Certain embodiments of the disclosure concern wound coverings including sensor elements configured to monitor certain parameters of wound exudate and therapeutic agent delivery elements configured to supply therapeutic agent to the wound. In a representative embodiment, a wound covering comprises a flexible main body, and a sensor element incorporated into the main body. The sensor element comprises a mesh formed from a plurality of fibers, and is configured to undergo a change in appearance in response to a change in a parameter associated with wound exudate. The wound covering further comprises a supply of therapeutic agent configured to diffuse therapeutic agent from the wound covering into a wound when the wound covering is placed on a wound.

In some embodiments, the fibers comprise a plurality of sensor particles, and the sensor particles comprise one or more indicator compounds configured to undergo a detectable change in appearance in response to a change in a parameter associated with wound exudate.

In some embodiments, the fibers comprise a hydrogel, and the sensor particles comprise beads comprising an ion-exchange resin or a hydrogel.

In some embodiments, the one or more indicator compounds include pH-sensitive dye, glucose-sensitive dye, lactate-sensitive dye, or any combination thereof.

In some embodiments, the sensor element comprises a first region, a second region, a third region, and a fourth region, and the sensor particles in the fibers of the first region comprise pH-sensitive dye, the sensor particles in the fibers of the second region comprise glucose-sensitive dye, the sensor particles in the fibers of the third region comprise lactate-sensitive dye, and the sensor particles in the fibers of the fourth region are dye-free.

In some embodiments, the sensor element is incorporated into the main body such that a lower surface of the sensor element forms part of a lower surface of the main body.

In some embodiments, the wound covering further comprises a first layer comprising a hydrogel, and a second layer disposed on the first layer. The second layer comprises a porous hydrophobic material. The sensor element can be at least partially incorporated into the first layer.

In some embodiments, the wound covering further comprises a third layer disposed on the first layer on the opposite side of the first layer from the second layer such that the first layer is between the third layer and the second layer, and the third layer is configured to inhibit bacteria growth.

In some embodiments, the supply of therapeutic agent is incorporated into the hydrogel of the first layer.

In some embodiments, the wound covering further comprises a therapeutic agent delivery element, the supply of therapeutic agent is incorporated into the delivery element.

In some embodiments, the delivery element comprises a mesh formed from a plurality of fibers comprising a hydrogel, and the therapeutic agent is incorporated into the hydrogel.

In some embodiments, the delivery element comprises a mesh formed from a plurality of fibers comprising a hydrogel, and the fibers comprise a plurality of porous hydrogel particles comprising the therapeutic agent. The porous hydrogel particles are configured to release the therapeutic agent when a parameter exceeds a predetermined threshold.

In some embodiments, the parameter comprises pH of wound exudate or a temperature of the porous hydrogel particles.

In some embodiments, the wound covering further comprises a heating element configured to selectively heat the delivery element.

In some embodiments, the therapeutic agent comprises an antibiotic agent, a cellular growth-promoting agent, or any combination thereof.

In some embodiments, the wound covering further comprises a humidity sensor element incorporated into the main body. The humidity sensor element can comprise a substrate having a coating configured to undergo a change in appearance in response to a change in humidity.

In some embodiments, the wound covering further comprises a plurality of particles configured to release oxygen into a wound when the covering is placed on a wound.

In some embodiments, a method of using the wound covering comprises applying the wound covering to a wound, and detecting a change in appearance of the sensor element.

In some embodiments, detecting a change in appearance of the sensor element further comprises producing image data of the sensor element, the image data comprising data of a color of the sensor element, and comparing the data of the color of the sensor element to predetermined color data of the sensor element to determine a value of a parameter associated with exudate from the wound. The method further comprises removing the wound covering from the wound if the value of the parameter associated with wound exudate indicates the presence of infection in the wound.

In another representative embodiment, a method of making a wound covering comprises incorporating a sensor element into a flexible main body of the wound covering, the sensor element comprising a mesh formed from a plurality of fibers and being configured to undergo a change in appearance in response to a change in a parameter associated with wound exudate. The method further comprises incorporating a supply of therapeutic agent into the wound covering such that the therapeutic agent selectively diffuses from the wound covering into a wound when the wound covering is placed on a wound.

In some embodiments, the method further comprises forming the sensor element by forming a mesh comprising a plurality of hydrogel fibers, the hydrogel fibers comprising a plurality of sensor particles, the sensor particles comprising one or more indicator compounds configured to undergo a change in appearance in response to a change in a parameter associated with wound exudate.

In some embodiments, incorporating a supply of therapeutic agent into the wound covering further comprises forming a mesh comprising a plurality of hydrogel fibers, the hydrogel fibers comprising a plurality of particles comprising the therapeutic agent, the particles being configured to release the therapeutic agent when a pH parameter or a temperature parameter exceeds a predetermined threshold.

In some embodiments, incorporating the sensor element into the main body further comprises situating the sensor element in a mold, incorporating the supply of therapeutic agent further comprises situating a therapeutic agent delivery element in the mold, and the method further comprises adding an uncrosslinked hydrogel material to the mold and adding a crosslinking agent to crosslink the uncrosslinked hydrogel material to form the main body.

The foregoing and other objects, features, and advantages of the disclosed technology will become more apparent from the following detailed description, which proceeds with reference to the accompanying figures.

BRIEF DESCRIPTION OF THE DRAWINGS

FIG. 4 is a top plan view of a representative embodiment of a sensor element.

FIG. 5 is a magnified view of a portion of the sensor element of FIG. 4 illustrating the constituent fiber mesh of the sensor element.

FIG. 6A is a cross-sectional side elevation view of a microextruder apparatus illustrating fabrication of a hydrogel fiber containing a plurality of sensor particles.

FIG. 6B is a magnified view of the hydrogel fiber of FIG. 6A illustrating the sensor particles in the hydrogel fiber.

FIG. 7 is a cross-sectional side elevation view of a humidity sensor element, according to one embodiment.

FIG. 15 is a top plan view illustrating a method of fabricating the wound covering of FIG. 1 in a mold, according to one embodiment.

FIGS. 18F-18K are bar charts illustrating the response time of sensor elements comprising Brilliant Yellow and cabbage juice versus, alginate concentration, porosity, fiber diameter, alginate concentration, dressing thickness, and glycerol content.

FIGS. 19A and 19B illustrate measurement of pH variations with culture time for *P. aeruginosa* and *S. aureus* bacteria using pH strips and embodiments of the sensor elements described herein.

FIGS. 19C-19H are graphs and bar charts illustrating pH measurements with the sensor elements described herein as compared to pH values measured by a pH probe for *P. aeruginosa* and *S. aureus* cultures.

FIG. 20A illustrates the color changes of sensor elements on representative embodiments of the wound coverings described herein after placement on pig skins including various bacterial cultures.

FIG. 20B is a bar chart illustrating pH values of infected pig skin measured using a smartphone and the wound coverings described herein.

FIG. 20C is a graph illustrating the pH as determined from the wound coverings described herein compared to the pH as measured by a probe.

FIGS. 20D-20F illustrate placement of drug-eluting hydrogel disks on petri dishes containing bacterial cultures.

FIGS. 21A-21H illustrate use of a smartphone to produce image data of the sensor elements of a wound covering.

FIG. 26C is a perspective view of a representative embodiment of a desiccant apparatus.

FIG. 26D is a bar chart illustrating the water vapor transmission rate of different alginate and glycerol hydrogel formulations.

FIG. 27 illustrates a live/dead assay for fibroblasts cultured on dermal patches with Brilliant Yellow pH sensors in acidic and alkaline conditions to assess cytotoxicity.

FIG. 28A illustrates an apparatus for acquiring images of wound coverings including a camera and an image box.

FIGS. 28B-28C are bar charts illustrating grayscale intensity in the blue, green, and red channels of the sensor elements described herein including Brilliant Yellow dye and cabbage juice at various pH values.

FIG. 30A illustrates a finite element analysis mesh of a representative embodiment of a wound covering including sensor elements.

FIG. 30B illustrates variation in the concentration fraction distribution of $H^+$ ions in the wound covering as a function of time as determined using the FEA mesh of FIG. 30A.

FIG. 30C is a graph illustrating the concentration fraction of $H^+$ ions in the wound covering as a function of time.

DETAILED DESCRIPTION

Figure 1:
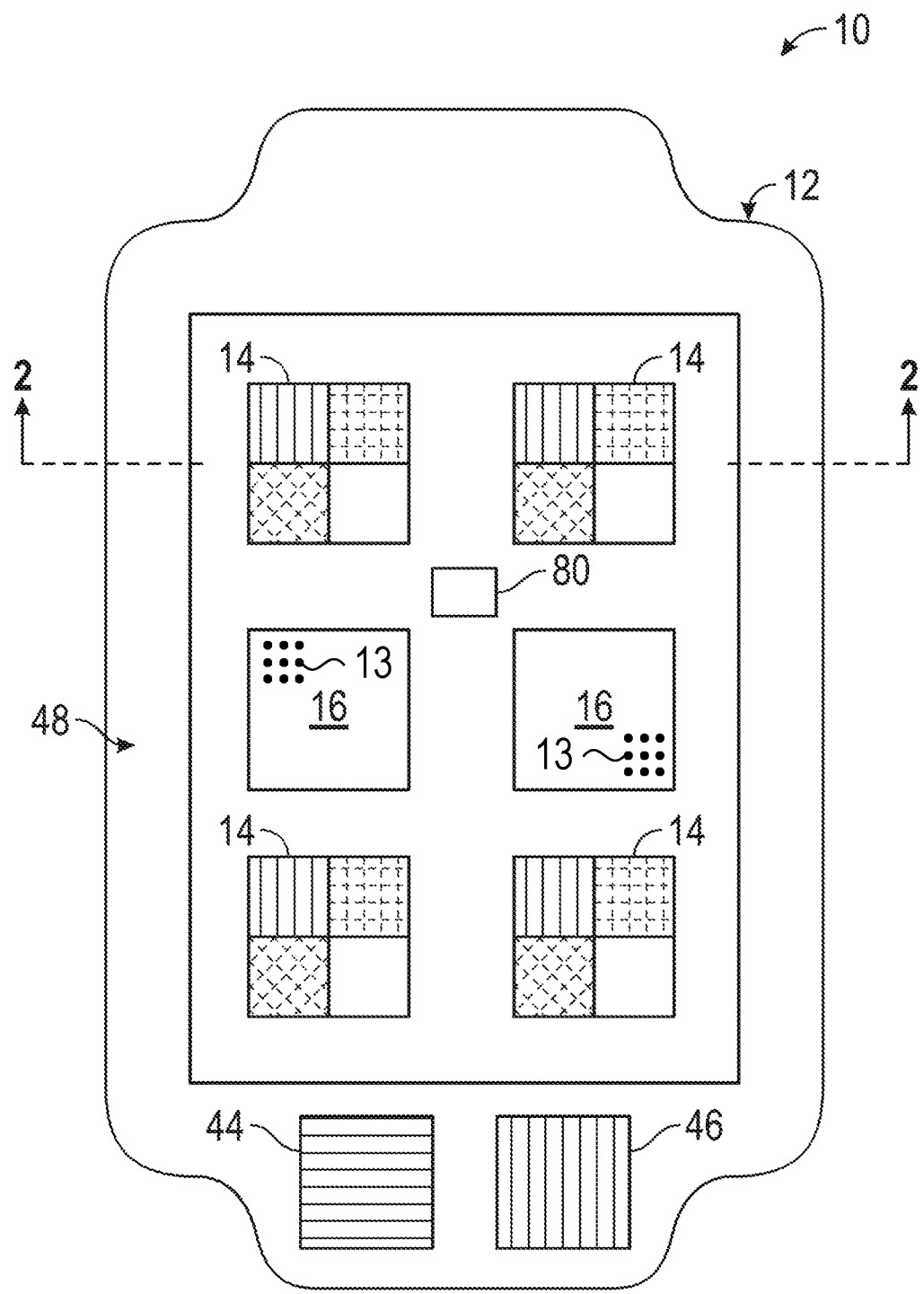
FIG. 1 is a top plan view of a wound covering including a plurality of sensor elements and therapeutic agent delivery elements, according to one embodiment.

The present disclosure pertains to multifunctional hydrogel-based wound dressings for wound monitoring and drug delivery. Some embodiments include a smart dermal patch or wound dressing that comprises a plurality of sensors (e.g., sensor arrays) and a plurality of drug-eluting scaffolds that are arranged and attached on a flexible substrate (e.g., a dressing body). In certain embodiments, the sensor arrays can be loaded with color-changing beads in order to detect spatial variations of biological markers including pH on the wound site. Colorimetric measurement of chemical biomarkers such as pH, lactate, glucose, pyocyanin (a toxin that is released by Gram negative bacterium *Pseudomonas aeruginosa*) and chloride can be one quantitative method for continuous monitoring of the wound environment using devices such as smartphones that can capture high-quality digital images. In certain embodiments, software can be used to record color changes in the sensors and convert them into quantitative data. Biomarkers that can be detected using colorimetric approaches can be loaded and used into the sensor arrays. The drug-eluting scaffolds can release doses of antibiotics, anti-fungal agents, etc., at the wound site to eradicate the bacteria or other infections that may remain on the wound site each time the dressing is replaced. The release mechanism can be continuous or triggered by changes in the wound environment (e.g., pH), or enzymes that are secreted by bacteria (e.g., enzyme-responsive peptides). The flexible substrate can provide conformal contact with the wound site.

Further, pH can be an important indicator of the wound condition, and can be correlated to angiogenesis, protease activity, and/or bacterial or fungal infection. The pH of human skin is typically slightly acidic and varies in the range of 4.0-6.0 (13). However, when the skin is breached in injuries, this acidic milieu is disturbed as the skin is exposed to internal body fluids that have a neutral pH (pH=7.4). Releasing antibiotics at the wound site sterilizes the wound after the dressing is placed on the injury. The proposed engineered dressing offers several advantages over existing technologies including the ability to (1) map the pH of the wound using an array of printed sensors, (2) deliver antibacterial agents at the wound site, which prevents adverse side effects of systemic drug delivery, (3) maintain the wound moisture using a hydrogel substrate, and (4) provide conformal coverage to the wound area. Additionally, the dressing can be integrated within commercially-available patches and can be placed on the wound without chemical or physical irritation. Functional characteristics of this patch in terms of its response time to different pH environments, drug release kinetics, and the ability to maintain a conformal contact with the wound curvature are studied to optimize the patch specifications. Three-dimensional printing can be employed to fabricate pH-responsive components with meshed structure and therefore high surface-to-volume area ratio, enabling a fast detection of pH changes. The pH level of the wound site can be determined by processing the photographs of the pH sensors that made contact with the wound site. Color intensities associated with the color changes on the pH sensors can be converted to grayscale intensities. In certain embodiments, the pH level of the wound site can be derived from these grayscale intensities using calibration curves.

Colorimetric measurement of chemical biomarkers such as pH is one approach that offers a quantitative method for continuous monitoring of the wound environment using devices such as smartphones that can capture high-quality digital images (11). The multifunctional hydrogel-based dressing embodiments described herein are capable of colorimetric measurement of pH as an indicator of bacterial infection, and releasing antibiotics to wound site (FIG. 1A). pH is an important indicator of the wound condition and can be correlated to angiogenesis, protease activity, and bacterial infection (12, 13). The pH of the skin is slightly acidic and varies in the range of 4.0-6.0 (13). However, when the skin is breached in injuries, this acidic milieu is disturbed as the skin is exposed to internal body fluids that have a neutral pH (pH=7.4) (13). Releasing antibiotics at the wound site sterilizes the wound after the dressing is placed on the injury. The disclosed engineered dressing embodiments offer several advantages over existing technologies including the ability to (1) map the pH of the wound using an array of printed sensors, (2) deliver antibacterial agents at the wound site, which prevents adverse side effects of systemic drug delivery, (3) maintain the wound moisture using a hydrogel substrate, and (4) provide conformal coverage to the wound area. Additionally, the dressing can be integrated within commercially-available patches and can be placed on the wound without chemical or physical irritation.

FIG. 1 illustrates a multifunctional, low-adherent wound dressing or covering 10, according to one embodiment. The wound covering 10 can comprise a main body 12 including a plurality of sensor elements 14 incorporated (e.g., embedded or partially embedded) into and arrayed in various locations around the main body 12. The wound covering 10 can also include one or more therapeutic agent delivery elements 16 incorporated into and arrayed in various locations around the main body 12. The wound covering 10 can be resilient and flexible, and configured to be placed over and at least partially cover a wound while conforming to the shape of the body at that location.

Figure 2:
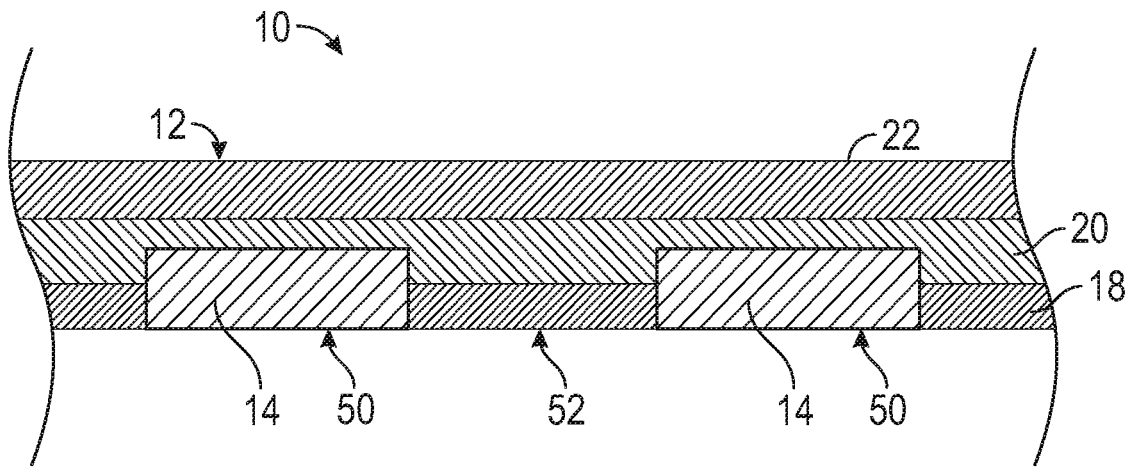
FIG. 2 is a cross-sectional view of the wound covering of FIG. 1 taken along line 2-2 of FIG. 1.

In certain embodiments, the main body 12 can include one or more layers. For example, FIG. 2 is a cross-sectional view of a representative embodiment of the main body 12 including a first layer 18, a second layer 20, and a third layer 22 arranged such that the second layer 20 is disposed between the first and third layers 18 and 22. In certain embodiments, the first layer 18 can be a relatively thin, flexible, and/or low-adherent membrane. The membrane 18 can be a liquid-, gas-, and/or ion-permeable membrane. For example, in some embodiments the first layer 18 can be water-permeable, and configured to allow wound exudate and/or analytes dissolved therein to diffuse through the first layer 18 and into the main body 12. The first layer 18 can also be configured to allow therapeutic agents contained in the main body 12 to diffuse through the first layer and into a wound. In certain embodiments, the first layer 18 can comprise a material having antimicrobial properties. For example, the material from which the first layer 18 is made can have antimicrobial properties, and/or the first layer 18 can comprise one or more antimicrobial coatings. In particular embodiments, the first layer 18 can comprise one or more materials including Chitosan, poly(ethylene glycol), poly(sulfobetaine methacrylate), poly(2-methyl-2oxazoline), polyphenols, albumin, whey, or combinations thereof. In certain embodiments, the first layer 18 can have a thickness of from 1 μm to 100 μm, 1 μm to 50 μm, or 1 μm to 10 μm.

In certain embodiments, the second layer 20 can comprise a flexible, natural or synthetic membrane. In particular embodiments, the second layer 20 can be a liquid and/or gas permeable membrane made from a hydrophilic polymeric material, such as a hydrogel. As used herein, the term "hydrogel" refers to a colloidal system comprising a solid three-dimensional network of polymer chains within an aqueous liquid, such as liquid water. In certain examples, a hydrogel can be primarily liquid, but can behave like a solid due to a three-dimensional network of entangled and/or crosslinked molecules of a solid within the liquid. In certain examples, the solid can be a hydrophilic material. As used herein, the term "hydrophilic material" refers to a material wherein a water droplet on a surface of the material forms a contact angle of less than 90°. Exemplary hydrogel materials that can be used to make the second layer 20 include polysaccharides such as alginate, agarose, Chitosan, or natural or synthetic proteins such as collagen, gelatin, etc., or combinations thereof.

In particular embodiments, the second layer 20 can be doped with one or more therapeutic agents, such as liquid antimicrobial drugs or antibiotics including ciprofloxacin hydrochloride, gentamicin sulfate, streptomycin, penicillin, etc., hormones such as growth hormone-releasing hormone, tissue growth factors such as fibroblast growth factor, vascular endothelial growth factor, platelet-derived growth factor, epidermal growth factor, etc., nonsteroidal anti-inflammatory agents such as ibuprofen, naproxen, etc., pain-relieving agents such as opioids including morphine, codeine, etc., and/or cells such as human-induced pluripotent stem cells. The second layer 20 can be configured to allow the therapeutic agents to diffuse from the dressing 10 into a wound on which the dressing is placed, as described in greater detail below.

The third layer 22 can also comprise a flexible, natural or synthetic membrane, which can be configured as an outer layer. In certain embodiments, the third layer 22 can comprise a relatively thin layer of semi-permeable polymeric material, such as polyamide, silicone, silk, or combinations thereof. For example, in particular embodiments, the third layer 22 can comprise a porous wound dressing material such as Mepitel® available from Molnylcke AB of Goteborg, Sweden, or Tegaderm™ available from 3M. In certain embodiments, the third layer 22 can be made from a hydrophobic material. As used herein, the term "hydrophobic material" refers to a material wherein a water droplet on a surface of the material forms a contact angle of greater than 90°. In certain embodiments, the third layer 22 can be configured to inhibit moisture loss through the exterior surface of the main body 12 from the hydrogel layer(s) below.

In some embodiments, one or more of the layers can comprise a plasticizer such as glycerol to improve the flexibility of the covering 10 and allow the covering to be lyophilized for packaging and storage. For example, in particular embodiments the second layer 20 can comprise 2%-4% (w/v) alginate hydrogel with 20%-40% (w/v) glycerol. In some embodiments, the layer 20 may also include Chitosan.

Figure 3:
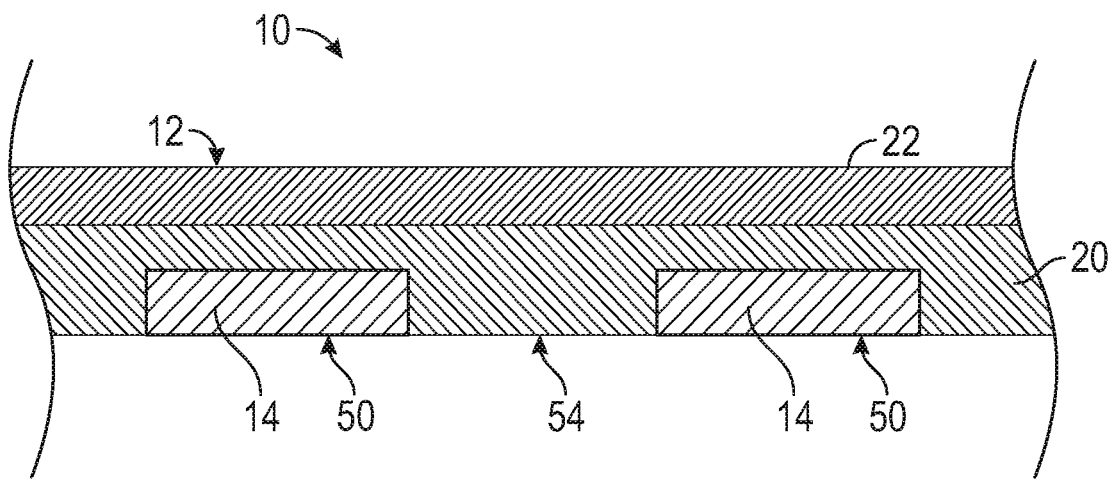
FIG. 3 is a cross-sectional view of an alternative embodiment of a wound covering.

In other embodiments, the first layer 18 can be omitted such that the covering 10 comprises the layer 20 and the layer 22, as illustrated in FIG. 3. In such a configuration, the layer 20 is the innermost layer, and is configured to be in contact with a wound on which the covering is placed.

Turning now to the sensor elements 14, the sensor elements 14 can be arrayed at various locations around the covering 10, and incorporated into any of the layers of the covering, depending upon the particular construction and characteristics desired. For example, the sensor elements 14 can be arrayed in a grid pattern, as in FIG. 1, or in any other arrangement. With reference to FIG. 2, the sensor elements 14 can be incorporated into the first layer 18 such that lower surfaces 50 of the sensor elements are coplanar with a lower surface 52 of the first layer, allowing the sensor elements to be directly in contact with a wound. In embodiments in which the first layer 18 is relatively thin, the sensor elements 14 can also be at least partially incorporated into the second layer 20, as illustrated in FIG. 2. In the embodiment of FIG. 3, the sensor elements can be incorporated into the second layer 20, and the lower surfaces 50 of the sensor elements 14 can be coplanar with a lower surface 54 of the second layer 20.

FIG. 4 is a magnified view of a sensor element 14, according to one embodiment. In the illustrated embodiment, the sensor elements 14 are square. However, in other embodiments, the sensor elements 14 can comprise any shape, such as circular, rectangular, etc. In certain embodiments, the sensor elements 14 can be subdivided into two or more regions, where each region is configured to sense a different parameter. For example, in the embodiment illustrated in FIG. 4, the sensor element 14 comprises four sensor regions 14A, 14B, 14C, and 14D. Each region can be configured to sense a different parameter, or can be configured to serve as a reference.

FIG. 5 illustrates a portion of the sensor region 14B in greater detail. The following discussion proceeds with reference to the sensor region 14B for ease of illustration, but the other sensor regions 14A, 14C, and 14D can also be configured in a similar manner. The sensor region 14B can comprise a plurality of flexible members referred to herein as fibers 24. The fibers 24 can be arranged in groups or sets oriented along one or more axes to form a mesh. For example, in the illustrated embodiment there are two sets of fibers 24A and 24B oriented along respective axes A and B. However, in other embodiments, the sensor regions can include any number of sets of fibers oriented along any number of axes, such as three axes, four axes, etc. In the illustrated embodiment, the axes A and B and the respective fibers 24A and 24B are perpendicular to each other such that the fibers are crisscrossed and form a mesh-like grid or scaffold. The crisscrossed fibers 24 also define openings or pores 26 between them. The fibers 24 can be continuous along the length or width of the sensor elements 14, or can originate and terminate within the boundaries of the particular sensor region in which they are located, depending upon the particular characteristics desired.

FIG. 6A illustrates a portion of a fiber 24 in greater detail as the fiber is being formed in a printing process, which is described in greater detail below. In the illustrated embodiment, the fibers 24 can comprise a plurality of sensor particles 28 embedded in the fibers. The sensor particles 28 are illustrated in greater detail in FIG. 6B. The sensor particles 28 can be dispersed within the fibers 24 at uniform or varying densities along the length of the fibers. In certain embodiments, the sensor particles 28 can be configured as microbeads or microspheres, as shown in FIG. 6B.

In a representative embodiment, the fibers 24 can have a diameter D of from 10 µm to 5 mm, 10 µm to 1 mm, from 100 µm to 800 µm, from 100 µm to 600 µm, or 500 µm to 1000 µm depending upon, for example, the diameter of the sensor particles 28 and the particular characteristics desired. In particular embodiments, the fibers 24 can have a diameter D of 600 µm. In certain embodiments, the fibers 24 oriented along a particular axis, such as the axis A, can be spaced apart from each other by, for example, from 100 µm to 10 mm, 200 µm to 5 mm, 500 µm to 3 mm, 1 mm to 3 mm, or 1 mm to 3 mm as measured from the center of one fiber to the center of the adjacent fiber. In particular embodiments, the fibers 24 can be spaced apart from each other by 1 mm center to center. In the illustrated embodiment, the size of the pores 26 can be a function of the fiber diameter and the spacing between adjacent fibers. In the illustrated embodiment, the pores 26 are approximately square, but may have lengths and widths that differ in size.

In certain embodiments, the sensor particles 28 can have a diameter of 1 µm to 1 mm, 5 µm to 800 mm, from 10 µm to 600 µm, from 10 µm to 400 µm, from 10 µm to 200 µm, or from 10 µm to 100 µm. In particular embodiments, the sensor particles 28 can have a diameter of 100 µm.

The fibers 24 can be made from flexible, low-adhesion, liquid-permeable materials, such as any of various hydrogels. For example, in certain embodiments the fibers 24 can be made from hydrogels comprising any of various polysaccharides such as alginate, agarose, chitosan, natural or synthetic proteins such as collagen, gelatin, gelatin methacryloyl, hyaluronic acid, tropoelastin, etc. In certain embodiments, the sensor particles 28 can comprise any of various polymeric materials, such as polyethylene glycol, polymeric resins such as ion-exchange resins including crosslinked polystyrene, Dowex® 50WX2 hydrogen form resin, etc. In particular embodiments, the sensor particles may comprise Dowex® 1×4 chloride form resin available from MilliporeSigma. The sensor particles 28 can also comprise hydrogel materials, such as any of the hydrogels described herein.

In certain embodiments, the sensor particles 28 can be doped with one or more indicator compounds, sensor compounds, or chemistries configured to undergo a detectable change in response to a selected analyte. For example, in some embodiments the indicator compounds and, thus, the sensor particles 28, can be configured to undergo a change in color, color intensity, absorption spectra, or other response to a selected wavelength or wavelength range of illumination when the indicator compounds are exposed to a selected analyte of interest. This can allow the sensor elements 14, and/or its sub-regions 14A-14D, to detect the presence of, or changes in, pH or other indicators of the acidity or basicity of an aqueous solution, compounds or solutes contained in a solution such as glucose, lactate, pyocyanin (a toxin released by certain gram-negative bacteria), etc. In particular embodiments, the sensor particles 28 can be substrates to which coatings of particular sensor compounds are applied.

In the illustrated embodiment, the sensor region 14A can be configured to undergo a detectable visual change in response to changes in pH. Thus, the sensor particles 28 embedded in the fibers 24 in the sensor region 14A can comprise any of various pH sensitive dyes, such as azo dyes including Brilliant Yellow ($C_{26}H_{18}N_4Na_2O_8S_2$), phenol red, universal pH indicator, anthocyanins such as present in red cabbage juice, etc., that undergo a change in color with changes in pH. In particular embodiments, the sensor region 14A can detect pH changes in the range from pH=4 to pH=9. In embodiments where the pH sensitive dye comprises Brilliant Yellow, the color of the dye can vary continuously from orange at pH=4 to dark red at pH=9. In embodiments where the pH sensitive dye comprises red cabbage juice, the color of the dye can vary continuously from purple at pH=4 to green at pH=9.

The sensor region 14B can be configured to undergo a detectable visual change in response to the presence of glucose, or changes in glucose concentration. Thus, the sensor particles 28 in the sensor region 14B can comprise glucose-sensitive indicator compounds such as glucose oxidase, horseradish peroxidase, trehalose, potassium iodide, sodium citrate buffer solution, or combinations thereof. In certain embodiments, the glucose-sensitive compounds can include any of various stabilizers or preservatives, such as citric acid ($C_6H_8O_7$). In particular embodiments, the sensor region 14B can detect changes in glucose concentration between 2 mM/L to 12 mM/L. In embodiments where the glucose sensitive dye comprises glucose oxidase, the color of the dye can vary continuously from orange at glucose concentrations of 2 mM/L to dark red at glucose concentrations of 12 mM/L.

The sensor region 14C can be configured to undergo a detectable visual change in response to the presence of lactate (e.g., L(+)-Lactate and/or related metabolic compounds), or changes in lactate concentration. Thus, the sensor particles 28 in the sensor region 14C can comprise lactate-sensitive indicator compounds or chemistries such as lactate dehydrogenase, lactate oxidase, etc. In particular embodiments, the MAK064 SIGMA Lactate Assay Kit available from MilliporeSigma may be used. In particular embodiments, the sensor region 14C can detect changes in lactate concentration between 1.6 mM/L to 100 mM/L. In embodiments where the lactate sensitive dye comprises the SIGMA Lactate Assay Kit, the color of the dye can vary continuously from orange at lactate concentrations of 1.6 mM/L to yellow and/or green at lactate concentrations of 100 mM/L.

In the illustrated embodiment, the sensor region 14D can include fibers 24 and sensor particles 28 without analyte-sensitive compounds. In this manner, the sensor region 14D can serve as a reference for visual inspection of the covering 10 by a user or a physician, and/or inspection of the covering 10 using an optical detection system described below.

In other embodiments, the sensor elements 14 can be subdivided into more or fewer regions, as desired. Additionally, in some embodiments, each sensor element 14 can be a standalone sensor configured to detect a particular analyte, and need not be subdivided, depending upon the particular application. In certain embodiments, the sensor elements 14 can be configured as planar substrates, such as sheets of cellulose or paper which are impregnated or coated with one or more selected indicator compounds.

The covering 10 may also comprise one or more humidity sensor elements 80 configured to detect changes in atmospheric humidity. With reference to FIG. 1, one or more humidity sensor elements 80 can be incorporated into the main body 12 as standalone components at any location throughout the thickness of the main body. In certain examples, the humidity sensor elements 80 can be configured to undergo a visual change in response to variation in the relative humidity of the environment of an individual wearing the wound covering 10. In certain examples, the sensor 80 can be incorporated into the outer surface of the covering 10, or within the main body. In other embodiments, the humidity sensor elements 80 may be incorporated into the sensor elements 14.

FIG. 7 illustrates a cross-sectional view of a representative embodiment of a humidity sensor element 80. In certain examples, the humidity sensor element 80 can comprise a metal or polymeric substrate 82, and a coating 84 comprising a sensor compound configured to undergo a visual change in response to the presence of water or moisture. In particular embodiments, the substrate 82 can comprise a silicon wafer, and the coating 84 can comprise graphene oxide. The coating 84 is shown applied to one surface of the substrate 82 (e.g., the outward facing surface of the substrate when the sensor 80 is on the wound covering 10). However, in other embodiments, the coating 84 may be applied to more than one surface of the substrate, or all of the surfaces of the substrate. In certain embodiments, the humidity sensors 80 can be configured to detect changes in relative humidity between 0% and 100%. In embodiments in which the humidity-sensitive coating 84 comprises graphene oxide, the color of the coating 84 can vary continuously between orange at 0% humidity and cyan at 100% humidity. In other embodiments, the humidity sensor 80 can be configured to monitor the water content of the covering 10, and/or of a wound over which the covering is placed.

Figure 8A:
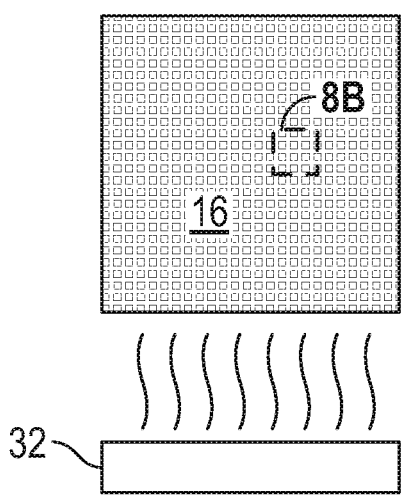
FIG. 8A is a top plan view illustrating a representative embodiment of a therapeutic agent delivery element, along with a schematic illustration of a heating element.
Figure 8B:
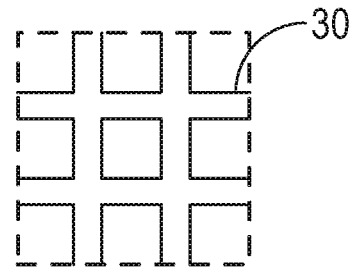
FIG. 8B is a magnified view of a portion of the therapeutic agent delivery element of FIG. 8A illustrating the hydrogel fiber mesh of the therapeutic agent delivery element.

Referring to FIG. 1 and FIGS. 8A and 8B, the therapeutic agent delivery elements 16 can comprise a porous mesh or grid-like scaffold including a plurality of flexible members or fibers 30 similar to the fibers 24 of the sensor elements 14. The fibers 30 can comprise a hydrogel material, such as any of the hydrogel materials described above. In particular embodiments, the fibers 30 can comprise alginate. In addition to the hydrogel, in certain embodiments the fibers 30 can comprise a relatively high concentration of one or more liquid therapeutic agents, such as antibiotics or antimicrobial agents, hormones, cellular growth factors, etc. In use, the therapeutic agents can diffuse out of the fibers 30 and into a wound on which the covering 10 is placed. Thus, in certain embodiments, the delivery elements 16 can be coplanar with the lower surface of the wound covering, similar to the sensor elements 14. Where the therapeutic agent comprises an antibiotic, this can help to reduce the risk of wound infection. Where the therapeutic agent is a hormone or growth factor, this can help to promote healing by stimulating cell growth in the wound. The fibers 30 can also be similar in size and spacing to the fibers 24 of the sensor elements 14. The fiber size and spacing can determine the size of the pores of the mesh, which can be related to the rate at which exudate diffuses into the delivery elements and the rate at which therapeutic agent diffuses out of the delivery elements and into the wound.

Example therapeutic agents include antibiotics such as ciprofloxacin hydrochloride, gentamicin sulfate, streptomycin, penicillin, etc., hormones such as growth hormone-releasing hormone, cellular growth factors such as fibroblast growth factor(s) (e.g., FGF1-FGF23 or combinations thereof), vascular endothelial growth factor(s) (e.g., VEGF-A-VEGF-D or combinations thereof), platelet-derived growth factor(s) (e.g., dimeric glycoproteins such as PDGFA, PDGFB, PDGFC, PDGFD, PDGFRA, PDGFRB, or combinations thereof), epidermal growth factor(s) (e.g., any of the EGF-family of proteins, including Heparin-binding EGF-like growth factor (HB-EGF), transforming growth factor-α (TGF-α), Amphiregulin (AR), Epiregulin (EPR), Epigen, Betacellulin (BTC), neuregulin-1 (NRG1), neuregulin-2 (NRG2), neuregulin-3 (NRG3), neuregulin-4 (NRG4), or combinations thereof), anti-fungal agents such as polyene antimycotics, anti-inflammatory agents such as ibuprofen, anti-scarring agents, pain-relieving agents such as the opioids given above, stem cells such as human-induced pluripotent stem cells, etc.

Figure 9A:
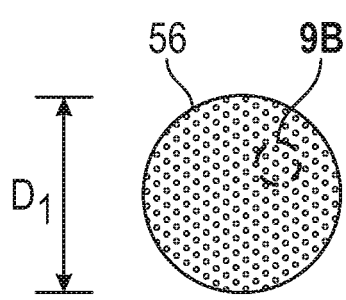
FIG. 9A is a top plan view of a porous therapeutic agent-containing particle in a neutral pH environment, according to one embodiment.

In some embodiments, the delivery elements 16 can be configured to release therapeutic agent into a wound by diffusion along a concentration gradient. In certain embodiments, the delivery elements 16 can be configured to selectively release therapeutic agent into a wound in response to certain stimuli or changes in certain parameters. For example, the fibers 30 of the delivery elements 16 can comprise a plurality of therapeutic agent-containing particles dispersed through the volume of the fibers, similar to the particles 28 and the fibers 24 of the sensor elements 14. In certain embodiments, the particles can comprise a material that can be selectively activated to release therapeutic agent, or to increase the rate of release, in response to changes in pH. FIG. 9A illustrates a representative embodiment of a therapeutic agent-containing particle 56. In the illustrated embodiment, the particle 56 can be a spherical, porous structure comprising a plurality of openings or pores schematically illustrated at 58 in FIG. 9B. The particle 56 can comprise a supply of one or more therapeutic agents, which can be released into the surrounding environment via the pores 58. The therapeutic agent can include any of the antibiotic or growth factor compounds described above.

In certain embodiments, the particles 56 can comprise Chitosan-based hydrogel. In certain configurations, Chitosan hydrogels can swell in acidic environments (e.g., pH less than 7). At neutral pH, the pores 58 can have an average pore size $x_1$ (e.g., measured along the largest dimension of the pores 58), and the particles 56 can have an initial diameter $D_1$. As the environment becomes more acidic, the particles 56 can swell to a second diameter $D_2$ that is larger than the initial diameter $D_1$. For example, in certain embodiments, Chitosan-based hydrogels can comprise a glucosamine backbone containing a high density of functional amino groups. These amino groups can become protonated in acidic pH conditions, causing an internal charge repulsion, which can lead the hydrogel and, thus, the particle 56, to swell to the second diameter $D_2$. This swelling of the particle 56 can cause an attendant increase in the size of the pores 58 from the initial pore size $x_1$ to a second pore size $x_2$ that is larger than the initial pore size $x_1$. This can increase the rate of release of the therapeutic agent from the interior of the particle 56 into the body of the covering 10, and from the covering 10 into the wound.

In some embodiments, the initial diameter $D_1$ can be from 10 μm to 500 μm, from 50 μm to 500 μm, or from 100 μm to 500 μm. In particular embodiments, the initial diameter $D_1$ can be 250 μm. In some embodiments, the diameter $D_2$ can be from 20 μm to 1000 μm, from 100 μm to 1000 μm, or from 200 μm to 1000 μm, depending upon the particular hydrogel formulation. In some embodiments, the initial pore size $x_1$ can be from 1 nm to 100 nm, 1 nm to 80 nm, 1 nm to 50 nm, 1 nm to 25 nm, 1 nm to 10 nm, or 2 nm to 8 nm. In particular embodiments, the initial pore size $x_1$ can be 3 nm. In some embodiments, the diameter and pore size ranges above can occur over pH ranges from pH=7 to pH=4. In some embodiments, the flow rate of therapeutic agent can increase between $x_1$ and $x_2$ and $D_1$ and $D_2$. In certain embodiments, the particles 56 can be configured to deliver a burst of therapeutic agent upon a change in pH from neutral to acidic.

Figure 9B:
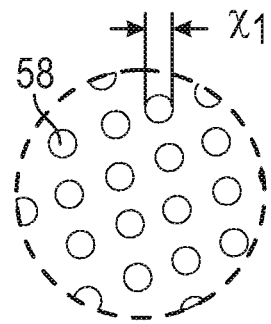
FIG. 9B is a magnified view of a portion of the therapeutic agent-containing particle of FIG. 9A illustrating the pores of the particle.
Figure 10A:
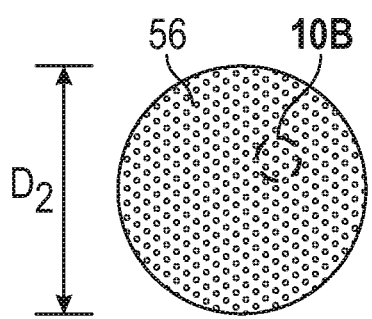
FIG. 10A is a top plan view of the therapeutic agent-containing particle of FIG. 9A illustrating enlargement of the particle in an acidic environment.
Figure 10B:
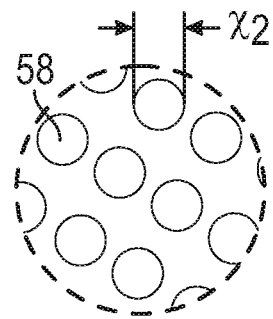
FIG. 10B is a magnified view of a portion of the therapeutic agent-containing particle of FIG. 10A illustrating an increased size of the pores of the particle in an acidic environment.

In certain embodiments, particles such as the particles 56 can comprise a hydrogel material that swells or increases in size when the environment becomes basic. For example, in certain embodiments the particles 56 can comprise poly(N-isopropylacrylamide-co-acrylic acid), referred to herein as "P(NIPAM-co-AAc)." Referring again to FIG. 9A, at neutral pH the particle 56 comprising P(NIPAM-co-AAc)-based hydrogel can have the initial diameter $D_1$. The pores 58 of the particle 56 can have an initial pore size $x_1$ as illustrated in FIG. 9B, similar to the Chitosan particles. As the environment becomes basic, carboxylic groups in P(NIPAM-co-AAc) can become deprotonated. This can lead to the generation of internal charge repulsion between the molecules of the hydrogel, which can cause the particle 56 to swell or increase in size to the second diameter $D_2$ illustrated in FIG. 10A. This can result in an attendant increase in the pore size from the initial pore size $x_1$ to a second pore size $x_2$ that is larger than the initial pore size $x_1$, as illustrated in FIG. 10B. This can increase the rate of release of the therapeutic agent from the interior of the particles 56, similar to the Chitosan embodiments described above, but in a basic environment.

The delivery elements 16 can comprise fibers 30 including particles 56 comprising Chitosan and/or other acid-responsive hydrogels, and particles 56 comprising P(NIPAM-co-AAc) and/or other base-responsive hydrogels. In this manner, the delivery elements 16 can be configured to increase the rate of release of therapeutic agents, such as antibiotics, via the particles 56 in case of infection by bacteria or fungi that tend to turn the wound environment acidic, as well as bacteria or fungi that tend to turn the wound environment basic.

In other embodiments, the fibers 30 can include a coating that prevents diffusion of the therapeutic agent out of the fibers, and which is degraded by changes in pH. Thus, if the pH of wound exudate increases or decreases due to the onset of a bacterial or fungal infection, the coating can break down, allowing antibiotic in the fibers 30 to diffuse into the wound. In an exemplary embodiment, such coatings may comprise Chitosan and P(NIPAM-co-ACC).

Figure 13:
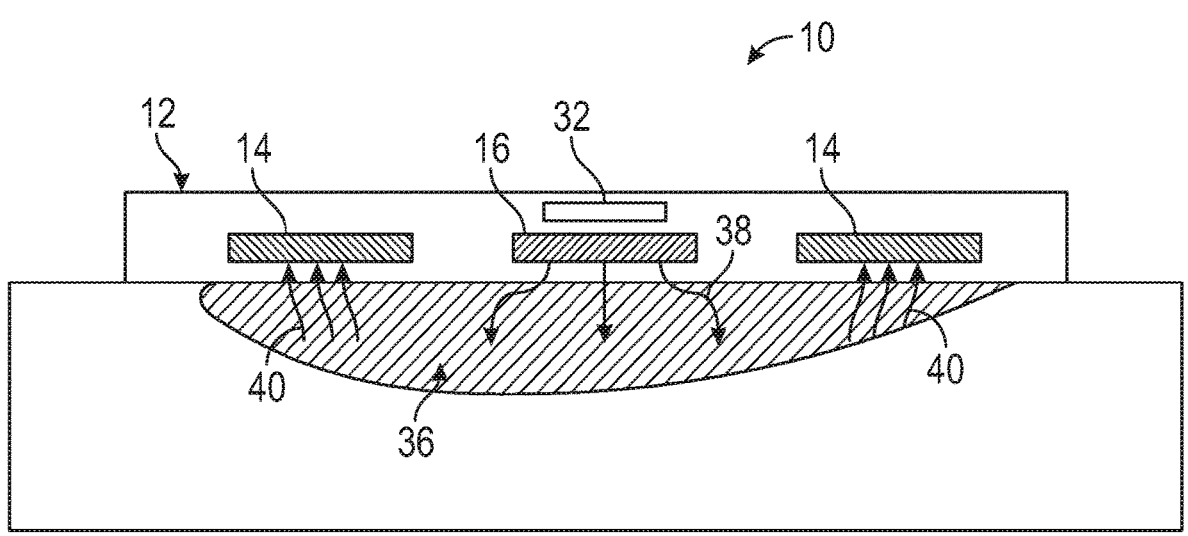
FIG. 13 is a schematic cross-sectional view illustrating the wound covering of FIG. 1 in place on a wound.

In certain embodiments, the delivery elements 16 can be configured to release therapeutic agent into a wound by heat stimulus. For example, in the illustrated embodiment, the main body 12 can comprise one or more electrically-conductive structures schematically illustrated in FIG. 8A as heating elements 32. The heating elements 32 can comprise, for example, a patterned electrode incorporated on or in the main body 12, and configured to heat the covering 10 when an electric current is applied. The electrodes can be made of conductive nanoparticles including single and/or multi-walled carbon nanotubes, graphene, graphene oxide, reduced graphene oxide nanoparticles, metallic nanowires such as gold, magnesium, etc. Patterning of the electrodes can be performed by screen printing, inkjet printing, nozzle-based printing, molding, etc. Electric current can be applied by, for example, a microcontroller (not shown) incorporated into the main body 12 and electrically connected to the heating element 32, and comprising a battery. In certain examples, the heating elements 32 can be positioned in the main body 12 above the delivery elements, as shown in FIG. 13, or below the delivery elements 16 as shown in FIG. 8A. The heating elements 32 can also be disposed on the outer surface of the main body. Heating of the fibers 30 by the heating elements 32 can cause the fibers to release therapeutic agent into the wound, as further described below. Each delivery element 16 can have a corresponding heating element 32, or the main body 12 can comprise one heating element 32 that is sufficiently large to heat several delivery elements 16 simultaneously.

Figure 11A:
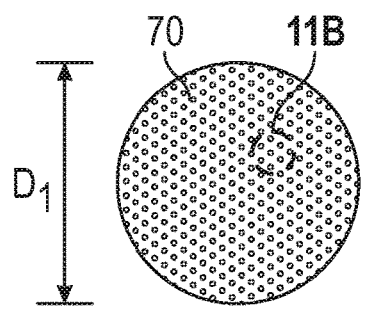
FIG. 11A is a top plan view of another embodiment of a porous therapeutic agent-containing particle in a neutral pH environment.
Figure 11B:
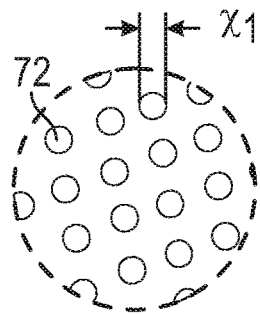
FIG. 11B is a magnified view of a portion of the therapeutic agent-containing particle of FIG. 11A illustrating the pores of the particle.
Figure 12A:
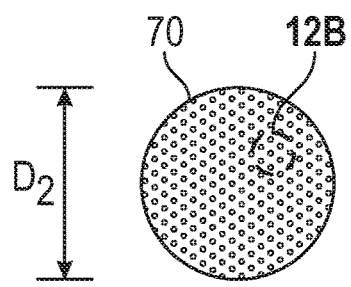
FIG. 12A is a top plan view of the porous therapeutic agent-containing particle of FIG. 11A illustrating shrinking of the particle in a basic environment.
Figure 12B:
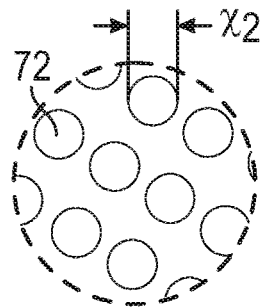
FIG. 12B is a magnified view of a portion of the particle of FIG. 12A illustrating an increased size of the pores of the particle in a basic environment.

For example, in certain embodiments the fibers 30 of the delivery elements 16 can comprise temperature-sensitive drug-releasing particles, such as the representative particle 70 shown in FIG. 11A. In certain embodiments, the particles 70 can comprise heat-sensitive materials, such as heat-sensitive hydrogels including poly N-isopropylacrylamide (PNIPAM). At normal body temperature (e.g., 37° C.), the particles 70 can have an initial diameter $D_1$. In certain embodiments, the particles 70 can be porous, and can include a plurality of pores schematically illustrated at 72 in FIG. 11B, and having an initial pore size $x_1$. With reference to FIG. 11B, as the wound dressing increases in temperature (e.g., from the heating influence of the heating element 32), the particles 70 can decrease in size to a second diameter $D_2$ that is smaller than the initial diameter $D_1$. As the particle size decreases, the pore size can increase to a second pore size $x_2$ that is larger than the pore size $x_1$. The increased pore size attendant to increased temperature of the particles 70 can allow an increased flow of therapeutic agent out of the particles 70 and into the wound environment. Thus, application of heat via the heating element 32 can allow a user or a physician to control the timing and amount of therapeutic agent delivered by the delivery elements 16. In a representative embodiment, the particles 70 can be configured to release therapeutic agent at temperatures above 35° C., or in a temperature range from 35° C. to 47° C. In certain embodiments, the PNIPAM in the particles 70 can undergo a transition from hydrophilic to hydrophobic at temperatures above 40° C. to 45° C. The hydrophobicity of the PNIPAM particles 70 at elevated temperature can increase the flow of aqueous therapeutic agents from out of the particles 70.

In other embodiments, the fibers 30 and/or the particles 70 can be configured to release therapeutic agent in response to an applied electric current. In yet other embodiments, the delivery elements 16 can be configured as hydrogel membranes comprising therapeutic agents and/or therapeutic-doped particles such as the particles 56 and/or the particles 70, and need not include the fibers 30. In yet other embodiments, therapeutic agents and/or particles 56 and/or 70 need not be incorporated into hydrogel fibers, but can be incorporated directly into one or more of the constituent layers of the covering 10, such as the second layer 20.

In some embodiments, the covering 10 can be configured to allow oxygen diffusion through the main body 12 into a wound. For example, in certain embodiments the main body 12 can comprise oxygen-releasing particles 13 configured to oxygenate the wound environment. The oxygen-releasing particles 13 can be similar in size and shape to any of the particles 28, 56, or 70 described above. In certain embodiments, the oxygen-releasing particles 13 can be made by encapsulating solid inorganic peroxides such as calcium peroxide ($CaO_2$), sodium percarbonate (($Na_2CO_3$)$_2 \cdot 1.5H_2O_2$) and magnesium peroxide ($MgO_2$) or perfluorocarbons in hydrophobic polymers such as polydimethylsiloxane (PDMS), poly lactic-co-glycolic acid (PLGA), polycaprolactone (PCL), etc., using oil-in-oil emulsion. Solvents that may be used in a representative emulsion process include dichloromethane, dimethyl sulfoxide, hexaflu's oroisopropanol, and/or ethyl acetate. In certain embodiments, the oxygen-releasing particles 13 may be fibrous particles formed by electrospinning polymeric fibers.

Generation of oxygen molecules by the oxygen-releasing particles may occur in the following sequence. Formation of hydrogen peroxide ($H_2O_2$) can takes place in a first reaction step upon exposure of solid inorganic peroxides to water (e.g., when the wound covering is placed on a wound). Equation (1) below gives a first reaction step for calcium peroxide, Equation (2) gives the reaction for magnesium peroxide, and Equation (3) gives the reaction for sodium percarbonate.

$$CaO_2(s)+2H_2O \rightarrow Ca(OH)_2(s)+H_2O_2 \quad (1)$$

$$MgO_2(s)+2H_2O \rightarrow Mg(OH)_2+H_2O_2 \quad (2)$$

$$(Na_2CO_3)_2 \cdot 3H_2O \rightarrow 4Na^+ + 2CO_3^{-2} + 3H_2O_2 \quad (3)$$

This may be followed by decomposition of $H_2O_2$ into oxygen in a second reaction step common to the three inorganic peroxides above, and given below in Equation (4).

$$2H_2O_2 \rightarrow O_2 + 2H_2O \quad (4)$$

In certain embodiments, catalase may be used as a catalyst to facilitate the conversion of $H_2O_2$ into oxygen. Catalase is an enzyme present in the liver and blood of mammals, and can be used to decompose $H_2O_2$ into water and oxygen with high turnover efficiency. Catalase enzyme comprises four heme (iron-containing organic ring) groups embedded within its structure, which can be utilized in oxygen-conversion processes. The mechanism of the decomposition reaction of $H_2O_2$ is given by Equations (5) and (6) below.

$$2H_2O_2(aq)+2Fe^{3+}(aq) \rightarrow O_2(g)+2Fe^{2+}(aq)+2H^+(aq) \quad (5)$$

$$H_2O_2(aq)+2Fe^{2+}(aq)+2H^+(aq) \rightarrow 2H_2O(l)+2Fe^{3+}(aq) \quad (6)$$

In certain embodiments, the oxygen-releasing particles can be dispersed throughout the covering 10, such as in the second layer 20, concentrated in certain regions, and/or contained in hydrogel fibers similar to the sensor elements 14 and the therapeutic agent delivery elements 16. Diffusion of oxygen into the wound site from the oxygen-releasing particles can reduce the risk of hypoxia and aid in wound healing.

FIG. 13 illustrates the covering 10 situated on a wound 36. In use, therapeutic agents generally indicated at 38 can diffuse into the wound 36 from the delivery elements 16 at a rate determined by a concentration gradient between the delivery elements and the wound, and/or when the particles 56 and/or 70 are activated as described above. Exudate from the wound generally indicated at 40 can also come in contact with the lower surface of the covering 10. The exudate 40 can diffuse into the main body 12, where molecules in the exudate can interact with the various sensor elements 14 and/or with the delivery elements 16 and the particles 56. This can allow remote monitoring of the wound for changes indicative of infection, such as changes in the color of the various sensor elements 14 or portions thereof.

Figure 14:
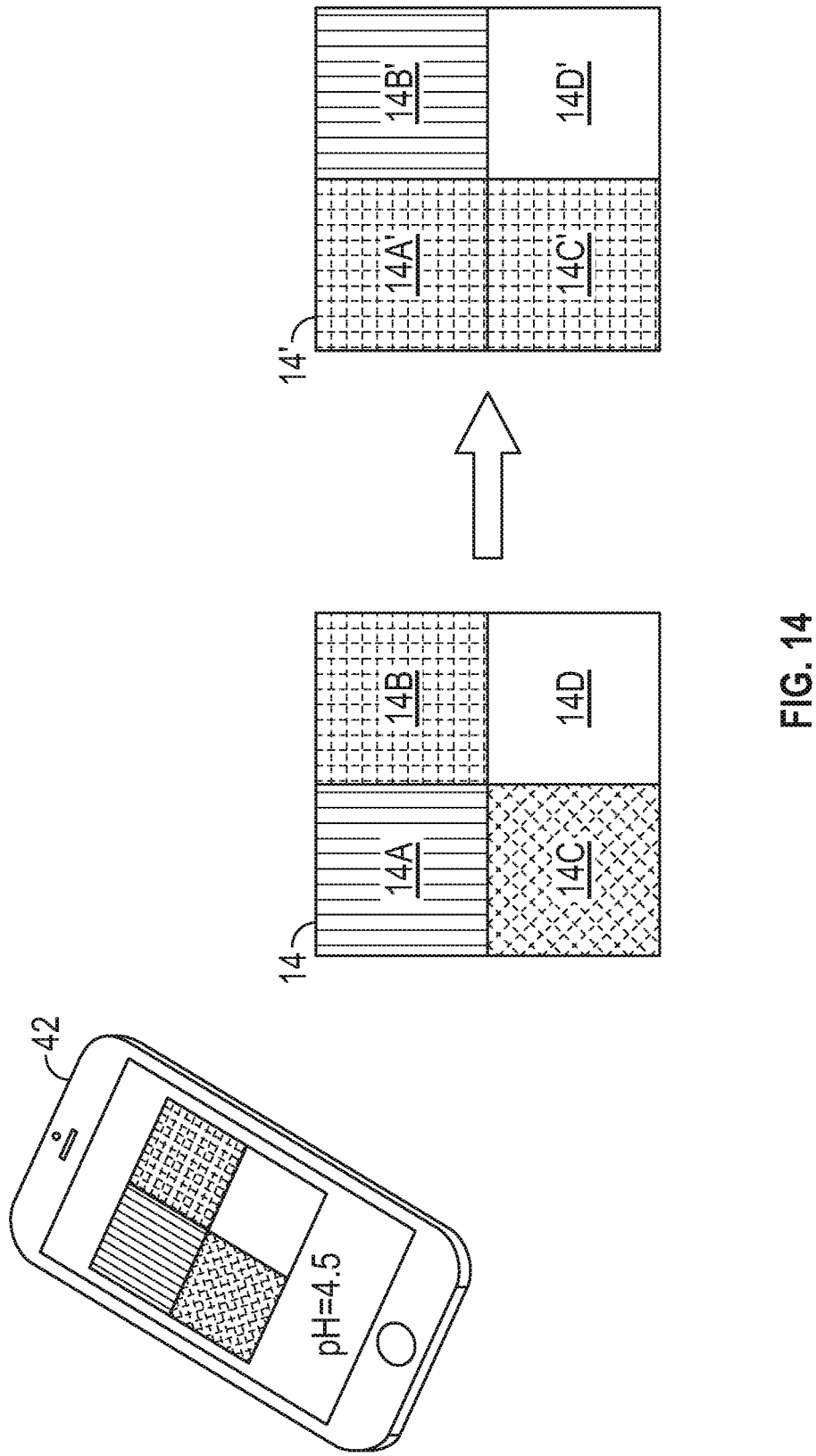
FIG. 14 includes a schematic top plan view of a sensor element illustrating the change in color of the various portions of the sensor element in response to changes in parameters of wound exudate to which the respective sensor element portions are sensitive, along with a perspective view of a smartphone that may be used to produce image data of the sensor element.

For example, FIG. 14 schematically illustrates a representative sensor element 14 configured as described above, wherein the region 14A is configured to undergo a color change in response to changes in pH, the region 14B is configured to undergo a color change in response to changes in glucose concentration, the region 14C is configured to undergo a color change in response to changes in lactate concentration, and the region 14D is configured as a neutral reference. The left-hand side of FIG. 14 illustrates the sensor element 14 as it appears in the presence of normal internal body fluids. In the illustrated embodiment, the sensor particles 28 in the fibers 24 (FIG. 5) of the region 14A comprise Brilliant Yellow dye, which can be red at or near neutral pH (e.g., at pH=7.4, the typical pH of internal body fluids). Thus, the region 14A is shaded to connote red on the left-hand side of FIG. 14. The sensor particles 28 in the fibers 24 of the sensor region 14B comprise a mixture of glucose oxidase, horseradish peroxidase, trehalose, and potassium iodide in a sodium citrate buffer solution, which can be light yellow in color at normal glucose concentrations (e.g., 3.9 to 5.5 mM/L). Thus, the region 14B is shaded to connote yellow on the left-hand side of FIG. 14. The sensor particles 28 in the fibers 24 of the sensor region 14C can comprise lactate dehydrogenase, and can be orange at normal lactate concentrations (e.g., 0.5 to 1 mM/L). Thus, the sensor region 14C is shaded to connote the color orange on the left-hand side of FIG. 14. The region 14D can be relatively translucent and/or colorless.

The right-hand side of FIG. 14 illustrates the sensor element denoted as 14', and its sub-regions denoted as 14A'-14D', after exposure to changes and/or elevated levels of their respective analyte parameters. For example, in the event of infection by *S. aureus* bacteria, the pH of the wound exudate may become more acidic (e.g., the pH may change from pH=7.4 to pH=6). This can cause the brilliant yellow dye in the sensor particles of the region 14A to turn yellow, making the region 14A' appear yellow, as shown on the right-hand side of FIG. 14. In the event of infection by bacteria such as *P. aeruginosa*, the pH of the wound exudate may become more alkaline (e.g., from pH=7.4 to pH=9), which can cause the brilliant yellow dye to turn a darker shade of red. An increase in glucose concentration (e.g., to 12 mM/L) can cause the glucose oxidase in the sensor particles of the region 14B to turn red, making the region 14B' appear red. Likewise, an increase in lactate concentration (e.g., to 50 mM/L), can cause the lactate-sensitive dye in the sensor particles of the region 14C to turn yellow, making the region 14C' appear yellow, as shown on the right-hand side of FIG. 14. High concentrations of lactate can also make the region 14C' appear green or yellow-green. Additionally, while these color changes are shown concurrently on the sensor element 14', it should be understood that color changes of the various regions of the sensor element 14 may occur together or independently of each other, depending upon the particular pathology of the wound.

Color changes in the sensor elements or regions thereof can be noted visually, and/or by use of an optical detection system. For example, a patient or a physician may use a mobile device including a camera, such as a smartphone or a tablet computer, to photograph the covering 10 on the wound and analyze the color of the various sensor elements to detect changes and determine if treatment may be required. FIG. 14 illustrates use of a smartphone 42 to capture images of the covering 10. In certain embodiments, the smartphone 42 can include an image processing application to produce grayscale images in the red, blue, and/or green channels from the initial image taken by the smartphone 42, as further described below. The light intensity in the grayscale images can be compared to predetermined polynomial curves representative of the color of the various sensing compounds as a function of analyte concentration. If the intensity of one or more of the grayscale images in the red, blue, and/or green channels indicates that a compound or parameter of interest has increased or decreased beyond a predetermined threshold, the application can alert the user and/or physician that further analysis or treatment may be required. If the value of the parameter indicates the presence of a bacterial infection in the wound, the physician and/or the user may remove the wound covering 10 for further treatment, such as cleaning and/or disinfecting of the wound, and/or application of a replacement wound covering 10.

Referring again to FIG. 1, in some embodiments the covering 10 may comprise one or more color references, such as reference areas 44 and 46 comprising known colors for use as references when analyzing images of the covering to compensate, for example, for variations in lighting. In the illustrated embodiment, the reference area 44 is shaded to connote the color red and the reference area 46 is shaded to connote the color blue, although the covering may include any number of reference areas have any desired color. In certain embodiments, the reference areas 44 and 46 can be located on a border 48 (e.g., a polymeric film on the third layer 22), which can be a neutral color, such as white.

Algorithms and techniques for analyzing images of the covering 10 are described in greater detail below with reference to FIGS. 21A-21I and 28A-31B. A representative embodiment of a mobile device that may be used to perform the image capture and analysis is described below with reference to FIG. 32. In certain embodiments, the mobile device may be in communication with a remote server or computing platform, and may transmit image data of the covering and sensor elements to the remote server for analysis, and receive data of the analyzed images, including alerts, from the remote server for display to a user. Remote computing platforms, such as cloud computing platforms, that may be used for analyzing images of the covering 10 are discussed in greater detail below with reference to FIG. 33.

Returning to FIG. 6A, the sensor elements 14 and/or the delivery elements 16 can be three-dimensionally printed using, for example, a microextruder 60. The microextruder 60 can comprise two coaxial needles 62 and 64 mounted on a 3D printer (e.g., a Prusa i3). The porosity of the sensor elements 14 can be adjusted by changing the diameter of the fibers 24 while keeping the spacing between fibers constant. Uncrosslinked hydrogel material (e.g., alginate) can be mixed with the sensor particles 28, and the mixture can flow through the lumen of the inner needle 62 onto a substrate 68. Meanwhile, a crosslinking agent 66 (e.g., a calcium chloride ($CaCl_2$) solution) can flow through the outer needle 64 such that the hydrogel material is bathed in crosslinking agent as the hydrogel is extruded from the needle 62. The crosslinking agent 66 can crosslink or cure the uncrosslinked hydrogel to form the fibers 24. The substrate 68 can be moved relative to the microextruder 60, or vice versa, to create the desired mesh pattern of fibers 24. A similar method can be used to fabricate the fibers 30 of the delivery elements 16.

Referring to FIG. 15, to prepare the covering 10, uncrosslinked or partially crosslinked hydrogel material (e.g., Chitosan) corresponding to the first layer 18 can be added to a mold 90. One or more sensor elements 14 and/or delivery elements 16 can then be situated in the mold 90, and uncrosslinked hydrogel material (e.g., alginate) corresponding to the second layer 20 can then be added to the mold. A crosslinking agent can then be added to the mold 90. For example, in certain embodiments a crosslinking member 92 can be situated on top of the hydrogel in the mold 90. The crosslinking member 92 can comprise a crosslinking agent, such as calcium chloride ($CaCl_2$) in order to crosslink the hydrogel to form the first and second layers 18 and 20. In certain embodiments, the crosslinking member 92 can comprise an agarose sheet. The crosslinked first and second layers 18, 22 can then be removed from the mold 90, and the third layer 22 can be applied to the second layer to form the main body 12. In other embodiments, the first and second layers 18 and 22 can be crosslinked by introducing a liquid crosslinking agent solution to the mold 90. One or more humidity sensor elements 80 can be incorporated into the first layer 18, the second layer 20, and/or into the third layer 22, as desired. Additionally, although not shown, one or more heating elements 32 can also be placed in the mold 90 and incorporated into the main body 12, and/or patterned on a surface of the main body after curing.

Example 1

Figure 16A:
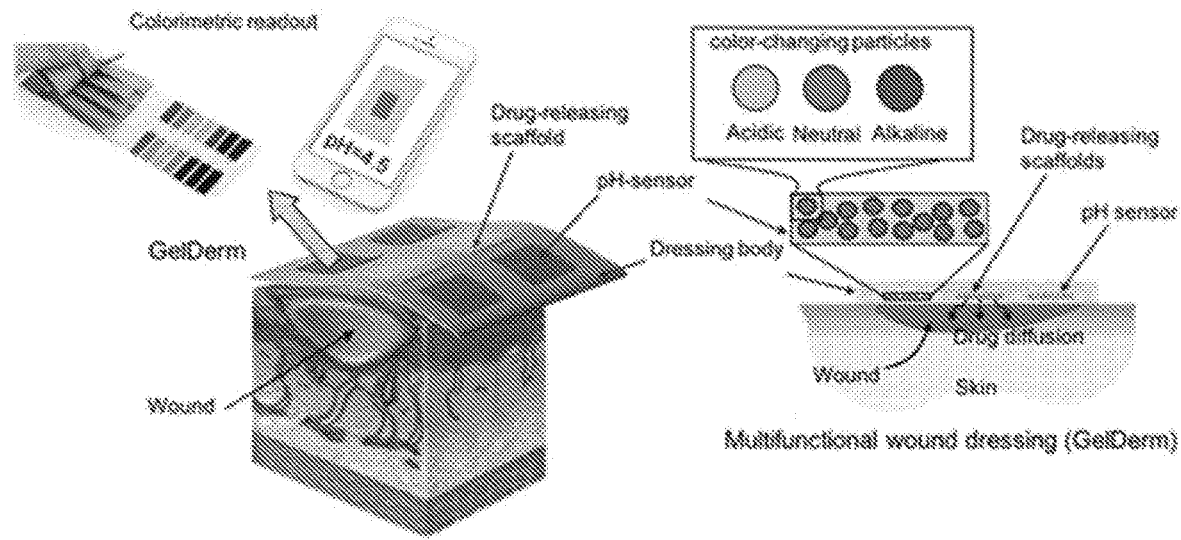
FIGS. 16A-16G illustrate various embodiments of wound coverings, and systems and methods of making the same.
Figure 16B:
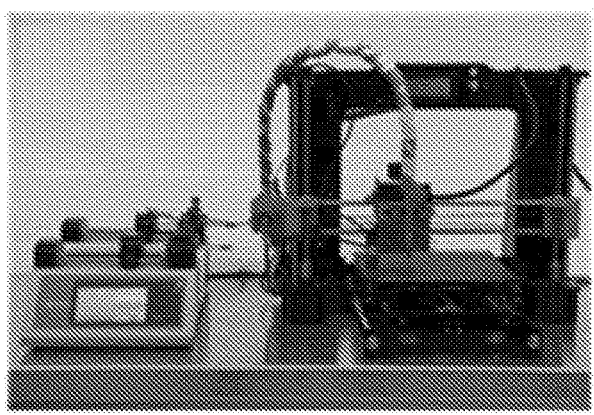
Figure 16C:
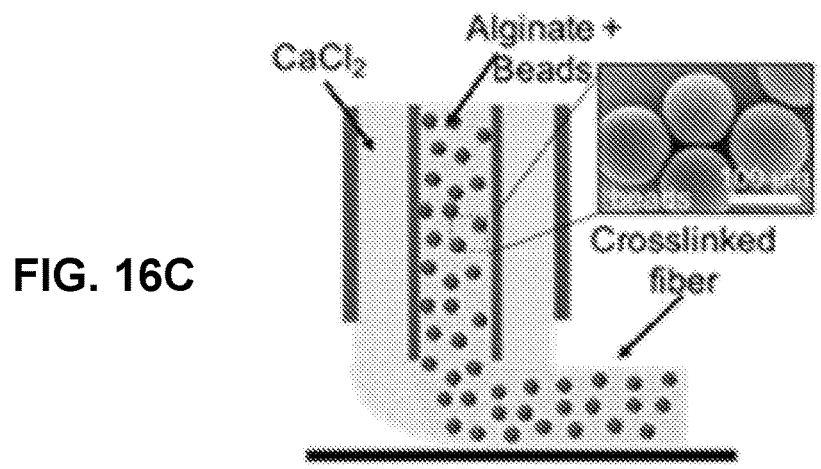
Figure 16D:
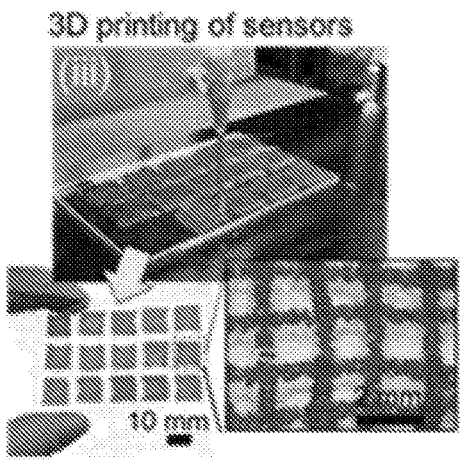
Figure 16E:
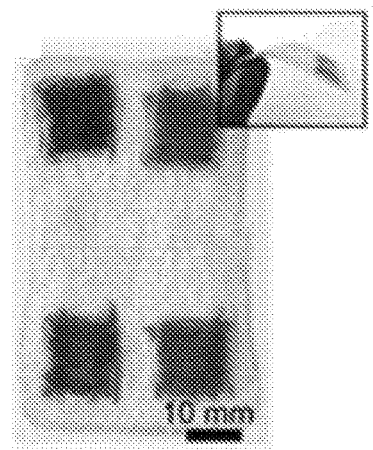
Figure 16F:
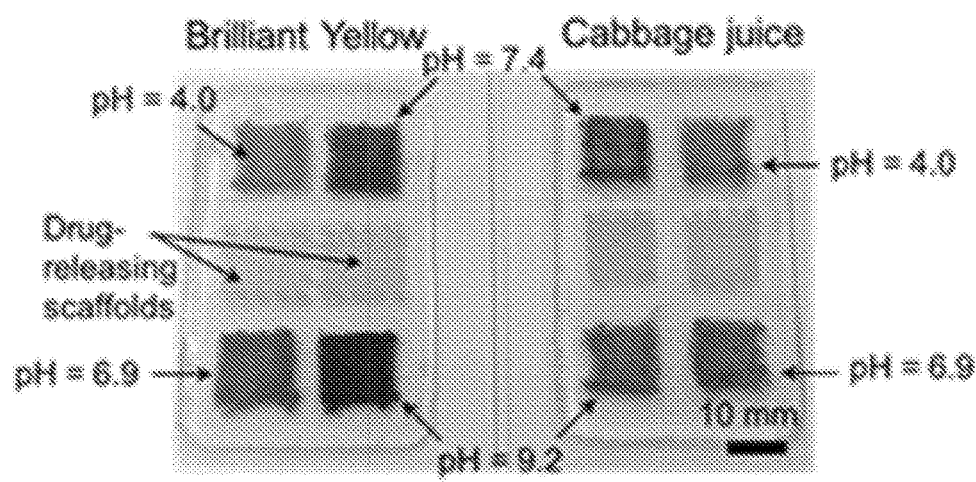
Figure 16G:
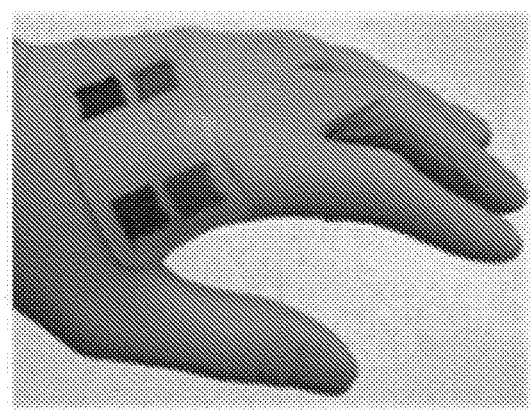
Figure 22A:
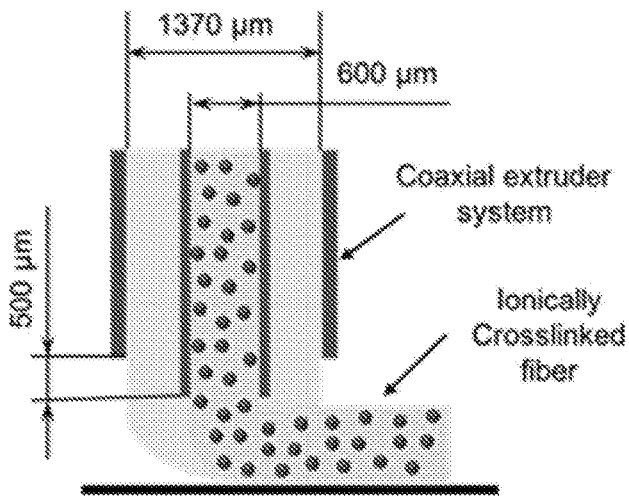
FIGS. 22A and 22B illustrate a co-axial needle microextruder apparatus for depositing color-changing hydrogel fibers, according to one embodiment.
Figure 22B:
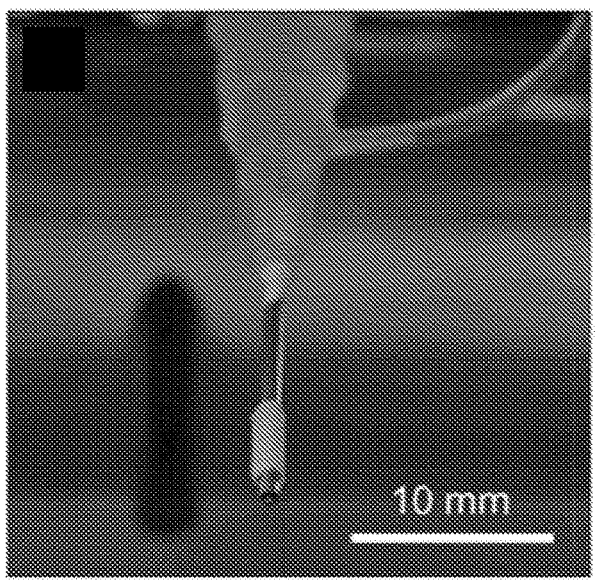
Figure 23A:
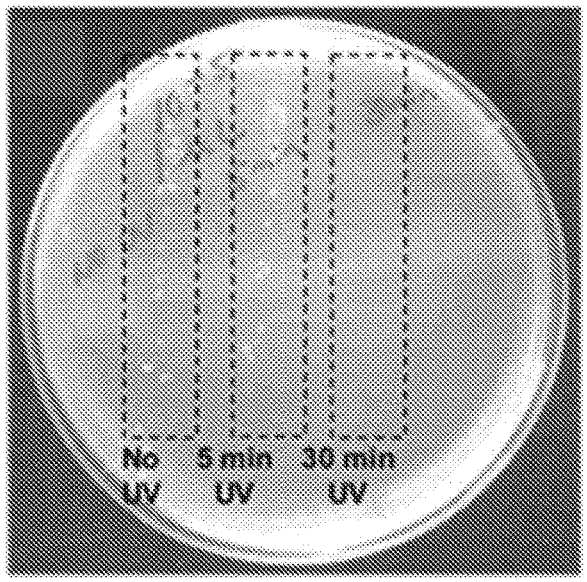
FIGS. 23A-23C illustrate the effect of UV-sterilization of dressings.
Figure 23B:
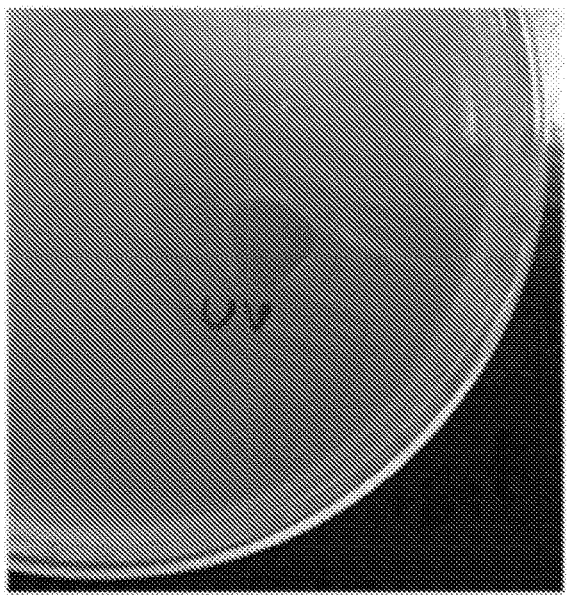
Figure 23C:
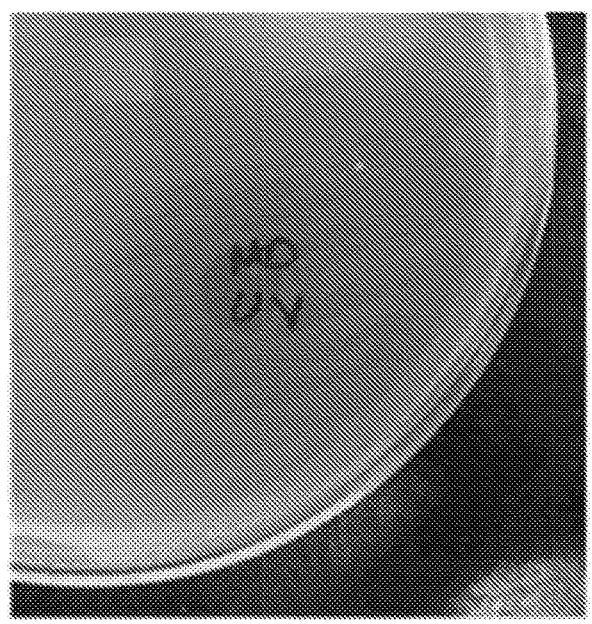
Figure 24:
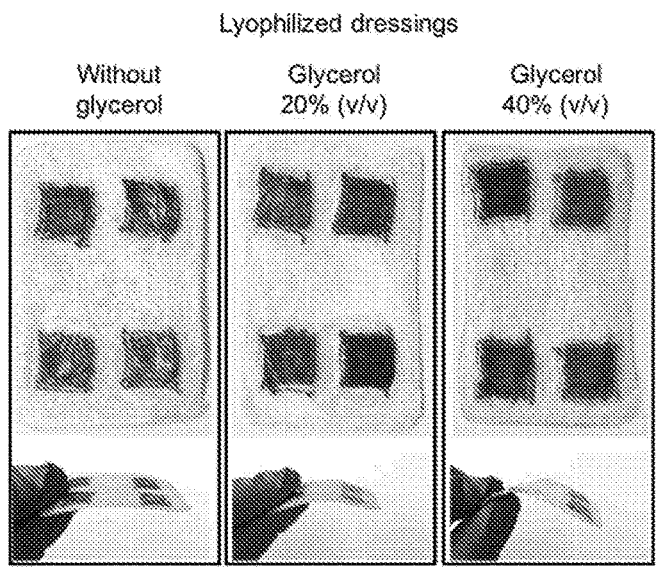
FIG. 24 illustrates the effect of glycerol concentration on flexibility of wound coverings after lyophilization.

In a representative example, multifunctional dressings were made according to the embodiments described herein comprising an array of porous color-changing pH sensors (e.g., the sensing elements 14) and drug-eluting scaffolds (e.g., the therapeutic agent delivery elements 16), which were embedded within an alginate dressing (FIG. 16A). The array of porous sensors (each sensor was 12×12 mm in size) comprised three-dimensionally (3D)-printed color-changing alginate fibers that were loaded with mesoporous resin beads doped with a pH-responsive dye (FIGS. 16A-16G). Alginate is a naturally-derived polysaccharide that can be used as a dressing material for epidermal applications due to its biocompatibility, hemostatic properties, and non-adhesive characteristics that facilitate the removal of the dressing without trauma and pain (14-18). With reference to FIG. 6A and FIGS. 16B and 16C, to print the sensors, a microextruder 60 comprising two coaxial needles 62 and 64 (FIG. 16C and FIGS. 22A-22B) mounted on a 3D printer (e.g., a Prusa i3) was used. The porosity of the sensors was adjusted by changing the diameter of the fibers while keeping the spacing between fibers constant. Encapsulation of the beads within the hydrogel fibers prevented the beads from dispersing in the wound area while providing a biocompatible interface with the wound site. Similarly, drug-eluting scaffolds were fabricated by 3D printing gentamicin-loaded alginate fibers (0.5-3.0 mg/ml). After fabrication, the dressing was first sterilized through exposure to ultraviolet (UV) light (365 nm, 200 mW/cm$^2$) and then lyophilized for storage and further usage. To obtain the sterilization time, the dressings were intentionally contaminated with *Staphylococcus aureus* (*S. aureus*) and *Pseudomonas aeruginosa* (*P. aeruginosa*) at the concentration of 10$^5$ colony-forming units (CFUs) and systematically increased the UV exposure times up to 30 minutes. FIG. 23A shows the result of swab samples collected from UV-sterilized dressings that were grown on an agar plate. The results indicated that a 30-minute UV sterilization can be adequate for eradicating bacterial contaminations in the dressings. Comparing UV-sterilized gentamicin with control (drug that was not treated with UV) showed no impact of the UV exposure on the antibacterial efficiency of the drug (FIGS. 23B, 23C). FIG. 16E shows a typical dressing after the lyophilization process. To improve the flexibility and mechanical integrity of the lyophilized dressings, glycerol was added, which is a plasticizer for wound dressing and food packaging (19, 20), to alginate (FIG. 16E). Synthetic (Brilliant Yellow) and naturally-derived (cabbage juice) pH indicators can be used; however, other indicators can also be used in the system. The array of sensors enabled measuring the spatial variations of pH within the wound that could be caused by different bacterial infections (FIG. 16F). The hydrogel dressings were flexible and could maintain a conformal contact with the irregular surface of the skin (FIG. 16G).

Fabrication and Physical Characterization

Figure 17A:
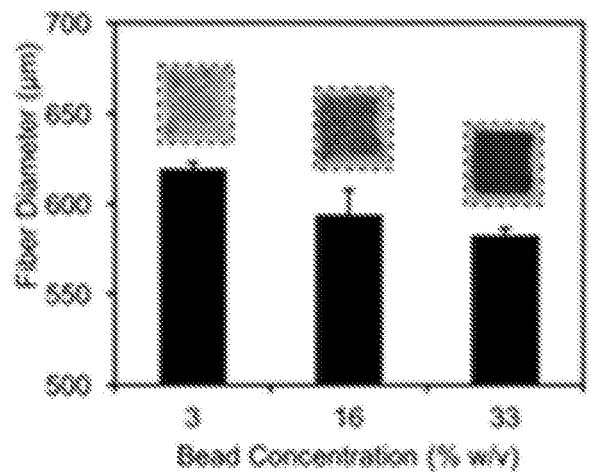
FIG. 17A is a bar chart illustrating the effect of sensor particle concentration on the diameter of printed hydrogel fibers.

Three-dimensional printing using a microfluidic coaxial extruder, mounted on a programmable XYZ positioning stage, provided an efficient route to fabricate porous sensors. An feature of the fabricated sensors, which could be controlled by the fiber diameter, was the available surface area per volume of the sensors. The more available surface per volume can significantly improve the response time of the sensors. Three bead densities of 3, 16, and 33% w/v were used to fabricate the sensors. Bead densities of more than 33% w/v may also be used. Higher bead densities in the printable range resulted in sensors that were more visible to the naked eyes as there was more signal produced by the color-changing beads, while increasing the bead density slightly reduced the diameter of the fabricated fibers (FIG. 17A).

Figure 17B:
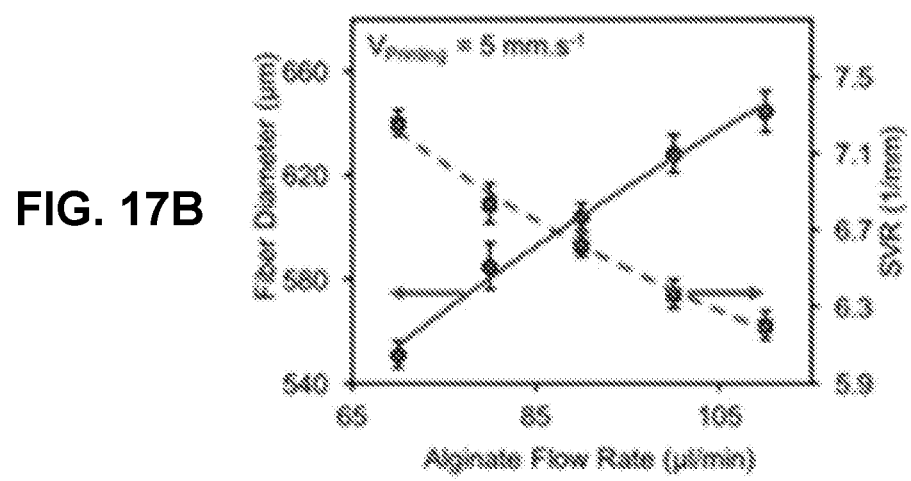
FIGS. 17B and 17C are graphs illustrating the fiber diameter versus alginate flow rate and nozzle travel speed, respectively.
Figure 17C:
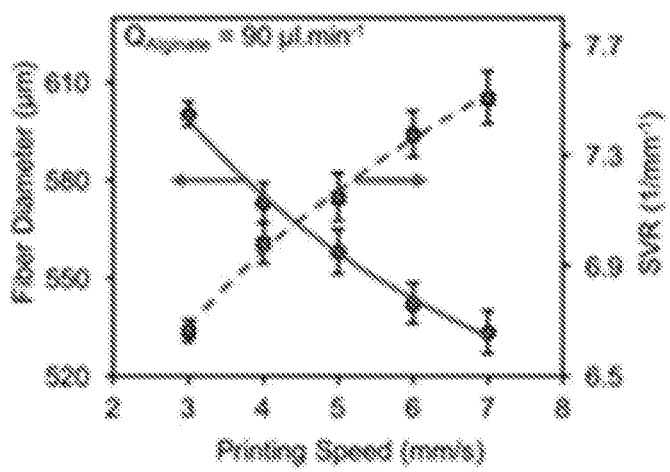

The fiber diameter varied with the loaded bead density, alginate injection rate, and printing speed. The following relationship in Equation (7) was used to estimate the surface-to-volume ratio (SVR)

$$SVR = \frac{4}{D} \quad (7)$$

where D is the diameter of fibers. By varying the rate of alginate injection and translational velocity of the extrusion nozzle, while holding the rate of calcium chloride ($CaCl_2$) constant (30 µl/ml), it is possible to adjust the diameter of the deposited fibers. The SVR of the printed sensors increased by 27% and 13% when the flow rate of alginate was decreased by 60% and doubled the printing speed, respectively (FIGS. 17B and 17C).

Figure 25A:
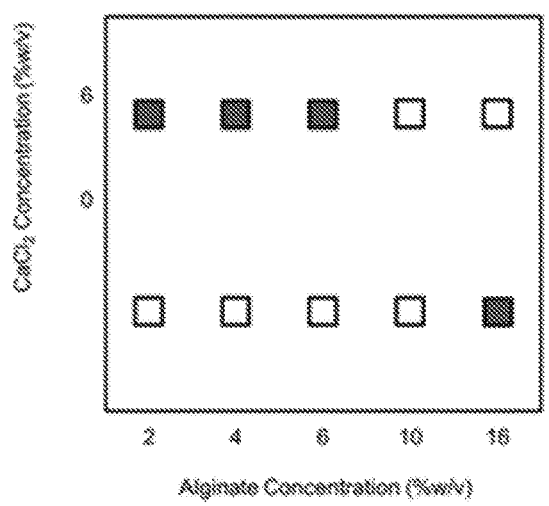
FIGS. 25A-25C are graphs illustrating the printability of high concentration alginate using the coaxial nozzle system of FIGS. 22A and 22B, and the effect of printing speed and alginate flow rate on fiber diameter and surface-to-volume ratio of the hydrogel fibers.
Figure 25B:
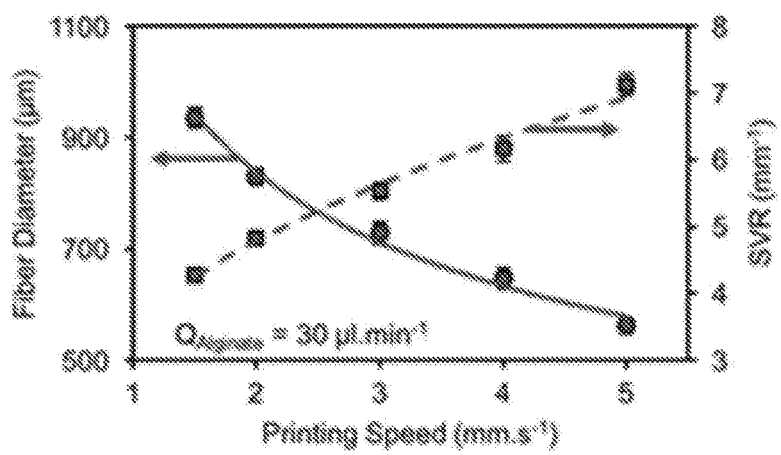
Figure 25C:
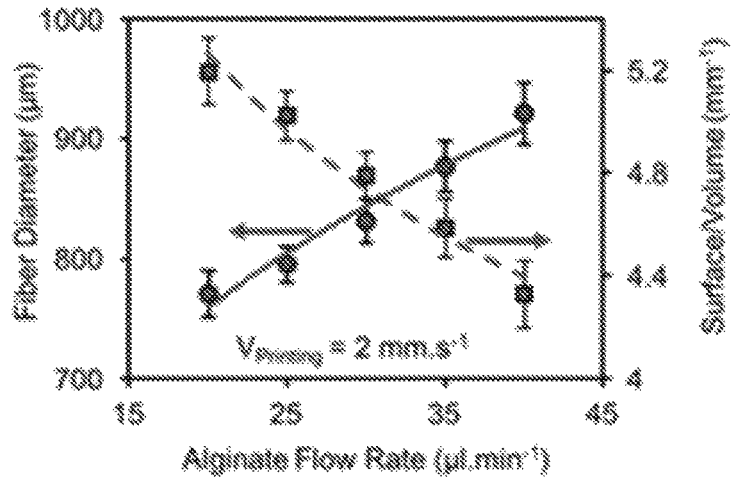

Delivery elements configured as drug-eluting scaffolds were fabricated with two different printing strategies. The co-axial needle setup may be used to print the structures. In another method, a two-step process was employed in which the gel was first deposited on the printing bed using a single-needle extruder and then was crosslinked by placing a drop of $CaCl_2$ solution on top of the construct. FIG. 25A summarizes the printability of each printing method, indicating that low-concentration alginate (2%-6% w/v) was printable using the one-step process while high-concentration alginate (>10% w/v) was printed using a two-step strategy. Fiber diameter and SVR ratio for 16% w/v alginate were measured using various flow rates and printing speeds. Similar to the low-concentration alginate, the SVR decreased at higher injection rates and slower printing speeds (FIGS. 17B and 17C).

Figure 17D:
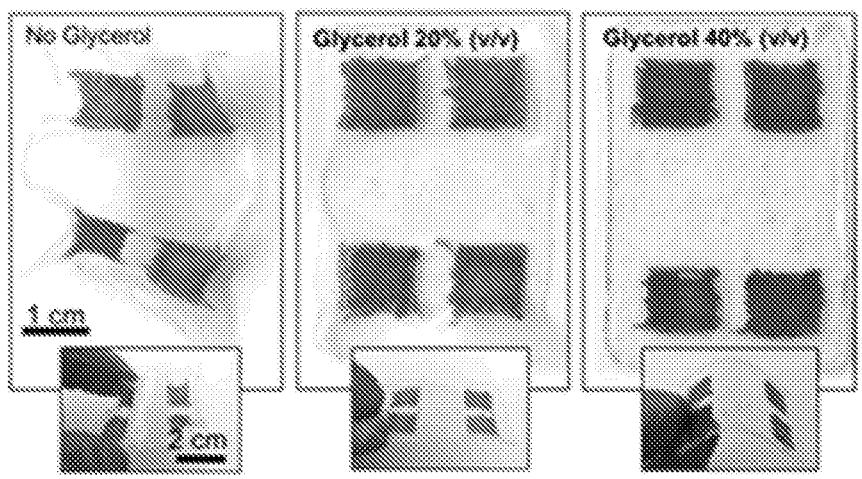
FIG. 17D illustrates embodiments of wound coverings comprising various concentrations of glycerol.
Figure 17E:
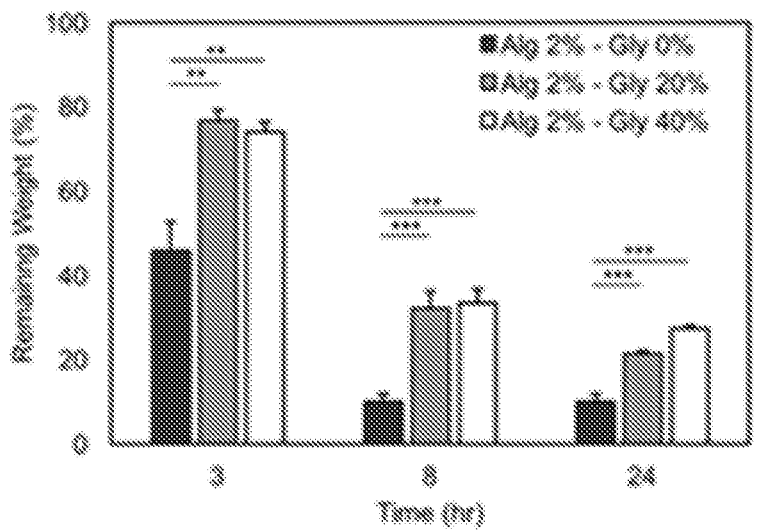
FIG. 17E is a bar chart illustrating dehydration rates for wound coverings comprising various concentrations of glycerol.
Figure 17F:
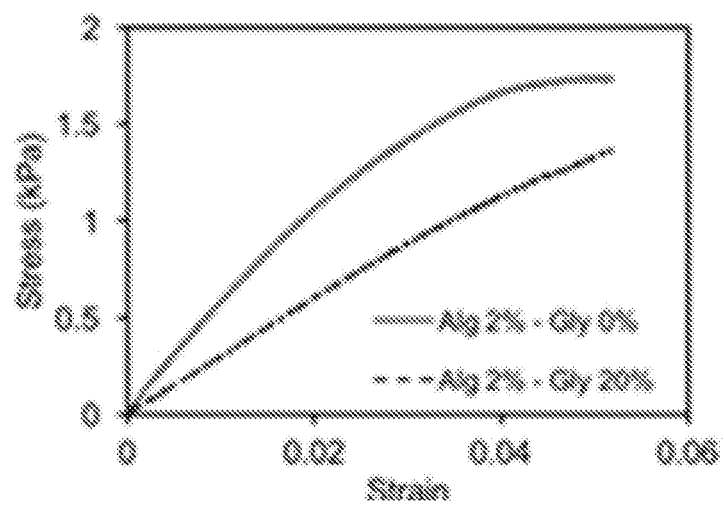
FIG. 17F is a stress-strain curve for wound coverings made from pure alginate and alginate-glycerol blend.
Figure 26A:
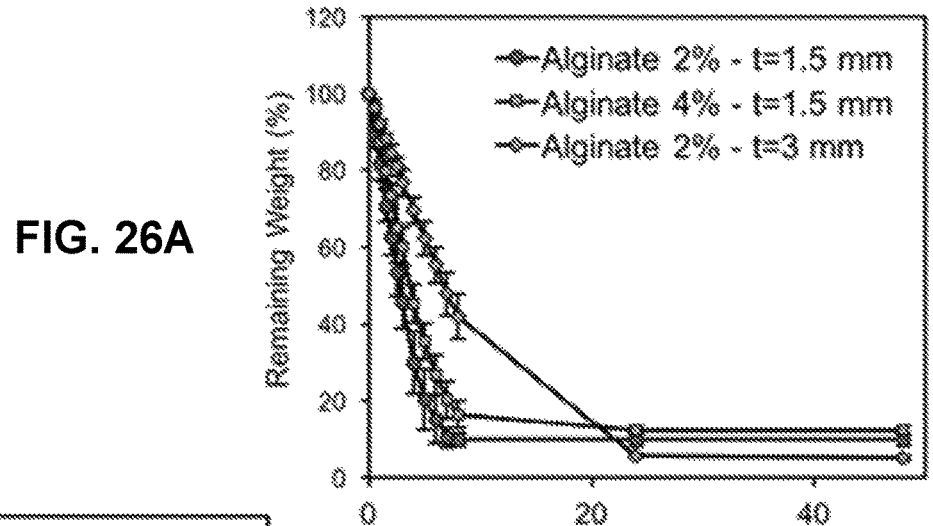
FIG. 26A is a graph illustrating the dehydration rate of a wound covering as a function of alginate concentration and dressing thickness.
Figure 26B:
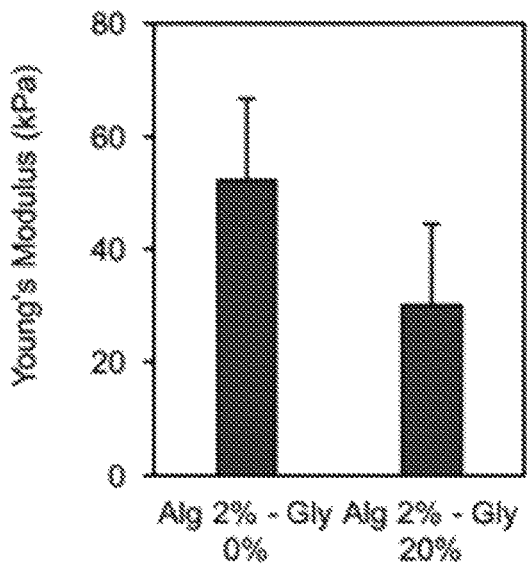
FIG. 26B is a bar chart illustrating the Young's Modulus of wound coverings made from pure alginate and alginate-glycerol blend.

One of the main advantages of using hydrogels as a substrate for wound dressings is their ability to retain moisture at the wound site. However, hydrogels may be prone to rapid dehydration, which can compromise the integrity of the dressing and ultimately affect its functionality. Rapid dehydration of the hydrogels can pose a challenge for the clinical application of gel-based dressings. The dehydration rate of the dermal patch was evaluated by measuring its weight loss at 37° C. and it was observed that the alginate patch was completely dehydrated in less than 10 hr (FIG. 26A). Influential parameters on dehydration rates including alginate concentration and dressing thickness were altered for these experiments. The dehydration rate was slower when alginate concentration increased from 2% to 4% w/v and patch thickness doubled from 1.5 mm to 3 mm (FIG. 26A). Blending glycerol with alginate reduced the dehydration rate of the patch significantly and improved its flexibility (FIGS. 17D and 17E). While the alginate dressings lost more than 50% of their weight in 3 hr, those made from alginate and glycerol only lost 20% of their initial weight during the same period (FIG. 17E). Although addition of glycerol slightly reduced the Young's Modulus of the dressing (FIG. 26B), it improved the stretchability of the dressing (FIG. 17F).

Figure 17G:
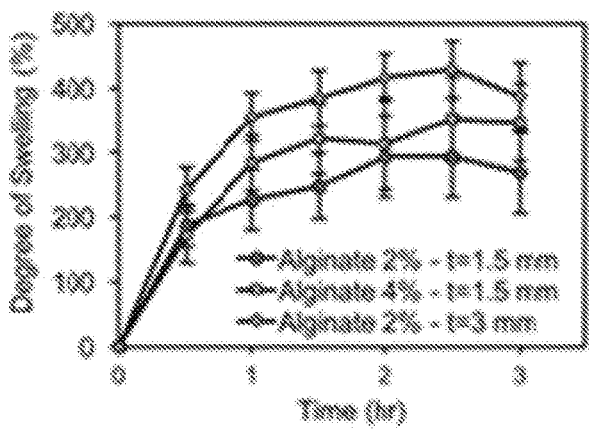
FIG. 17G is a graph illustrating the degree of swelling of wound coverings as a function of alginate concentration and thickness.
Figure 17H:
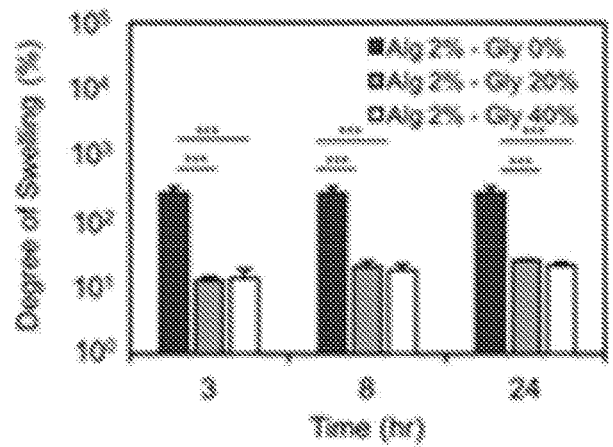
FIG. 17H is a bar chart illustrating the degree of swelling over time for wound coverings comprising various concentrations of glycerol.

The swelling behavior is another parameter in the design of dressings that may determine the capability of the dressing to absorb the exudates and keep the wound moist. Additionally, the patches are lyophilized for storage and transport and can be hydrated in an aqueous medium prior to use. Therefore, the swelling test can provide the required time for the dressing to reach equilibrium. The swelling property of the disclosed hydrogel-based dressings was evaluated by soaking lyophilized patches in phosphate buffered saline (PBS) and measuring their weight over time. The swelling degree of the dressings was examined for different thicknesses and hydrogel contents (FIG. 17G). Thicker dressings exhibited higher swelling degrees while the effect of alginate content was found to be insignificant. Moreover, the time needed for the dressings to reach equilibrium was about 2 hr and was independent of the thickness and alginate content of the dressings. Almost an order of magnitude reduction was observed for the dressings that were made from a glycerol and alginate as compared to those that were made from alginate alone (FIG. 17H).

Moisture control can be an important parameter for promoting the healing process in wounds (21, 22). The control of evaporative water loss in addition to the ability of the dressing to absorb wound exudate can therefore be accounted for in the design of a proper dressing. A water vapor transmission rate (WVTR) assay was performed to quantify the amount of water vapor that can pass through the alginate dressing. The effect of blending glycerol with alginate and covering the dressing with a silicon-based membrane was determined on the WVTR (FIG. 26C). The results showed that the dressing that were made from pure alginate had the WVTR of 8252±1167 $gr/m^2$/day, while those that were made from a blend of alginate and glycerol exhibited a slightly higher WVTR of 8665±1011 and 9077±1184 $gr/m^2$/day for 20% and 40% w/v glycerol contents, respectively (FIG. 26D).

The biocompatibility of the materials used in the fabrication of the wound coverings described herein can be an important factor for the clinical application of the dressing as wounds can be potentially exposed to toxic agents that may exacerbate the healing process. Alginate and glycerol are biocompatible materials that can be used for epidermal applications (19, 23, 24). Cabbage juice is a natural compound that is extracted from red cabbage. Although Brilliant Yellow was conjugated to anion-exchange beads and the beads were trapped in alginate fibers, a Live/Dead assay on skin fibroblasts was conducted to ensure the cytocompatibility of the dressing. High cell viability confirmed that the dye did not leach out of the beads and hydrogels (FIG. 27).

Interfaces to a Smartphone and Image Processing

Color-changing sensor arrays were characterized using ImageJ image processing software and a smartphone application. Photographic images of the sensors that were exposed to pH buffer solutions in the range of 4.00 to 9.18 were taken every 10 seconds (FIG. 28A). These images were then used to generate color data curves for quantifying the pH values. Brilliant Yellow sensors turned orange and red under acidic and alkaline conditions, respectively (FIG.

Figure 18A:
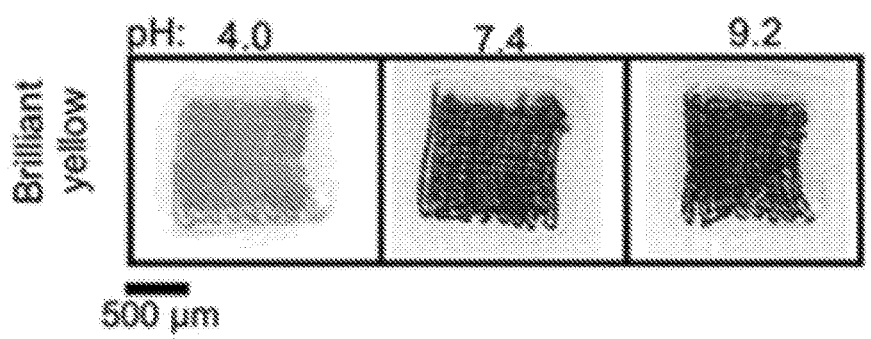
FIGS. 18A and 18B illustrate color changes of sensor elements comprising Brilliant Yellow and cabbage juice, respectively.
Figure 18B:
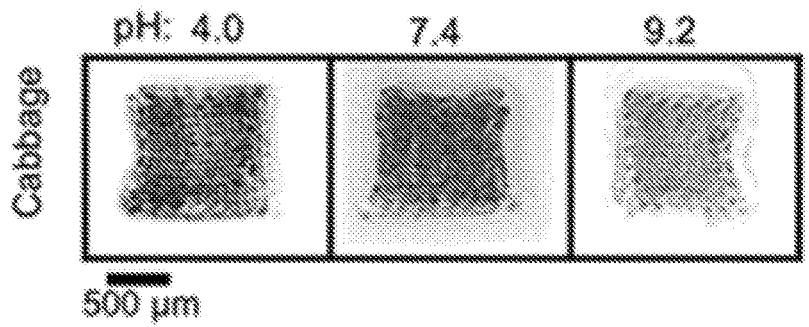
Figure 18C:
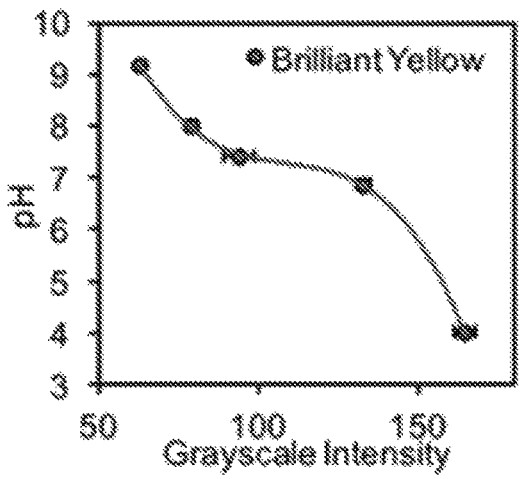
FIG. 18C is a graph illustrating a calibration curve showing grayscale intensity of a sensor element comprising Brilliant Yellow as a function of pH.
Figure 18D:
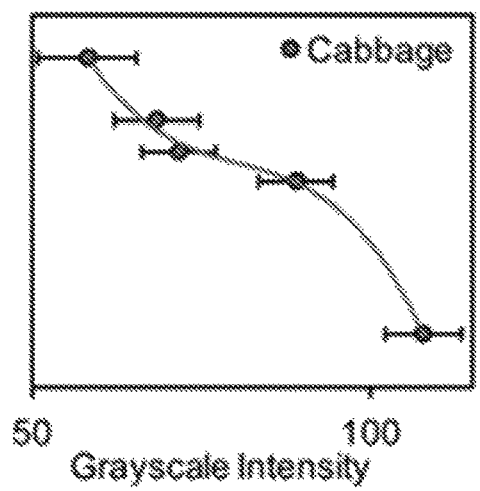
FIG. 18D is a graph illustrating a calibration curve showing grayscale intensity of a sensor element comprising cabbage juice as a function of pH.
Figure 28C:
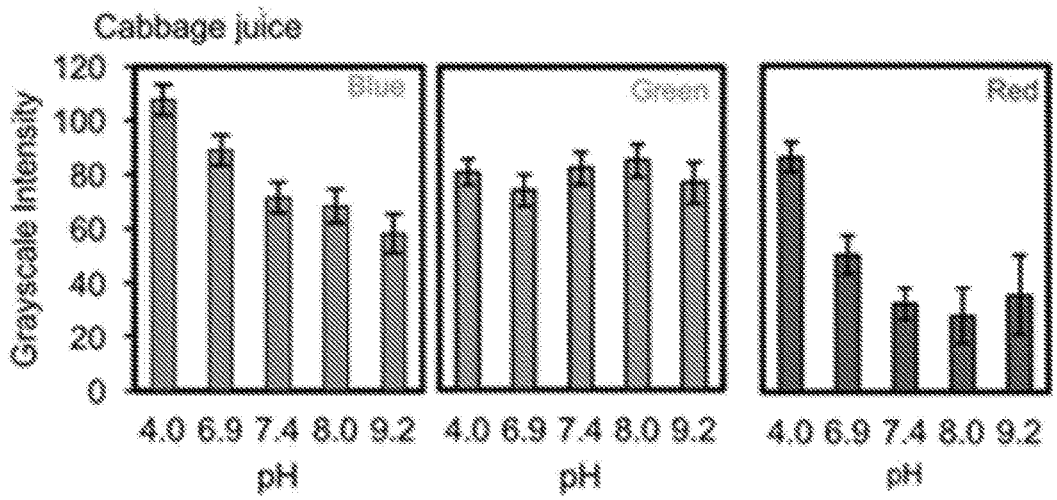

18A). The color of sensors that were made from cabbage juice changed from purple to green in acidic and alkaline conditions, respectively (FIG. 18B). The image-processing analysis was conducted by importing the recorded images in ImageJ and measuring the grayscale intensities of the red, blue, and green channels for each sample. The intensities in all channels decreased with increasing pH in sensors made from Brilliant Yellow; blue and red channels had the lowest and highest changes, respectively (FIGS. 18A-18K). For the sensors that were made from cabbage juice, the response of the green channel to pH variation was monotonic and the red channel did not follow a trend, while the blue channel represented a relatively consistent decreasing trend in its intensity when pH increased (FIG. 28C). Therefore, red and blue channels were used for producing the standard curves in Brilliant Yellow and cabbage juice, respectively. Overall, cabbage juice-based sensors had a more noticeable change in color when analyzed with the naked eye. On the other hand, Brilliant Yellow-based sensors had a larger difference in channel intensity, which can be a desirable characteristic for automated image processing. Brilliant Yellow sensors also had a significantly smaller variation in grayscale intensity under the same pH conditions, resulting in reduced standard deviations. Standard polynomial curves were fitted to the red and blue channels' intensity for Brilliant Yellow and cabbage juice sensors, respectively, with grayscale intensity on horizontal axis versus pH on vertical axis as shown in FIGS. 18C and 18D. These curves were used to determine the pH of the environment to which the sensors were exposed based on the grayscale intensity derived from analyzing their photographs.

Figure 18E:
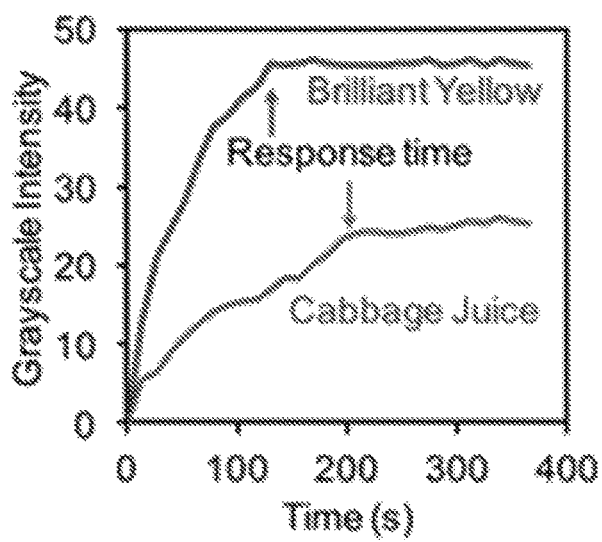
FIG. 18E is a graph illustrating the grayscale intensity and response time of sensor elements comprising Brilliant Yellow and sensor elements comprising cabbage juice.
Figure 18F:
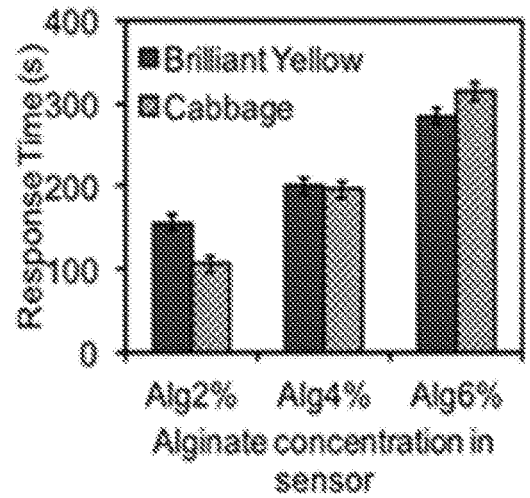
Figure 18G:
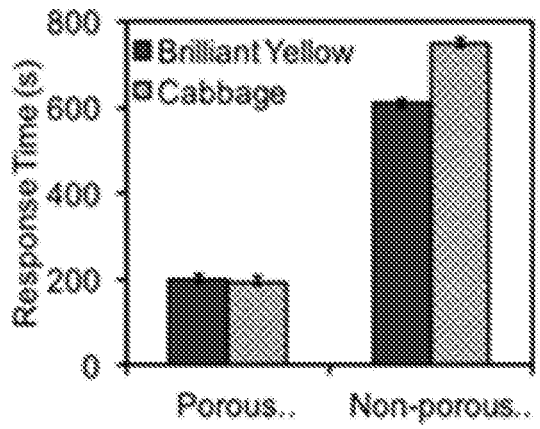
Figure 18H:
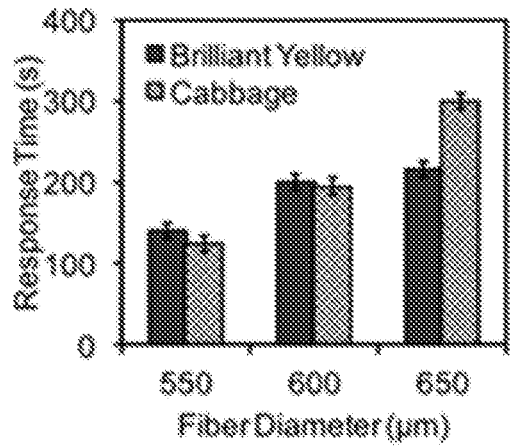
Figure 29A:
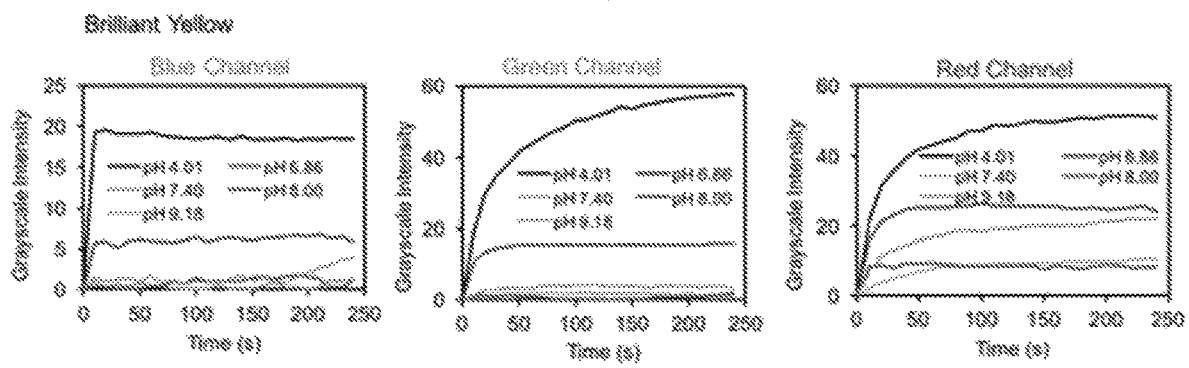
FIGS. 29A and 29B are graphs illustrating the grayscale intensity versus time in the blue, green, and red channels for sensor elements comprising Brilliant Yellow dye and cabbage juice.
Figure 29B:
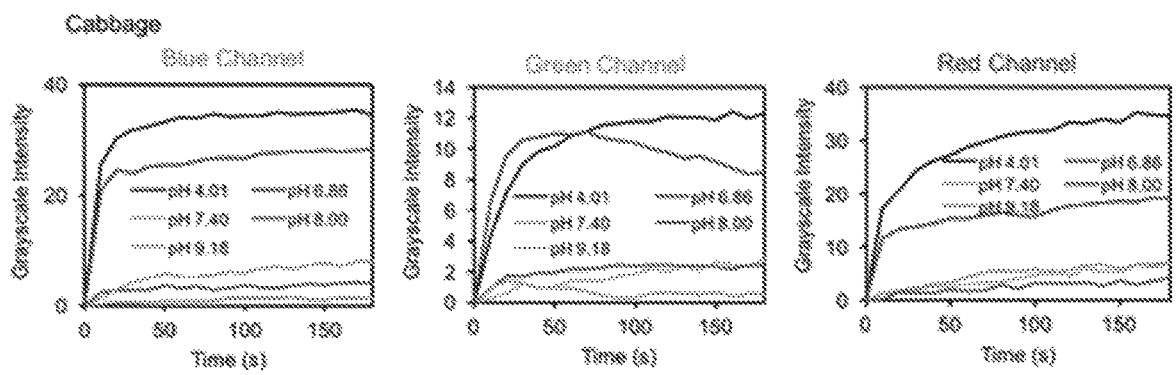
Figure 30D:
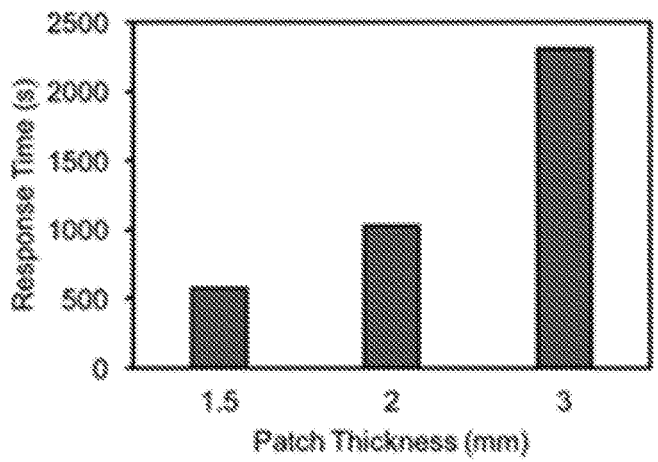
FIG. 30D is a bar chart illustrating response time for different thickness of the wound covering.

The effect of different design parameters including the (1) concentration of alginate in the sensors and in the dressing body, (2) thickness of the dressing body, and (3) SVR of the porous sensors, on the response time was evaluated. The red channel was considered for sensors made from Brilliant Yellow and the blue channel was considered for those made from cabbage juice. The time after which the sensors did not show any change in their grayscale intensity was considered as the sensor's response time (FIG. 18B). The response time of the sensors was generally fast and a result could be obtained in less than 5 minutes. No significant difference in the response time of the sensors was observed in different pH conditions (FIGS. 29A-29B). However, the concentration of alginate had a considerable influence on the response time of the sensors. In sensors made from Brilliant Yellow, increasing the alginate concentration from 2% to 6% w/v yielded an 85% increase in the response time (FIG. 18E). The effect of alginate concentration on the response time of the sensors made from cabbage juice was more pronounced, as sensors made from 6% w/v alginate had a threefold increase in response time when compared to 2% w/v alginate. Similarly, altering the patch structure by changing the alginate content from 2% to 6% w/v resulted in a considerable response time change from 200 s to 730 s and 610 s to 1000 s for Brilliant Yellow and cabbage juice, respectively (FIG. 18F). Such increase in the response time could be attributed to the lower porosity and smaller pore size of the alginate at higher concentrations, which hinders the diffusion of $H^+$ ions through the hydrogel. We also investigated the effect of porosity on the response time of the sensors. Non-porous sensors were made from square sheets of alginate gels with the same dimensions as the porous sensors. The results showed that porous sensors were considerably faster than the non-porous ones due to the enhanced transport of protons through the matrix, confirming our original hypothesis of using printed sensors (FIG. 18G). The effect of SVR on the response time of the sensors was also assessed (FIG. 18H). As the SVR increased by decreasing the fiber diameter, faster response times were achieved.

Figure 18I:
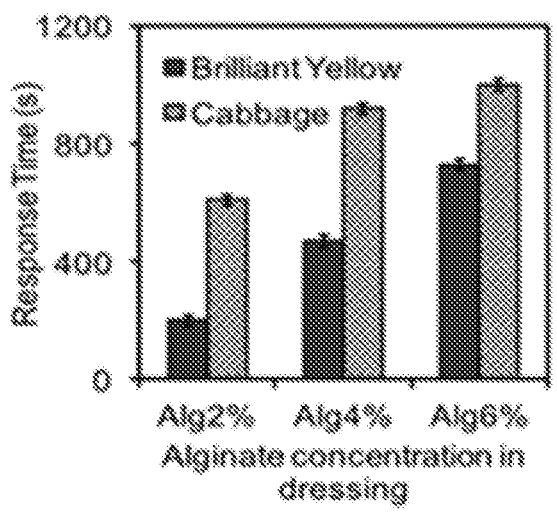
Figure 18J:
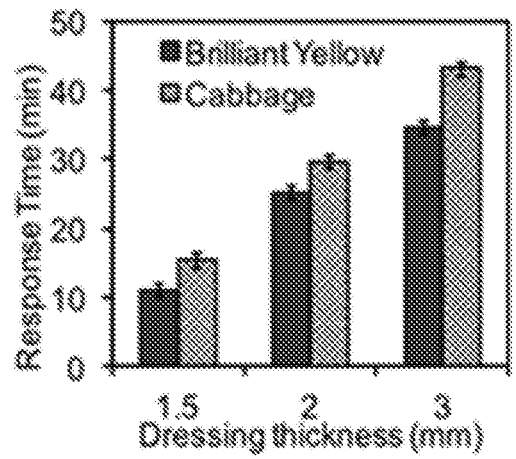

Another parameter that affected the response time of the sensors was the thickness of the dressing. Increasing the thickness from 1.5 mm to 3 mm resulted in threefold slower response times (FIG. 18I). Such increase in the response time could be attributed to the longer time that was required for thicker dressings to reach equilibrium condition as the $H^+$ ions were diluted in larger volumes compared to thinner dressings. This behavior was confirmed by analyzing the mass transport in the dressing numerically (FIGS. 30A-30D). Furthermore, the response time was found to be a function of the gel content in the dressing body. Increasing the alginate concentration from 2% to 6% w/v yielded significant increase in the response time of the sensors from less than 8 minutes to about 30 minutes (FIG. 18J). Blending glycerol with alginate further increased the response time of the sensors (FIG. 18K).

Colorimetric Detection of Bacterial Infections and Treatment of Infected Wounds

The performance of the wound coverings in the detection pH changes due to the growth of Gram-positive *S. aureus* and Gram-negative *P. aeruginosa* was evaluated. Both strains are highly prevalent in the wounds and infections caused by these pathogens remain a common complication in acute and chronic wounds[19]. The ability of the wound coverings described herein to detect pH changes due to bacterial activity visually and by taking images with a smartphone was assessed. Supernatants from the bacterial cultures were collected every one hour for 18 hours, and a droplet of the culture media was placed on the sensors. After 10 minutes, an image of each sample was taken by a smartphone camera for further quantification. For the samples that were collected from *P. aeruginosa* cultures, the pH was slightly acidic at the beginning (pH=6.5) and became more alkaline as the culture continued for 18 hours (pH=9.0) (FIG. 19A). However, the trend of pH change in *S. aureus* samples was the opposite, and the samples became more acidic up to 8 hours (pH-6.0) and then became neutral after 18 hours of culture (pH=7.0) (FIG. 19B). A visible color change was observed in sensors when the pH variations were more than one unit. This change was more pronounced in the sensors that were made from cabbage juice. However, smaller pH variations were not visually detectable.

Figure 19C:
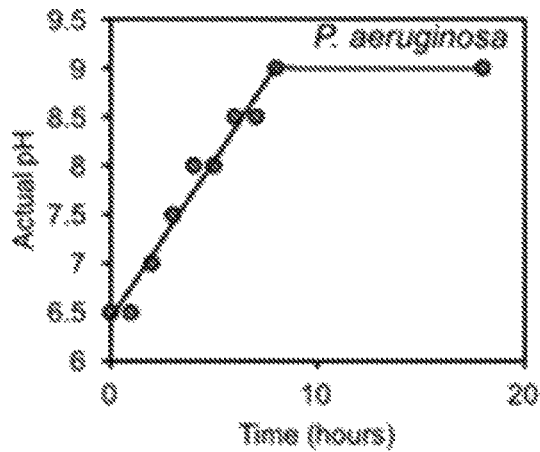
Figure 19D:
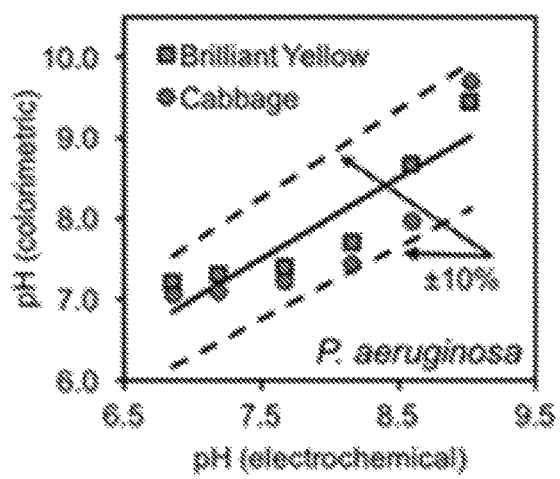
Figure 19E:
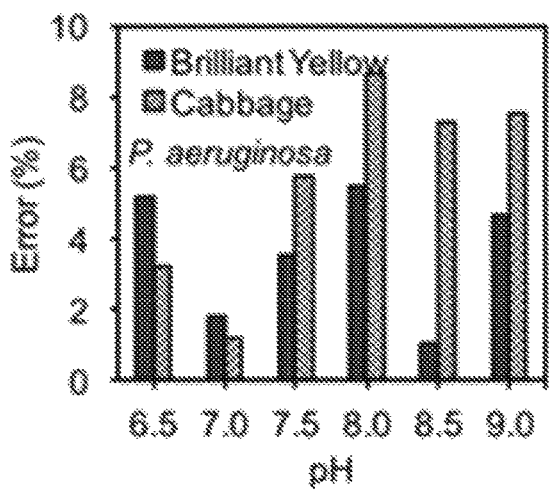
Figure 19F:
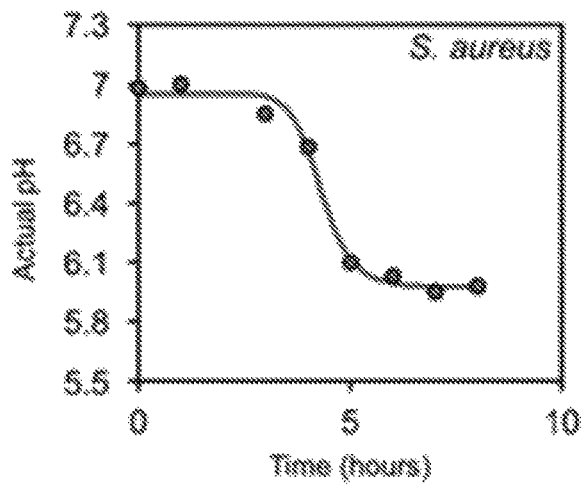

The recorded images were analyzed to quantify the color changes of the sensors that were exposed to bacterial cultures at different time points. After wirelessly collecting the images, digital image processing was performed in ImageJ to assess the variations in gray scale intensity in the red and blue channels for Brilliant Yellow and cabbage juice, respectively. An imaging box was used to achieve uniform environmental lighting. The actual pH of the solutions was measured using a commercial electrochemical pH probe as the reference. FIG. 19C shows the variation of the actual pH values in the samples that were collected from *P. aeruginosa* cultures. A linear increase in the pH was observed for the first 8 hours and the samples became more alkaline. The pH values changes in the range of 6.5-9. For this range, we achieved a ±10% accuracy for the colorimetric readings compared to the reference pH values that were measured by the electrochemical probe FIG. 19D. While the color change in the sensors with cabbage juice was more visible to the human eye, Brilliant Yellow yielded more accurate pH measurements, with an error of below 4% compared to an error of 9% from the cabbage juice sensors, as indicated in FIG. 19E. pH variations in the samples collected from *S. aureus* cultures were analyzed using a similar colorimetric method and compared with the reference electrochemical values. Samples from *S. aureus* cultures were more acidic and were in the range of 6-7.5. However, the trend was different than *P. aeruginosa* as the pH did not change significantly for the first three hours, then dropped about one unit in two hours, and finally reached a plateau afterwards (FIG. 19F). The accuracy of the sensors was slightly lower in the acidic environment (FIG. 19G) with an error of less than 6% for Brilliant Yellow and less than 14% for cabbage juice, indicating a higher accuracy for Brilliant Yellow in acidic condition as well (FIG. 19H).

An ex vivo test was performed to demonstrate the ability of the wound coverings in the colorimetric detection of bacterial infection. Pig skins were inoculated with *P. aeruginosa* at different initial densities of $1.4 \times 10^5$, $1.4 \times 10^6$, and $1.4 \times 10^7$ CFU per $cm^2$. After 12 hours, the wound covering was placed on the infected skins and color change in the sensors was inspected visually and by using image processing approach. A clear color change was observed in infected samples, which was more pronounced in samples that were inoculated with higher initial bacterial densities (FIG. 20A). The increase in the pH of the infected skins were confirmed by commercially-available pH strips. A smartphone was also used to quantify the pH values of the infected skins (FIG. 20B) and compared these results with the readings of the pH strips (FIG. 20C).

To examine the antibacterial effectiveness of the drug-eluting scaffolds, a semi quantitative bacteria inhibition assay was performed using *P. aeruginosa*. To identify an effective dosage of gentamicin to completely eradicate the bacteria, scaffolds with the same volume were loaded with 50-300 mg/ml of the drug. Scaffolds with no drugs and filter paper impregnated with the same amount of drugs were used as negative and positive controls, respectively. Gentamicin is widely used as an effective antibiotic agent against a wide range of Gram-negative and Gram-positive bacteria, including *P. aeruginosa* (25-27). The results suggested that the loading dosages of less than 200 mg/ml may not be effective in eradicating the bacteria (FIG. 20D). Scaffolds with a loading dosage of 200 mg/ml formed a ring which outlined the inhibited zone around the drug-eluting patch, while the areas under both control patch regions still had bacterial growth. The observed white ring around the scaffold within the inhibited zone was suspected to be infected by the bacteria. Therefore, we collected swab samples from three different zones near the scaffold (point 1), in the white region (point 2), and at the edge of the ring (point 3), then plated the samples overnight on another agar plate. FIG. 20E demonstrates that there were no bacteria within proximity of the patch and few colonies of bacteria formed in point 2, while a large number of colonies formed from the samples collected at the edge of the ring. These results are consistent with typical drug diffusion within agarose gel that leads to higher concentrations of the drug at the vicinity of the scaffold and lower concentrations away from the scaffold. The formation of the white ring around the scaffold can be attributed to the interaction of the phosphate ions in the agar and calcium ions that were releasing from the calcium alginate scaffolds. Then negative controls (scaffolds with no drugs) did not inhibit the bacterial growth while the positive control (drug+filter paper) formed a clear inhibition ring around the filter paper (FIG. 20F).

Integration of Wound Coverings with Commercial Dressings

Figure 21A:
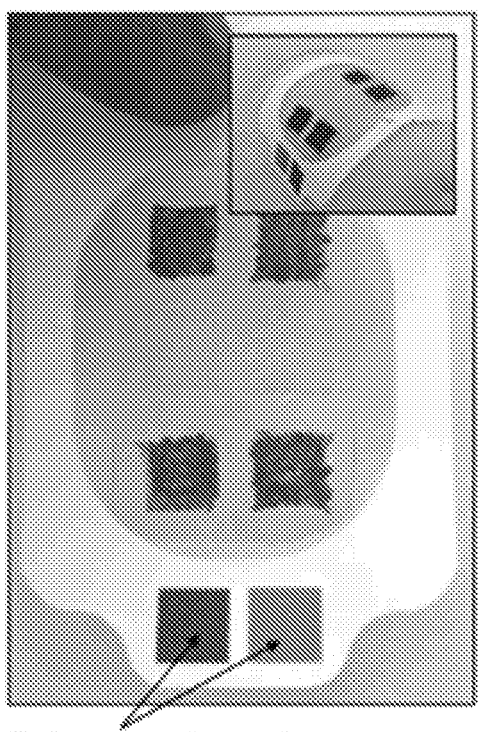

The ability to integrate the wound coverings described herein with commercial dressings was assessed. FIG. 21A shows a fabricated hydrogel dressing attached to a Mepitel® dressing. Mepitel® is a wound dressing with contact layer that has a transparent silicon mesh that allows the transport of oxygen to the wound site, while reducing the evaporation rate from the wound. Moreover, the transparency of the thin membrane enables colorimetric detection of pH variations in the wound. Furthermore, this dressing contains an adhesive layer that ensures proper attachment of the dressing to the tissue. These dressings are flexible and can conform to the curved surfaces of the skin (FIG. 21A, inset).

Figure 21B:
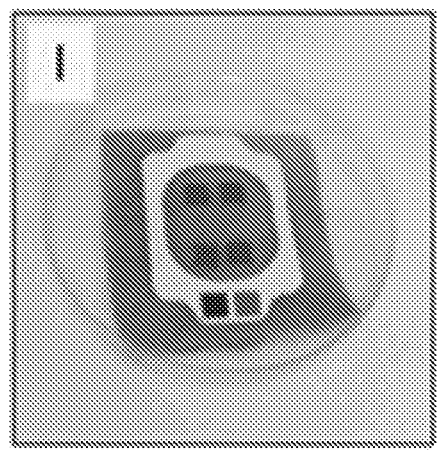
Figure 21C:
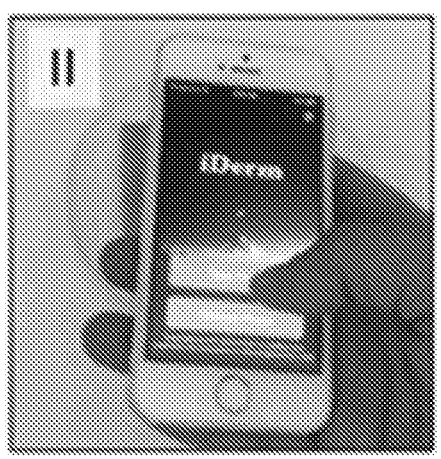
Figure 21D:
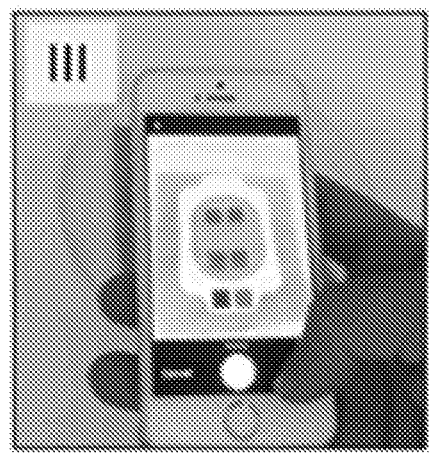

An in-house application (called "iDerm") was developed and used to record color changes in the sensors and convert them into quantitative data. FIG. 21B shows the process of taking images using a smartphone, selecting the sensors by the user, and displaying the final results on the screen. iDerm split the red, green, and blue channels and used a gray scale in the red and blue channels to quantify the pH values for Brilliant Yellow and cabbage juice sensors, respectively. Reference color markers (blue and red) were used to eliminate the dependence of the results on different lighting conditions, which may occur in practical applications. A long touch feature was designed in the application that allowed the user to select each sensor by holding a finger on the image of the sensor on the screen for few seconds. A graphical user interface was designed to display the final results on the screen and record the pH values for continuous monitoring of the wound condition. The recorded data were uploaded on a secure cloud storage drive that allowed the medical personnel to access the patient data and monitor the wound condition in real time.

Figure 31A:
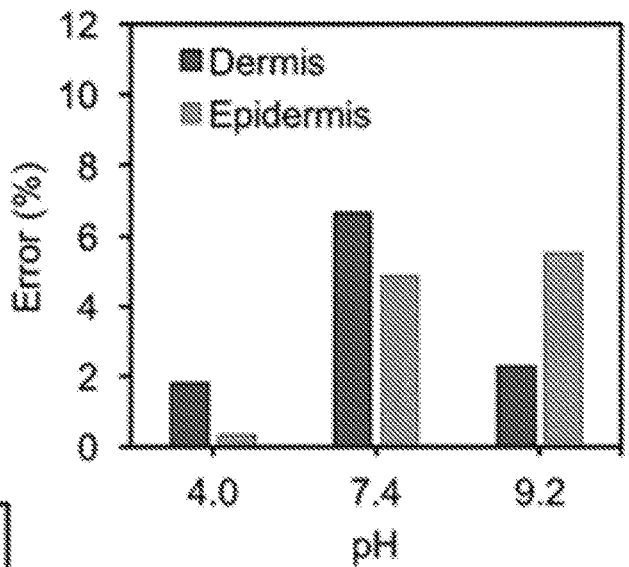
FIGS. 31A and 31B are bar charts illustrating error evaluation of colorimetric pH measurement on pig skins using the wound coverings described herein.
Figure 31B:
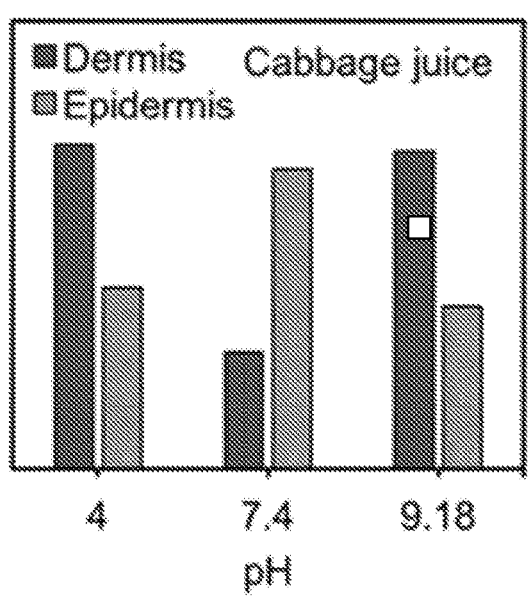

Red and blue color markers were used as references to eliminate the dependence of the readings to environmental lighting in practical conditions. We evaluated the ability of the sensors to detect pH variations on biological tissues by placing the Mepitel®/hydrogel dressing on pig skins, which were sprayed with different buffer solutions (FIG. 21H). Color change was visible between the acidic, neutral, and basic conditions. However, more accurate results were obtained through the use of smartphone image acquisition and image processing. The dressing was placed on the epidermis and dermis layers of pig skins to investigate the effects of tissue color on the readings. The errors in readings in dermis and epidermis were below 10% and did not depend on the color of dermis and epidermis layers (FIGS. 31A and 31B).

Figure 21I:
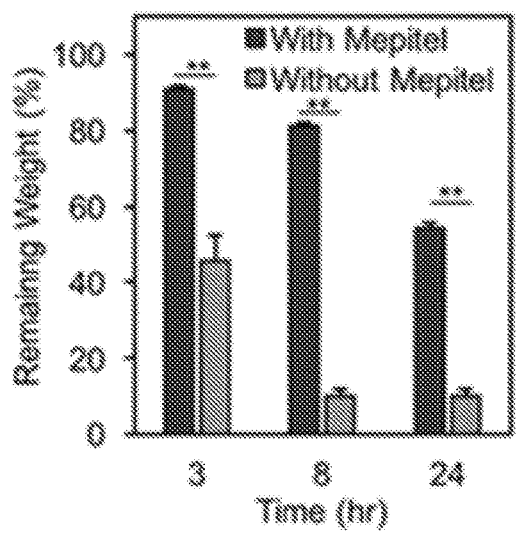
FIG. 21I is a bar chart illustrating dehydration of wound coverings including an outer polymeric layer.

The effect of Mepitel® on the dehydration rate of the hydrogel dressing was studied. Dressings with 2% w/v alginate were covered by Mepitel® and their weight were measured in 24 hr. The effect of Mepitel® on the dehydration rate of the hydrogel dressings was significant (FIG. 21I). Hydrogel dressings that did not have Mepitel® lost 90% of their water content after 24 hours, those that were covered by the commercial dressing only lost 50% of their water content. Furthermore, covering the dressing with Mepitel® significantly reduced the WVRT to 2218±52 $gr/m^2/day$.

DISCUSSION

The multifunctional dressings described herein represent a colorimetric pH sensing array and drug-eluting scaffold that can be used for detecting and treating infections at the wound site. Compared to existing wound dressings, the wound coverings described herein are unique in the sense that they have both diagnostic and therapeutic components integrated into a single dressing. Such multifunctional dressings can generate significant savings in healthcare costs, due to reduced clinical inspection time, the elimination of the unnecessary changing of dressings in patients that are suspected to have infections, and shorter hospital stays resulting from faster wound healing. Additionally, higher dosages of the antibacterial agent can be used without imposing adverse side effects to other organs due to the localized delivery of the drug at the site of injury. The introduced dressing is composed of alginate and glycerol, which are approved by the US Food and Drug Administration (FDA) for wound healing applications (28). The addition of hydrogels helps maintaining a moist environment for the wound and promotes the healing process by up to 50% compared the wounds are only exposed to air (29). Additionally, the wound coverings described herein can be integrated within a commercially-available dressing such as Mepitel® and placed on the wound without chemical or physical irritation.

The soft mechanical properties and ability for the wound covering to conform to biological surfaces with irregular curvatures were analyzed. Moreover, the biocompatibility of the constituent materials, antibacterial properties, and hydration and evaporative characteristics of the dressing were studied. The ability to digitally analyze colorimetric responses as well as integrate the wound covering within commercially-available dressings was also realized. First, the fabrication process of the sensors and their ability for colorimetric detection of pH variations due to bacterial infections were systematically investigated. Using porous sensors can yield to faster response times due to the higher available SVR. Three-dimensional printing was used in this work as a versatile approach for fabricating complex structures in a high-throughput manner (30). This method enabled the porous sensors to be printed in less than a minute. The ability to print sensors allows scaling up the process for making large-scale dressings that can cover larger wound areas. The SVR of the fabricated sensors was a function of the diameter of fibers and the spacing between them. The diameter of the fiber can be altered by adjusting the flow rate of extruded alginate and the nozzle translational speed. Increasing the flow rate of the extruded alginate resulted in the deposition of more material from the print head, which resulted in fibers with larger diameters. In contrast, increasing the nozzle speed resulted in smaller fiber diameters as less material was deposited per unit length of the fibers. A similar trend was reported by others in previous studies (31, 32). Another parameter that affected the diameter of the fibers was the density of the encapsulated color-changing beads. The results suggest that higher concentrations of the beads result in a decreased fiber diameter. Higher concentrations of the bead resulted in stronger signals, which facilitated the colorimetric detection of the pH variations.

In bacterial infections, the variation of pH depends on the species. For example, it was demonstrated that the pH of *P. aeruginosa* cultures increased as the bacteria was growing while the pH decreased with culture time for *S. aureus*. *S. aureus* is a facultative anaerobe and grows best in an aerobic environment. Its metabolism is both respiratory and fermentative and can ferment a variety of carbohydrates (like glucose) to produce acidic end products (33). *P. aeruginosa*, on the other hand, is not fermentative and has a strictly aerobic respiration. It utilized peptones in the media to produce alkaline end products (34). In current practice, the dressing is changed on regular-basis, swab samples are collected in suspected patients, and the patient is treated with systemic antibiotics to prevent possible infections (29). However, this method is painful, time consuming, and labor-intensive. The wound coverings described herein use pH as a marker of bacterial infections and utilize a colorimetric method with the ability to interface with computing devices such as smartphones. This approach enables the healthcare personnel or the patient to monitor the pH of the wound over time and change the dressing when infection is detected.

For the fabrication of the sensors, ion-exchange beads were doped with pH indicators that undergo a color change in response to the variation of the acidity of the environment. The electrostatic interaction between the dye and the beads minimized the leakage of the dye from the beads (35). Encapsulation of the beads within the hydrogel fibers can ensure that the beads do not contact the skin and disperse within the wound site. Using this method, pH values in the range of 4.0-9.0 were visually detectable by means of a smartphone. Although the sensitivity of visual detection was one pH unit, analyzing the images taken by smartphones improved the sensitivity to less than 0.5 pH units. Such sensitivity could be potentially used for early detection of bacterial infection in the first few hours (according to our data shown in FIGS. 20A-20F). Sensitivities as small as ±5% (maximum ±0.45 pH units for the pH of 9.0) were achieved when the measured values were compared to the readings of an electrochemical pH probe. The effect of design parameters including the fiber diameter, concentration of alginate, and the thickness of the dressing on the response time of the sensors was characterized. The fastest response times achieved in this work was 5 minutes and this time was increased due to higher diffusive barriers against the transport of ions within the sensors as the fiber diameter, hydrogel concentration, and the thickness of dressing increased (FIGS. 18A-18K). It is noteworthy that the response time of a non-porous sensor was significantly higher than the printed sensor by a factor of three, which confirmed our hypothesis in using porous sensors.

The ability to uptake the body fluid can be important for the maintenance of the moist wound environment (36). Hydrogels are polymeric networks that can uptake water up to thousands of times of their dry weight (37), therefore they are considered as suitable dressing materials for wound management. Among all hydrogels, alginate is a naturally-derived polysaccharide that has been extensively used for drug delivery, tissue engineering, and wound dressings (14, 18, 38). Alginate is a natural hemostat that can be used to prevent bleeding at the wound site. This hydrogel also does not adhere to tissues; thus, removing the dressing from the wound does not cause much trauma, and reduces the pain experienced by the patient during dressing changes (16). However, alginate dehydrates rapidly and loses its flexibility upon dehydration. Therefore, we added glycerol to alginate reduce the dehydration rate by 30%. Moreover, dressings that were made from glycerol maintained their mechanical integrity and flexibility after complete dehydration. When the wound coverings described herein were combined with Mepitel®, the rate of dehydration was significantly decreased due to reduced evaporation caused by the silicon membrane of the commercial dressing. Therefore, combined covering/Mepitel® dressing holds great promise for treatment of chronic wounds as it can stay on the wound over long periods without need for change.

Diagnostics and effective management of an infection is critical for the success of any wound dressing. Current dressings with antibacterial properties do not have the ability to detect infections at the wound site. As a result, visual inspection of the wound condition by skilled personnel is needed, which is cumbersome, painful, and requires the change of dressings on a daily basis. The proposed multifunctional dressing is capable of measuring pH as a marker of bacterial infection and delivering antibacterial agents. An image processing application (iDerm) was developed that records the digital images of the wound covering and reports the pH values. iDerm enables the patient to record the wound condition at home and relay the information to the healthcare personnel, who can make decisions on the subsequent treatment strategies. The ability of the disclosed wound coverings in the colorimetric detection of bacterial infections was demonstrated using in vitro and ex vivo tests. First, two prevalent strains of bacteria that are found in infected wounds. i.e., *P. aeruginosa* and *S. aureus*, were cultured, and the pH of the culture medium was measured over 18 hours using the wound covering and a commercially available probe. The wound covering was able to detect pH variations in the culture media with less than ±5% error, indicating the accuracy of our colorimetric approach. Then, pig skins were infected with bacteria for 12 hours and the pH changes on the samples were measured using GelDerm and commercially-available pH strips. A clear change in the color of the sensors was observed in the infected skins as compared to the control. This color change was more substantial in samples that were infected with higher initial inoculation density of the bacteria.

Topical delivery of antibiotics minimizes the complications of intravenous administration of the drug and offers the advantage of delivering increased drug concentrations directly to the wound site. Gentamicin, which has a wide spectrum of activity against most bacteria strains that are found in infected wounds, was encapsulated in the drug-eluting scaffolds (39). The rationale behind using drug-eluting scaffolds was to provide a more localized delivery of the drug at the interface of the wound and dressing. The in vitro inhibition assay for *P. aeruginosa*, as a model bacterium, demonstrated the effectiveness of the topical delivery of gentamicin at 3 mg/ml dosage. These dressing also showed no toxicity in contact with human primary keratinocytes and fibroblasts, making them a suitable candidate for treatment of dermal injuries.

Overall, the proposed technology holds great promise in managing chronic and acute injuries caused by trauma, surgery, or diabetes. The ability to diagnose and treat the infections at the site of injury reduces manual inspection of the wound and systemic administration of antibiotics to the patients. With the formulation that used in the design and fabrication of the proposed multifunctional dressing, it can be lyophilized, and sterilized for long-term storage without losing flexibility, antibacterial efficacy, and ability to detect pH changes at the wound site. The performance of this system may be further improved by integrating more sensing elements within the dressing to detect more specific bacterial markers. Biomaterials that possess stronger mechanical properties in terms of flexibility and moisture management for longer periods may also be used.

Materials and Methods

Preparation of brilliant yellow and cabbage juice loaded beads: 135 mg of Brilliant Yellow dye (TCI, Tokyo, Japan) was dissolved in 6 ml Ethanol, 24 ml of DI water were then added, and solution was stirred for 30 minutes. Cabbage juice was prepared by adding 15 g of chopped red cabbage to 30 ml of DI water, keeping at 90° C. for 1 hour, and filtering to obtain approximately 30 ml of the final solution. 3378 mg of Dowex 1×4 chloride form (Sigma, St. Louis, USA) was added to 50 ml of DI water in a Falcon® tube, it was manually stirred, then settled until the beads were at rest on the bottom of the tube. The water content was carefully extracted with a pipette and replaced. This step was repeated twice with DI water and once with Anhydrous Ethanol. After washing, 30 ml of DI water was added to the beads and the obtained suspension was added to the dye solution (Brilliant Yellow solution or cabbage juice). Supernatant was washed multiple times to obtain a clear supernatant.

Preparation of alginate solutions for sensors and drug-eluting scaffolds: For sensors, DI water was added to pH-sensitive beads to reach the final volume of 15 ml. For drug-eluting scaffolds, desired amount of gentamicin sulfate (according to the drug content in the final scaffold) was added to 5 ml of DI water. Sodium Alginate (Sigma, St. Louis, USA) were then added to both bead suspension and drug solution to achieve the desired concentration, kept at 60° C. for 1 hour, and vortexed periodically at 3000 rpm.

3D printing and characterization of sensors and drug-eluting scaffolds: A commercial 3D printer (Prusa i3) was modified by incorporating a microextruder to print hydrogel fibers. To print alginate 2-6% w/v, a microextruder that included a coaxial needle system powered by two syringe pumps (Harvard Apparatus) to deliver Alginate with different concentration (90 µl/min) and $CaCl_2$ (6% w/v, 30 µl/min) (Bio Basic Inc., Toronto, Canada) solutions. Alginate was ionically crosslinked at the tip of the extruder and deposited on the 3D bioprinter's bed. A single extruder was used for printing 16% w/v alginate with a flow rate of 22 µl/min and 5 mm/s printing speed in normal condition. Mentioned flow rates and printing speeds were altered for characterization based on different parameters. Printed scaffolds were then observed under a light microscope (Olympus IMT-2, Tokyo, Japan) to measure the individual fiber diameters.

Analysis of pH-sensitive sensors' response to different pH environments: For testing the response time and RGB color intensity of the pH sensitive components, a light diffusing box was built, with a camera on top that took a photo automatically in 5 second intervals. This device was used to test pH sensors with different properties such as alginate concentrations, fiber diameters, and pH of the solutions that the sensors were exposed to. The individual images were then analyzed using ImageJ software. The images were converted to grayscale format of each individual RGB channels and their change in intensity was measured to determine the time for each sensor to reach a steady state condition.

Fabrication of the dressings: 1 ml of Alginate solution (2% w/v for normal condition) was spread on a cuboid 35 mm×55 mm×1.5 mm mold. 4 pH sensors were placed at the corners, and 2 drug-eluting scaffolds were placed at the center. 2 ml of Alginate solution (2% w/v) were then added to the mold; an agarose sheet (agarose 1.5% w/v, $CaCl_2$ 4% w/v) was placed on top and left for 20 minutes to crosslink. After removing the sheet, the crosslinked patch was removed from the mold.

Exposing the sensors to bacteria supernatant: A strain of *Pseudomonas aeruginosa* ATCC 10145 was cultured in Tryptic soy broth (TSB, Fluka Analytical), and 1 ml of the supernatant was collected every hour. 150 µl of each supernatant was deposited on different pH sensors to do the photography and subsequent assessments.

Ex vivo bacterial detection tests: Non-injured samples of human skin, were cut into four portions of area 25 $cm^2$, disinfected with 70% v/v ethanol and washed with saline solution. The skin portions were individually transferred into sterile Petri dishes. Before the inoculating skins with bacteria, swab samples were taken from skins and plated them on TSA plate for 24 hours to ensure that the skin samples were properly sterilized. An aliquot of 200 µl of an overnight culture of $P.$ $aeruginosa$ was deposited on the skins and distributed over the skin using a glass spreader. Four conditions of no bacterial infection (control) and three initial inoculation densities of $1.4 \times 10^5$, $1.4 \times 10^6$, and $1.4 \times 10^7$ CFU/cm$^2$ were considered.

The infected skins were then incubated at 37° C. in a moist atmosphere. After 12 hr, the wound dressing was placed on the samples and images were taken by a smartphone after 30 min to analyze the sensors.

For measuring pH one pig skin, buffer solutions with pH 4.00 (VWR Analytical), 6.86 (Fisher Scientific), and 9.18 (Fisher Scientific) were sprayed on three slices of pig skin. Patches of both types, Brilliant Yellow and cabbage juice, were put over the pig skin and photographic images were taken after 10 minutes for subsequent analysis.

Bacteria viability loss assay: Drug-eluting scaffolds were embedded in alginate patches as described previously; patches were then placed on top of a Tryptic soy agar (TSA, Sigma-Aldrich) plate on which $Pseudomonas$ $aeruginosa$ bacteria were spread and the effect of the antimicrobial was investigated after incubation at 37° C. for 18 hr.

Mechanical test: Rectangular alginate/glycerol sheets (20 mm×10 mm×2 mm) made of alginate 2% w/v and alginate 2% w/v+glycerol 20% w/v were prepared by crosslinking with agarose sheets containing $CaCl_2$ similar to preparation of the patches. The samples were kept in PBS and their tensile properties were measured using an Instron 5542 mechanical tester. The fibers were sandwiched between the grips and were stretched at a constant strain rate of (0.1 mm/min). The fibers were kept hydrated using an ultrasonic humidifier during the test, four samples for each type was tested. The Young's modulus was calculated using the slope of the stress-strain curve and the strain rate.

Dehydration and hydration tests: Square gel sheets (15 mm×15 mm) made of two different concentrations of alginate (2% and 6% w/v) and two different thicknesses (1.5 mm and 3 mm) were fabricated by crosslinking with agarose sheets containing $CaCl_2$ similar to preparation of the patches. Four samples of each condition were prepared for the dehydration and hydration test. The dehydration test was conducted by keeping samples in ambient room temperature, then measuring the weight during definite time intervals for 48 hr. The remaining mass was subtracted from its initial value for each sample. For the hydration test, samples were first frozen at −80° C. for 24 hours, lyophilized for 72 hours, weighted, and immersed in PBS. The weight was then recorded during definite time intervals for 3 hours and the degree of swelling was then obtained by determining the gained weight for each sample.

Cell culture: Human primary keratinocytes and fibroblasts were harvested according to the previously described method[21] from foreskin samples derived from healthy patients receiving circumcision. Keratinocytes were cultured in Keratinocyte serum-free medium (KSFM, Invitrogen Life Technologies, Carlsbad, CA) supplemented with epidermal growth factor (0.2 ng/ml, EGF, GIBCO) and bovine pituitary extract (25 ng/ml, BPE). Dulbecco's Modified Eagle's Medium (DMEM, GIBCO, Grand Island, NY) with 10% fetal bovine serum (FBS) were used to culture Fibroblasts. For all experiments in this study, Keratinocytes and fibroblasts at 4 to 7 passages were used.

Live/dead, viability/cytotoxicity assay: Cells were cultured in 6-well plates with density of $250 \times 10^3$ cells/well. Kyn or KynA with increasing concentration from 50 to 150 µg ml$^{-1}$ were used in the cell media. Cell viability was assessed using Live/Dead assay kit for mammalian cells (Invitrogen) by flow cytometry after 3 days of incubation. In this assay, dead cells and those in apoptosis stage are stained by ethidium homodimer (EthD-1), a red fluorescent nucleic acid dye. On the other hand, live cells can be observed by clacein AM which is turned to a green fluorescent compound by active intracellular esterase in live cells.

Statistical Analysis: One-way analysis of variance (ANOVA) with Tukey post hoc test were performed on experiments with more than 2 test groups. Standard deviation was the measure of uncertainty in all data. All statistical analysis and graphing were performed with the Microsoft Excel.

REFERENCES AND NOTES

1. M. H. Mohammadi, B. Heidary Araghi, V. Beydaghi, A. Geraili, F. Moradi, P. Jafari, M. Janmaleki, K. P. Valente, M. Akbari, A. Sanati-Nezhad, Skin Diseases Modeling using Combined Tissue Engineering and Microfluidic Technologies, Adv. Healthc. Mater. (2016).
2. D. Church, S. Elsayed, O. Reid, B. Winston, R. Lindsay, Burn wound infections Clin. Microbiol. Rev. 19, 403-434 (2006).
3. E. E. Tredget, H. A. Shankowsky, R. Rennie, R. E. Burrell, S. Logsetty, $Pseudomonas$ infections in the thermally injured patient, Burns 30, 3-26 (2004).
4. G. C. Bloemsma, J. Dokter, H. Boxma, I. M. M. H. Oen, Mortality and causes of death in a burn centre, Burns 34, 1103-1107 (2008).
5. D.-H. Kim, N. Lu, R. Ma, Y.-S. Kim, R.-H. Kim, S. Wang, J. Wu, S. M. Won, H. Tao, A. Islam, K. J. Yu, T. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, Epidermal Electronics, Science (80-.). 333, 838-843 (2011).
6. X. Huang, Y. Liu, K. Chen, W. J. Shin, C. J. Lu, G. W. Kong, D. Patnaik, S. H. Lee, J. F. Cortes, J. A. Rogers, Stretchable, wireless sensors and functional substrates for epidermal characterization of sweat, Small 10, 3083-3090 (2014).
7. A. H. Najafabadi, A. Tamayol, N. Annabi, M. Ochoa, P. Mostafalu, M. Akbari, M. Nikkhah, R. Rahimi, M. R. Dokmeci, S. Sonkusale, Biodegradable nanofibrous polymeric substrates for generating elastic and flexible electronics, Adv. Mater. 26, 5823-5830 (2014).
8. Y. Liu, J. J. S. Norton, R. Qazi, Z. Zou, K. R. Ammann, H. Liu, L. Yan, P. L. Tran, K.-I. Jang, J. W. Lee, Epidermal mechano-acoustic sensing electronics for cardiovascular diagnostics and human-machine interfaces, Sci. Adv. 2, e1601185 (2016).
9. P. Mostafalu, M. Akbari, K. A. Alberti, Q. Xu, A. Khademhosseini, S. R. Sonkusale, A toolkit of thread-based microfluidics, sensors, and electronics for 3D tissue embedding for medical diagnostics, Microsystems Nanoeng. 2 (2016), doi:10.1038/micronano.2016.39.
10. T. R. Dargaville, B. L. Farrugia, J. A. Broadbent, S. Pace, Z. Upton, N. H. Voelcker, Sensors and imaging for wound healing: A review, Biosens. Bioelectron. 41, 30-42 (2013).
11. A. Koh, D. Kang, Y. Xue, S. Lee, R. M. Pielak, J. Kim, T. Hwang, S. Min, A. Banks, P. Bastien, A soft, wearable microfluidic device for the capture, storage, and colorimetric sensing of sweat, Sci. Transl. Med. 8, 366ra165-366ra165 (2016).
12. G. Gethin, The significance of surface pH in chronic wounds, Wounds UK 3, 52-56 (2007).
13. L. A. Schneider, A. Korber, S. Grabbe, J. Dissemond, Influence of pH on wound-healing: A new perspective for wound-therapy?Arch. Dermatol. Res. 298, 413-420 (2007).
14. K. Y. Lee, D. J. Mooney, Alginate: properties and biomedical applications, Prog. Polym. Sci. 37, 106-126 (2012).
15. D. Jain, D. Bar-Shalom, Alginate drug delivery systems: application in context of pharmaceutical and biomedical research, Drug Dev. Ind. Pharm. 40, 1576-1584 (2014).
16. W. Paul, C. P. Sharma, Chitosan and alginate wound dressings: a short review, Trends Biomater Artif Organs 18, 18-23 (2004).
17. K. Murakami, H. Aoki, S. Nakamura, S. Nakamura, M. Takikawa, M. Hanzawa, S. Kishimoto, H. Hattori, Y. Tanaka, T. Kiyosawa, Y. Sato, M. Ishihara, Hydrogel blends of chitin/chitosan, fucoidan and alginate as healing-impaired wound dressings, Biomaterials 31, 83-90 (2010).
18. S. Bagherifard, A. Tamayol, P. Mostafalu, M. Akbari, M. Comotto, N. Annabi, M. Ghaderi, S. Sonkusale, M. R. Dokmeci, A. Khademhosseini, Dermal Patch with Integrated Flexible Heater for on Demand Drug Delivery, Adv. Healthc. Mater. 5, 175-184 (2016).
19. T. Maral, H. Borman, H. Arslan, B. Demirhan, G. Akinbingol, M. Haberal, Effectiveness of human amnion preserved long-term in glycerol as a temporary biological dressing, Burns 25, 625-635 (1999).
20. M. Lavorgna, F. Piscitelli, P. Mangiacapra, G. G. Buonocore, Study of the combined effect of both clay and glycerol plasticizer on the properties of chitosan films, Carbohydr. Polym. 82, 291-298 (2010).
21. S. M. Bishop, M. Walker, A. A. Rogers, W. Y. Chen, Importance of moisture balance at the wound-dressing interface., J. Wound Care 12, 125-128 (2003).
22. D. Okan, K. Woo, E. A. Ayello, G. Sibbald, The role of moisture balance in wound healing, Adv. Skin Wound Care 20, 39-53 (2007).
23. X. Yang, K. Yang, S. Wu, X. Chen, F. Yu, J. Li, M. Ma, Z. Zhu, Cytotoxicity and wound healing properties of PVA/ws-chitosan/glycerol hydrogels made by irradiation followed by freeze-thawing, Radiat. Phys. Chem. 79, 606-611 (2010).
24. P. H. Corkhill, C. J. Hamilton, B. J. Tighe, Synthetic hydrogels VI. Hydrogel composites as wound dressings and implant materials, Biomaterials 10, 3-10 (1989).
25. I. Yetim, O. V Özkan, A. Dervişoglu, K. Erzurumlu, E. Canbolant, Effect of local gentamicin application on healing and wound infection in patients with modified radical mastectomy: a prospective randomized study, J. Int. Med. Res. 38, 1442-1447 (2010).
26. W. K. Chang, S. Srinivasa, A. D. MacCormick, A. G. Hill, Gentamicin-collagen implants to reduce surgical site infection: systematic review and meta-analysis of randomized trials (2013).
27. M. N. Mavros, P. K. Mitsikostas, V. G. Alexiou, G. Peppas, M. E. Falagas, Gentamicin collagen sponges for the prevention of sternal wound infection: a meta-analysis of randomized controlled trials, J. Thorac. Cardiovasc. Surg. 144, 1235-1240 (2012).
28. J. Sun, H. Tan, Alginate-based biomaterials for regenerative medicine applications, Materials (Basel). 6, 1285-1309 (2013).
29. J. R. Davidson, Current concepts in wound management and wound healing products, Vet. Clin. North Am. Small Anim. Pract. 45, 537-564 (2015).
30. R. D. Pedde, B. Mirani, A. Navaei, T. Styan, S. Wong, M. Mehrali, A. Thakur, N. K. Mohtaram, A. Bayati, A. Dolatshahi-Pirouz, Emerging Biofabrication Strategies for Engineering Complex Tissue Constructs, Adv. Mater. (2017).
31. S. Ghorbanian, M. A. Qasaimeh, M. Akbari, A. Tamayol, D. Juncker, Microfluidic direct writer with integrated declogging mechanism for fabricating cell-laden hydrogel constructs, Biomed. Microdevices 16, 387-395 (2014).
32. J. S. Miller, K. R. Stevens, M. T. Yang, B. M. Baker, D.-H. T. Nguyen, D. M. Cohen, E. Toro, A. A. Chen, P. A. Galie, X. Yu, Rapid casting of patterned vascular networks for perfusable engineered three-dimensional tissues, Nat. Mater. 11, 768-774 (2012).
33. S. Fuchs, J. Pané-Farré, C. Kohler, M. Hecker, S. Engelmann, Anaerobic gene expression in *Staphylococcus aureus*, J. Bacteriol. 189, 4275-4289 (2007).
34. E. A. Dawes, D. W. Ribbons, The endogenous metabolism of microorganisms, Annu. Rev. Microbiol. 16, 241-264 (1962).
35. Y. Chen, Y. Zilberman, P. Mostafalu, S. R. Sonkusale, Paper based platform for colorimetric sensing of dissolved $NH_3$ and $CO_2$, Biosens. Bioelectron. 67, 477-484 (2015).
36. D. Queen, J. D. S. Gaylor, J. H. Evans, J. M. Courtney, W. H. Reid, The preclinical evaluation of the water vapour transmission rate through burn wound dressings, Biomaterials 8, 367-371 (1987).
37. D. Seliktar, Designing cell-compatible hydrogels for biomedical applications, Science (80-.). 336, 1124-1128 (2012).
38. M. Akbari, A. Tamayol, V. Laforte, N. Annabi, A. H. Najafabadi, A. Khademhosseini, D. Juncker, Composite living fibers for creating tissue constructs using textile techniques, Adv. Funct. Mater. 24, 4060-4067 (2014).
39. J. P. E. Junker, C. C. Y. Lee, S. Samaan, F. Hackl, E. Kiwanuka, R. A. Minasian, D. M. Tsai, L. E. Tracy, A. B. Onderdonk, E. Eriksson, Topical delivery of ultrahigh concentrations of gentamicin is highly effective in reducing bacterial levels in infected porcine full-thickness wounds, Plast. Reconstr. Surg. 135, 151-159 (2015).

Mobile Device

Figure 32:
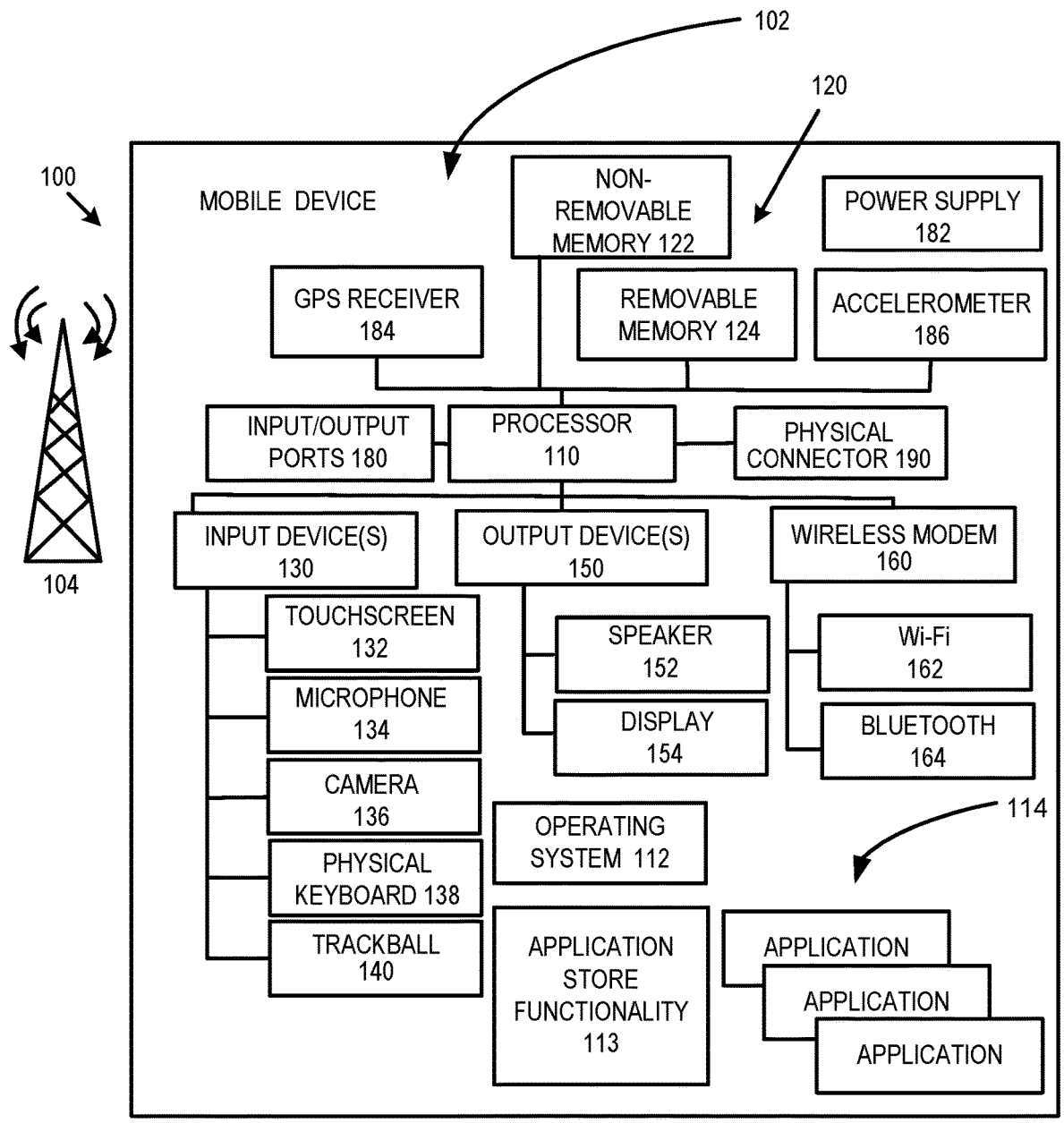
FIG. 32 is a schematic block diagram illustrating a representative embodiment of a mobile device that may be used to implement the image data collection and/or wound exudate parameter value determination functionality described herein.

FIG. 32 is a system diagram depicting an example mobile device 100 including a variety of optional hardware and software components, shown generally at 102. Any components 102 in the mobile device can communicate with any other component, although not all connections are shown, for ease of illustration. The mobile device can be any of a variety of computing devices (e.g., cell phone, smartphone, handheld computer, Personal Digital Assistant (PDA), etc.) and can allow wireless two-way communications with one or more mobile communications networks 104, such as a cellular, satellite, or other network.

The illustrated mobile device 100 can include a controller or processor 110 (e.g., signal processor, microprocessor, ASIC, or other control and processing logic circuitry) for performing such tasks as signal coding, data processing, input/output processing, power control, and/or other functions. An operating system 112 can control the allocation and usage of the components 102 and support for one or more application programs 114. The application programs can include common mobile computing applications (e.g., email applications, calendars, contact managers, web browsers, messaging applications), or any other computing application. Functionality 113 for accessing an application store can also be used for acquiring and updating application programs 114.

The illustrated mobile device 100 can include memory 120. Memory 120 can include non-removable memory 122 and/or removable memory 124. The non-removable memory 122 can include RAM, ROM, flash memory, a hard disk, or other well-known memory storage technologies. The removable memory 124 can include flash memory or a Subscriber Identity Module (SIM) card, which is well known in GSM communication systems, or other well-known memory storage technologies, such as "smart cards." The memory 120 can be used for storing data and/or code for running the operating system 112 and the applications 114. Example data can include web pages, text, images, sound files, video data, or other data sets to be sent to and/or received from one or more network servers or other devices via one or more wired or wireless networks. The memory 120 can be used to store a subscriber identifier, such as an International Mobile Subscriber Identity (IMSI), and an equipment identifier, such as an International Mobile Equipment Identifier (IMEI). Such identifiers can be transmitted to a network server to identify users and equipment.

The mobile device 100 can support one or more input devices 130, such as a touchscreen 132, microphone 134, camera 136, physical keyboard 138 and/or trackball 140 and one or more output devices 150, such as a speaker 152 and a display 154. Other possible output devices (not shown) can include piezoelectric or other haptic output devices. Some devices can serve more than one input/output function. For example, touchscreen 132 and display 154 can be combined in a single input/output device.

The input devices 130 can include a Natural User Interface (NUI). An NUI is any interface technology that enables a user to interact with a device in a "natural" manner, free from artificial constraints imposed by input devices such as mice, keyboards, remote controls, and the like. Examples of NUI methods include those relying on speech recognition, touch and stylus recognition, gesture recognition both on screen and adjacent to the screen, air gestures, head and eye tracking, voice and speech, vision, touch, gestures, and machine intelligence. Other examples of a NUI include motion gesture detection using accelerometers/gyroscopes, facial recognition, 3D displays, head, eye, and gaze tracking, immersive augmented reality and virtual reality systems, all of which provide a more natural interface, as well as technologies for sensing brain activity using electric field sensing electrodes (EEG and related methods). Thus, in one specific example, the operating system 112 or applications 114 can comprise speech-recognition software as part of a voice user interface that allows a user to operate the device 100 via voice commands. Further, the device 100 can comprise input devices and software that allows for user interaction via a user's spatial gestures, such as detecting and interpreting gestures to provide input to a gaming application.

A wireless modem 160 can be coupled to an antenna (not shown) and can support two-way communications between the processor 110 and external devices, as is well understood in the art. The modem 160 is shown generically and can include a cellular modem for communicating with the mobile communication network 104 and/or other radio-based modems (e.g., Bluetooth 164 or Wi-Fi 162). The wireless modem 160 is typically configured for communication with one or more cellular networks, such as a GSM network for data and voice communications within a single cellular network, between cellular networks, or between the mobile device and a public switched telephone network (PSTN).

The mobile device can further include at least one input/output port 180, a power supply 182, a satellite navigation system receiver 184, such as a Global Positioning System (GPS) receiver, an accelerometer 186, and/or a physical connector 190, which can be a USB port, IEEE 1394 (FireWire) port, and/or RS-232 port. The illustrated components 102 are not required or all-inclusive, as any components can be deleted and other components can be added.

Example Computing Environment

Figure 33:
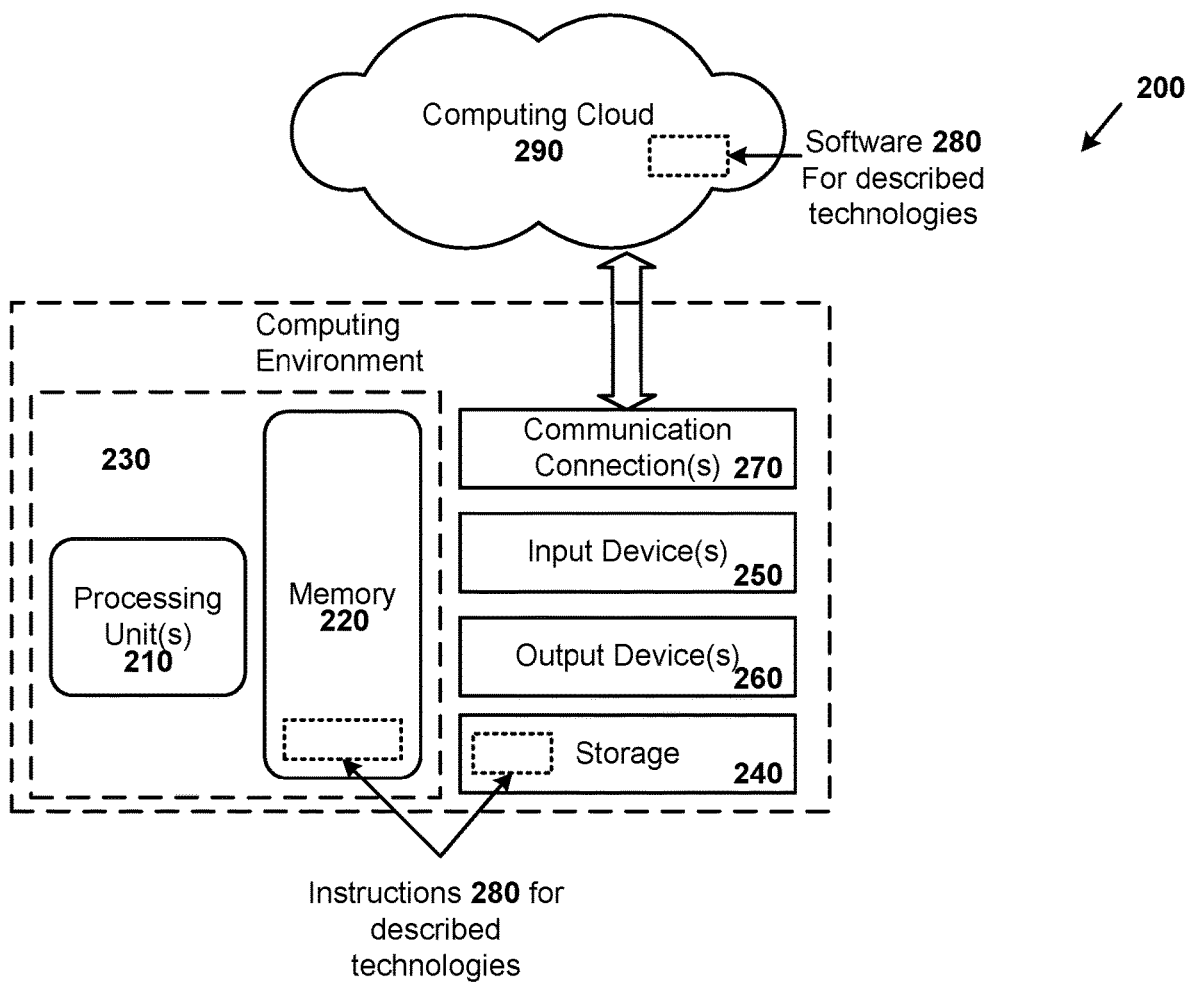
FIG. 33 is a schematic block diagram illustrating a representative computing environment for implementing the image processing and wound exudate parameter value determination functionality described herein.

FIG. 33 illustrates a generalized example of a suitable computing environment 200 in which the described embodiments, techniques, and technologies, including analyzing image data of the various sensor elements described herein and determining the value of various wound parameters based on the image data, can be implemented.

The computing environment 200 is not intended to suggest any limitation as to scope of use or functionality of the technology, as the technology may be implemented in diverse general-purpose or special-purpose computing environments. For example, the disclosed technology may be implemented with other computer system configurations, including hand held devices, multi-processor systems, programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

With reference to FIG. 33, the computing environment 200 includes at least one processing unit 210 and memory 220. In FIG. 33, this most basic configuration 230 is included within a dashed line. The processing unit 210 executes computer-executable instructions and may be a real or a virtual processor. In a multi-processing system, multiple processing units execute computer-executable instructions to increase processing power and as such, multiple processors can be running simultaneously. The memory 220 may be volatile memory (e.g., registers, cache, RAM), non-volatile memory (e.g., ROM, EEPROM, flash memory, etc.), or some combination of the two. The memory 220 stores software 280, images, and video that can, for example, implement the technologies described herein. A computing environment may have additional features. For example, the computing environment 200 includes storage 240, one or more input devices 250, one or more output devices 260, and one or more communication connections 270. An interconnection mechanism (not shown) such as a bus, a controller, or a network, interconnects the components of the computing environment 200. Typically, operating system software (not shown) provides an operating environment for other software executing in the computing environment 200, and coordinates activities of the components of the computing environment 200.

The storage 240 may be removable or non-removable, and includes magnetic disks, magnetic tapes or cassettes, CD-ROMs, CD-RWs, DVDs, or any other medium which can be used to store information and that can be accessed within the computing environment 200. The storage 240 stores instructions for the software 280, plugin data, and messages, which can be used to implement technologies described herein.

The input device(s) 250 may be a touch input device, such as a keyboard, keypad, mouse, touch screen display, pen, or trackball, a voice input device, a scanning device, or another device, that provides input to the computing environment 200. For audio, the input device(s) 250 may be a sound card or similar device that accepts audio input in analog or digital form, or a CD-ROM reader that provides audio samples to the computing environment 200. The output device(s) 260 may be a display, printer, speaker, CD-writer, or another device that provides output from the computing environment 200.

The communication connection(s) 270 enable communication over a communication medium (e.g., a connecting network) to another computing entity. The communication medium conveys information such as computer-executable instructions, compressed graphics information, video, or other data in a modulated data signal. The communication connection(s) 270 are not limited to wired connections (e.g., megabit or gigabit Ethernet, Infiniband, Fibre Channel over electrical or fiber optic connections) but also include wireless technologies (e.g., RF connections via Bluetooth, WiFi (IEEE 802.11a/b/n), WiMax, cellular, satellite, laser, infrared) and other suitable communication connections for providing a network connection for the disclosed computing devices. In a virtual host environment, the communication(s) connections can be a virtualized network connection provided by the virtual host.

Some embodiments of the disclosed methods can be performed using computer-executable instructions implementing all or a portion of the disclosed technology in a computing cloud 290. For example, the disclosed methods can be executed on processing units 210 located in the computing environment 230, or the disclosed methods can be executed on servers located in the computing cloud 290.

Computer-readable media are any available media that can be accessed within a computing environment 200. By way of example, and not limitation, with the computing environment 200, computer-readable media include memory 220 and/or storage 240. As should be readily understood, the term computer-readable storage media includes the media for data storage such as memory 220 and storage 240, and not transmission media such as modulated data signals.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing quantities of components, molecular weights, percentages, temperatures, times, and so forth, as used in the specification or claims are to be understood as being modified by the term "about." Accordingly, unless otherwise indicated,

The invention claimed is:
1. A wound covering, comprising:
a flexible main body;
a sensor element incorporated into the main body, the sensor element comprising a mesh formed from a plurality of fibers, the sensor element being configured to undergo a detectable change in appearance in response to a change in a parameter associated with wound exudate, wherein the fibers comprise a plurality of sensor particles and a hydrogel, the sensor particles comprising
one or more indicator compounds configured to undergo the detectable change in appearance in response to the change in the parameter associated with the wound exudate, and
beads comprising an ion-exchange resin or a hydrogel; and
a supply of therapeutic agent configured to diffuse the therapeutic agent from the wound covering into a wound when the wound covering is placed on the wound.
2. The wound covering of claim 1, wherein:
the one or more indicator compounds include pH-sensitive dye, glucose-sensitive dye, lactate-sensitive dye, or any combination thereof.
3. The wound covering of claim 2, wherein:
the sensor element comprises a first region, a second region, a third region, and a fourth region; and
the sensor particles in the fibers of the first region comprise the pH-sensitive dye;
the sensor particles in the fibers of the second region comprise the glucose-sensitive dye;

the sensor particles in the fibers of the third region comprise the lactate-sensitive dye; and the sensor particles in the fibers of the fourth region are dye-free.

4. The wound covering of claim 1, wherein the sensor element is incorporated into the main body such that a lower surface of the sensor element forms part of a lower surface of the main body.

5. The wound covering of claim 1, wherein the therapeutic agent comprises an antibiotic agent, an antifungal agent, a cellular growth-promoting agent, or any combination thereof.

6. The wound covering of claim 1, further comprising a plurality of particles configured to release oxygen into the wound when the covering is placed on the wound.

7. A method of using the wound covering of claim 1, the method comprising:
applying the wound covering to a wound; and
detecting the detectable change in appearance of the sensor element.

8. The method of claim 7, wherein the detecting the detectable change in appearance of the sensor element further comprises:
producing image data of the sensor element, the image data comprising data of a color of the sensor element; and
comparing the data of the color of the sensor element to predetermined color data of the sensor element to determine a value of a parameter associated with exudate from the wound; and
removing the wound covering from the wound if the value of the parameter associated with the exudate from the wound indicates a presence of infection in the wound.

9. A wound covering, comprising:
a flexible main body including at least
a first layer comprising a hydrogel; and
a second layer disposed on the first layer, the second layer comprising a porous hydrophobic material;
a sensor element incorporated into the main body and at least partially incorporated into the first layer, the sensor element comprising a mesh formed from a plurality of fibers, the sensor element being configured to undergo a change in appearance in response to a change in a parameter associated with wound exudate; and
a supply of therapeutic agent configured to diffuse the therapeutic agent from the wound covering into a wound when the wound covering is placed on the wound.

10. The wound covering of claim 9, wherein:
the wound covering further comprises a third layer disposed on the first layer on an opposite side of the first layer from the second layer such that the first layer is between the third layer and the second layer; and
the third layer is configured to inhibit bacteria growth.

11. The wound covering of claim 9, wherein the supply of therapeutic agent is incorporated into the hydrogel of the first layer.

12. A wound covering, comprising:
a flexible main body;
a sensor element incorporated into the main body, the sensor element comprising a mesh formed from a plurality of fibers, the sensor element being configured to undergo a change in appearance in response to a change in a parameter associated with wound exudate;

a supply of therapeutic agent configured to diffuse the therapeutic agent from the wound covering into a wound when the wound covering is placed on the wound; and a therapeutic agent delivery element including a mesh formed from a plurality of fibers, the plurality of fibers of the mesh of the therapeutic agent delivery element comprising a hydrogel, wherein
the therapeutic agent is incorporated into the hydrogel.

13. A wound covering, comprising:
a flexible main body;
a sensor element incorporated into the main body, the sensor element comprising a mesh formed from a plurality of fibers, the sensor element being configured to undergo a change in appearance in response to a change in a parameter associated with wound exudate;
a supply of therapeutic agent configured to diffuse the therapeutic agent from the wound covering into a wound when the wound covering is placed on the wound; and
a therapeutic agent delivery element including a mesh formed from a plurality of fibers, the plurality of fibers of the mesh of the therapeutic agent delivery element comprising a plurality of porous hydrogel particles, the porous hydrogel particles comprising the therapeutic agent, and
the porous hydrogel particles are configured to release the therapeutic agent when the parameter exceeds a predetermined threshold.

14. The wound covering of claim 13, wherein the parameter comprises pH of the wound exudate or a temperature of the porous hydrogel particles.

15. The wound covering of claim 14, wherein the wound covering further comprises a heating element configured to selectively heat the delivery element.

16. A wound covering, comprising:
a flexible main body;
a sensor element incorporated into the main body, the sensor element comprising a mesh formed from a plurality of fibers, the sensor element being configured to undergo a change in appearance in response to a change in a parameter associated with wound exudate;
a supply of therapeutic agent configured to diffuse the therapeutic agent from the wound covering into a wound when the wound covering is placed on the wound; and
a humidity sensor element incorporated into the main body, the humidity sensor element comprising a substrate having a coating configured to undergo a change in appearance in response to a change in humidity.

17. A wound covering, comprising:
a flexible main body;
a sensor element having a first region, a second region, a third region, and a fourth region incorporated into the main body, the sensor element comprising a mesh formed from a plurality of fibers, the sensor element being configured to undergo a change in appearance in response to a change in a parameter associated with wound exudate,
wherein the fibers comprise a plurality of sensor particles, the sensor particles comprising one or more indicator compounds including pH-sensitive dye, glucose-sensitive dye, lactate-sensitive dye, or any combination thereof, configured to undergo the change in appearance in response to the change in the parameter associated with the wound exudate, and wherein
the sensor particles in the fibers of the first region comprise the pH-sensitive dye,
the sensor particles in the fibers of the second region comprise the glucose-sensitive dye,
the sensor particles in the fibers of the third region comprise the lactate-sensitive dye, and
the sensor particles in the fibers of the fourth region are dye-free; and
a supply of therapeutic agent configured to diffuse the therapeutic agent from the wound covering into a wound when the wound covering is placed on the wound.

* * * * *